US008609089B2

(12) United States Patent
Langermann et al.

(10) Patent No.: US 8,609,089 B2
(45) Date of Patent: Dec. 17, 2013

(54) COMPOSITIONS OF PD-1 ANTAGONISTS AND METHODS OF USE

(75) Inventors: Solomon Langermann, Baltimore, MD (US); Linda Liu, Clarksville, MD (US)

(73) Assignee: Amplimmune, Inc., Gaithersburg, MD (US)

( * ) Notice: Subject to any disclaimer, the term of this patent is extended or adjusted under 35 U.S.C. 154(b) by 0 days.

(21) Appl. No.: 13/332,154

(22) Filed: Dec. 20, 2011

(65) Prior Publication Data
US 2012/0114648 A1 May 10, 2012

Related U.S. Application Data

(62) Division of application No. 12/547,129, filed on Aug. 25, 2009, now Pat. No. 8,114,845.

(60) Provisional application No. 61/211,697, filed on Apr. 2, 2009, provisional application No. 61/091,694, filed on Aug. 25, 2008, provisional application No. 61/091,709, filed on Aug. 25, 2008, provisional application No. 61/091,705, filed on Aug. 25, 2008.

(51) Int. Cl.
*A61K 39/395* (2006.01)

(52) U.S. Cl.
USPC ........................................................... 424/130.1

(58) Field of Classification Search
None
See application file for complete search history.

(56) References Cited

U.S. PATENT DOCUMENTS

| | | |
|---|---|---|
| 5,632,983 A | 5/1997 | Hadden |
| 6,468,546 B1 | 10/2002 | Mitcham et al. |
| 6,630,575 B2 | 10/2003 | Coyle et al. |
| 6,635,750 B1 | 10/2003 | Coyle et al. |
| 6,803,192 B1 | 10/2004 | Chen |
| 6,808,710 B1 | 10/2004 | Wood et al. |
| 6,965,018 B2 | 11/2005 | Mikesell et al. |
| 7,030,219 B2 | 4/2006 | Pardoll et al. |
| 7,101,550 B2 | 9/2006 | Wood et al. |
| 7,182,942 B2 | 2/2007 | Hadden |
| 7,279,567 B2 | 10/2007 | Mikesell et al. |
| 7,358,354 B2 | 4/2008 | Mikesell et al. |
| 7,368,554 B2 | 5/2008 | Mikesell et al. |
| 7,414,122 B2 | 8/2008 | Fox et al. |
| 7,488,802 B2 | 2/2009 | Collins et al. |
| 7,521,051 B2 | 4/2009 | Collins et al. |
| 7,595,048 B2 | 9/2009 | Honjo et al. |
| 7,709,214 B2 | 5/2010 | Freeman et al. |
| 7,794,710 B2 * | 9/2010 | Chen et al. ................ 424/130.1 |
| 7,892,540 B2 * | 2/2011 | Chen et al. ................ 424/130.1 |
| 8,008,449 B2 | 8/2011 | Korman et al. |
| 8,088,905 B2 | 1/2012 | Collins et al. |
| 8,114,845 B2 | 2/2012 | Langermann et al. |
| 2003/0039653 A1 | 2/2003 | Chen |
| 2006/0110383 A1 | 5/2006 | Honjo |
| 2006/0159685 A1 | 7/2006 | Mikesell et al. |
| 2006/0292593 A1 | 12/2006 | Pardoll et al. |
| 2007/0122378 A1 * | 5/2007 | Freeman et al. ............ 424/85.1 |
| 2007/0166281 A1 | 7/2007 | Kosak |
| 2007/0202077 A1 | 8/2007 | Brodsky |
| 2007/0231344 A1 | 10/2007 | Leadbetter et al. |
| 2008/0118511 A1 | 5/2008 | Freeman et al. |
| 2009/0055944 A1 * | 2/2009 | Korman et al. ............... 800/18 |
| 2009/0217401 A1 | 8/2009 | Korman |
| 2010/0055111 A1 | 3/2010 | Sharma et al. |
| 2011/0159023 A1 | 6/2011 | Langermann |
| 2011/0195068 A1 | 8/2011 | Langermann et al. |
| 2011/0223188 A1 | 9/2011 | Langermann |
| 2013/0017199 A1 | 1/2013 | Langermann |

FOREIGN PATENT DOCUMENTS

| | | |
|---|---|---|
| WO | WO 93/08120 | 4/1993 |
| WO | 0114557 | 3/2001 |
| WO | WO 01/94413 | 12/2001 |
| WO | 0279499 | 10/2002 |
| WO | WO 03/020259 | 3/2003 |
| WO | 03099196 | 12/2003 |
| WO | 2004004771 | 1/2004 |
| WO | 2004056875 | 7/2004 |
| WO | 2004072286 | 8/2004 |
| WO | WO 2005/025494 | 3/2005 |
| WO | 2006121168 | 11/2006 |
| WO | 2006133396 | 12/2006 |
| WO | WO/2007005874 | * 11/2007 |
| WO | 2008083174 | 7/2008 |
| WO | 2009014708 | 1/2009 |
| WO | 2009073533 | 6/2009 |
| WO | WO 2009/101611 | 8/2009 |
| WO | WO 2010/027423 | 3/2010 |

OTHER PUBLICATIONS

Kadhim et al. International Journal of Immunopharmacology, (2000) 22: 659-671.*
Mokyr et al., Cancer Research, (1998) 58: 5301-5304.*
Runion et al., Blood, (2001) 97: 2420-2426.*
Topalian, et al., N. Engl. J. Med., Jun. 28, 2012;366(26):2443-54. (provided by Applicant).*
Mkrtichyan, et al., Eur. J. Immunol., 41:1-10 (2011). (provided by Applicant).*
Wada, et al., "Cyclophosphamide Augments Antitumor Immunity: Studies in an Autochthonous Prostate Cancer Model," *Cancer Res.* 69(10):4309-4318 (2009).
Ernens, et al., "Timed Sequential Treatment With Cyclophosphamide, Doxorubicin, and an Allogeneic Granulocyte-Macrophage Colony-Stimulating Factor—Secreting Breast Tumor Vaccine: A Chemotherapy Dose-Ranging Factorial Study of Safety and Immune Activation," *Journal of Clinical Oncology.* 27(35);5911-5918 (2009).
Gabriel Chong & Michael A Morse, "Combining cancer vaccines with chemotherapy," *Expert Opin. Pharmacother.* 6(16):2813-2820 (2005).

(Continued)

*Primary Examiner* — Ilia Ouspenski
(74) *Attorney, Agent, or Firm* — Pabst Patent Group LLP

(57) ABSTRACT

Methods of treating cancer and infectious diseases utilizing a treatment regimen comprising administering a compound that reduces inhibitory signal transduction in T cells, in combination with a potentiating agent, such as cyclophosphamide, to produce potent T cell mediated responses, are described. Compositions comprising the PD-1 antagonists and potentiating agents useful in the methods of the invention are also disclosed.

23 Claims, 12 Drawing Sheets

(56) References Cited

OTHER PUBLICATIONS

Orsini, et at., "Increased Primary Cell-mediated Immunity in Culture Subsequent to Adriamycin or Daunorubicin Treatment of Spleen Donor Mice1," Cancer Res. 37:1719-1726 (1977).
Finke, et al., "Sunitinib ReversesType-1 Immune Suppression and Decreases T-Regulatory Cells in Renal Cell Carcinoma Patients," Clin Cancer Res. 14(20):6674-6682 (2008).
Bass & Mastrangelo, Cancer Immunal Immunother, vol. 97, pp. 1-12 (1998).
Berd & Mastrangelo, Cancer Res., vol. 48, pp. 1671-1675 (1988).
Berger et al., Clin. Cancer Res., vol. 14, pp. 3044-3051 (2008).
Brode & Cooke, Critical Rev. in Immunology, vol. 28, pp. 109-126 (2008).
Butte et al Immunity, vol. 27, pp. 111-122 (2007).
Currie et al., J. Immun., vol. 183, pp. 7898-7908 (2009).
Dunnull et al., J. Clin. Invest., vol. 115. pp. 3623-3633 (2005).
Erbe et al., J. Biol. Chem vol. 277, pp. 7363-7368 (2002).
Ercolini et al., J. Exp. Med., vol. 201, pp, 1591-1602 (2005).
Francisco et al., J. Exp. Med., vol. 206, pp. 3015-3029 (2009).
Freeman, PNAS, vol. 105, pp. 10275-10276 (2008).
Generali et al., Clin. Cancer Res., vol. 15, pp. 1046-1051 (2009).
Hengst et al., Cancer Res., vol. 40, pp. 2135-2141 (1980).
Hengst et al., Cancer Res., vol. 41, pp. 2163-2167 (1981).
Honeychurch et al., Cancer. Res., vol. 65, pp. 7493-7501 (2005).
Laheru et al., Clin. Cancer Res., vol. 14, pp. 1455-1463 (2008).
Li et al., Clin. Cancer Res., vol. 12, pp. 6808-6816 (2006).
Machiels et al., Cancer Res., vol. 61, pp. 3689-3697 (2001).
Mitchell et al., J. Clin. Oncology, vol. 6, pp. 409-424 (1988).
Mitchell, Int'l Immunopharm., vol. 3, pp. 1051-1059 (2003).
Molnar el al., PNAS, vol. 105, pp. 10483-10488 (2008).
Molnar et al., PNAS, vol. 105, pp. 2658-2663 (2008).
Onlamoon et al., Immunology, vol. 124, pp. 277-293 (2008).
Sitkovsky et al., Brit. J. Pharm., vol. 153, pp. S457-S464 (2008).
Taleb et al., J. Immunology, vol. 176. pp. 2722-2729 (2006).
Tseng et al., J. Exp. Med., vol. 193, pp. 839-845 (2001).
Youngnak et al., BBRC, vol. 307, pp. 672-677 (2003).
Zhang et al., Clin. Immunol., vol. 129, pp. 219-229 (2008).
U.S. Appl. No. 13/332,164, filed Dec. 20, 2011, Langermann, et al.
U.S. Appl. No. 13/312,201, Langermann, et al.
Attwood, "Genomics. The Babel of bioinformatics", Science, 290:471-473 (2000).
Blazer, et al., "Infusion of anti-B7.1 (CD80) and anti-B7.2 (CD86) monoclonal antibodies inhibits murine graft-versus-host disease lethality in part via direct effects on CD4+ and CD8+ T cells", J. Immuno., 157:3250-3259 (1996).
Boon, et al., "Human T cell responses against melanoma", Annu. Rev. Immuno., 24:175-208 (2006).
Lee, et al., "Increased vaccine-specific T cell frequency after peptide-based vaccination correlates with increased susceptibility to in vitro stimulation but does not lead to tumor regression", J. Immuno., 163:6292-6300 (1999).
Metzler, et al., "Solution structure of human CTLA-4 and delineation of a CD80/CD86 binding site conserved in CD28" Nature Structure Biol., 4:527-531 (1997).
Nielsen, et al., "Melanoma vaccines: the paradox of T cell activation without clinical response", Cancer Chemother., Pharmacol., 46 (Suppl.): S62-66 (2000).
Neurobalstoma Treatment, National Cancer Institute, 4 pages, (2011).
Skolnick, et al., "From genes to protein structure and function: novel applications of computational approaches in the genomic era", Trends in Biotech., 18(1):34-39 (2000).
Brahmer, et al, "An anti-pd-1 monoclonal antibody", J Clin. Oncol., 26 (May 20 suppl.) abstract (2008).
Dong, et al., "B7-H1, a third member of the B7 family, co-stimulates T-cell proliferation and interleukin-10 secretion", Nat. Med., 5:1365-69 (1999).
Freeman, at al., "Engagement of the PD-1 immunoinhibitory receptor by a novel B7 family member leads to negative regulation of lymphocyte activation", J. Exp. Med., 192(7):1027-34 (2000).

Ishida, et al, "Induced expression of PD-1, a novel member of the immunoglobulin gene superfamily, upon programmed cell death", EMBO J., 11:3887-95 (1992).
Keir, et al., "PD-1 and its ligands in T-cell immunity", Curr. Opin Immunol., 19:309-14 (2007).
Latchman, et al., "PD-L2 is a second ligand for PD-1 and inhibits T cell activation", Nature Immunol., 2:261-8 (2001).
Le, et al., "Regulatory t-cell modulation using cyciophodsphamide in vaccine approaches: a current perspective", Cancer Res., 72:3439-44 (2012).
Liang, et al., "Design of new oxazaphoaphorine anticancer drugs", Curr. Pham. Des., 13(9):963-78 (2007).
Mokyr, et al., "Realization of the therapeutic potential of CTLA-4 blockade in low-dose chemotherapy-treated tumor-bearing mice", Can. Res., 58:5301-4 (1998).
Nicolini et al., "Oral low-dose cyclophosphamide in metastalic hormone refractory prostate cancer (MHRPC)", Biomed Pharmacotherapcy, 58(8):447-50 (2004).
Nishimura, et al., "Autoimmune dilated cardiomyopathy in PD-1 receptor-deficient deficient mice", Science, 291:319-22 (2001).
Nishimura, et al., "Development of lupus-like autoimmune diseases by disruption of the PD-1 gene encoding an ITIM motif-carrying immunoreceptor", Immunity, 11:141-51 (1999).
Office Action for U.S. Appl. No. 13/332,164 mailed Jul. 27, 2012.
Tamura, et al., "B7-H1 costimulation preferentially enhances CD28-independent T-helper cell function", Blood, 97:1809-1816 (2001).
Tsung, et al., "immune response against large tumors eradicated by treatment with cyclophosphamide and IL-12", Immunol., 160(3)1369-77 (1998).
Van der Most, et al., "Tumor eradication after cyclophosphamide depends on concurrent depletion of regulatory T cells: a role for cycling TNFR2-expressing effector-supressor T cells in limiting effective chemotherapy", Can. Immunol. Immunother., 55:1219-28 (2009).
A Phase 1b Study of MDX-1106 in Subjects with Advanced or Recurrent Malignancies (MDX1106-03), http://clinicaltrials.gov/ct2/show/NCT00730639, pp. 1-5, first received Aug. 4, 2008, last updated Aug. 14, 2012, accessed Aug. 22, 2012.
"Bevacizumab Injection", U.S. National Library of Medicine—the World's Largest Medical Library, http://www.ncbi.nlm.nih.gov/pubmedhealth/PMH0000352, pp. 1-4, last revised Jan. 15, 2012, accessed Aug. 22, 2012.
Brahmer, et al., "Safety and activity of Anti-PD-L1 antibody in patients with advanced cancer", N. Engl. J. Med., 366(26):2455-65, Jun 28. 2012, Epub Jun 2. 2012.
Clinical Program Update Webcast from Medarex as of Jun. 2, 2009, p. 1-20.
Finnefrock, et al., "PD-1 blockade in Rhesus macaques: Impact on chronic infection and prophylactic vaccination", J. Immunology, 182(2):980-7 (2009).
Greenwald, et al., "Negative Co-Receptors on Lymphocytes", Current Opinions in Immunology, 13(3):391-396 (2002).
Medarex 2008 Annual Report, dated Feb. 27, 2009, accessed Aug. 22, 2012.
Mkrtichyan, et al., "Anti-PD-1 synergizes with cyclophophaminde to induce potent anti-tumor vaccine effects through novel mechanisms", Eur. J Immunol., 41:1-10 (2011).
Multiple Ascending Dose (MDX1106-03) (Anti-PD-L1), http://clinicaltrials.gov/ct2/show/NCT00729664, pp. 1-4, first received Aug. 4, 2008, last updated Jun. 18, 2012, accessed Aug. 22, 2012.
"Nivolumab" Statement on a Nonproprietary Name Adopted by the USAN Council, pp. 1-1, accessed Aug. 22, 2012.
Office Action mailed Dec. 19, 2012, in U.S. Appl. No. 13/332,164, pp. 1-11.
Ozkaynak, et al., "Programmed Death-1 Targeting Can Promote Allograph Survival", J. Immunology, 169:6546-6553 (2002).
Pollack, "Drug Helps Defense System Fight Cancer", The New York Times, Jun. 1, 2012.
Pardoll, et al., Immunotherapy earns its spot in the ranks of cancer therapy, JEM, 209(2):201-209 (2012) (abstract only).

(56) References Cited

OTHER PUBLICATIONS

Pardoll, et al., "The blockade of immune checkpoints in cancer immunotherapy," Nature Reviews Cancer, 12:252-264 (2012) (abstract only).

Topalian, et al., "Safety, activity, and immune correlates of Anti-PD-1 antibody in cancer", *N. Engl. J Med.*, 366(26):2443-54. Epub Jun 2. 2012.

Topalian, et al., "Targeting the PD-1/B7-H1(PD-L1) Pathway to Activate Anti-Tumor Immunity", *Curr Opin Immunol.* Apr. 2012; 24(2): 207-212. Doi: 10.1016/j.coi.2011.12.007.

Topalian, et a., "Cancer Immunotherapy Comes of Age", *J. Clinical Onocology*, 20:4828-4836, Dec. 20, 2011.

Winslow, "Cancer Drugs Use Body's Own Defenses", *The Wall Street Journal*, Jun. 1, 2012.

\* cited by examiner

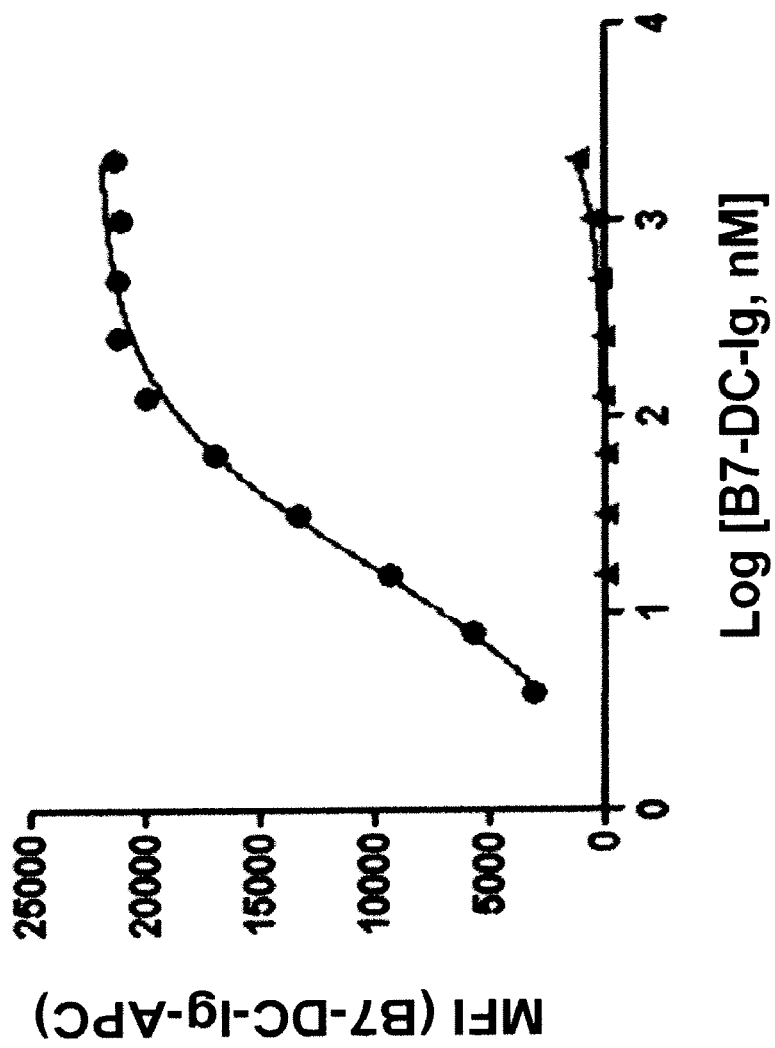
Figure 1. B7-DC-Ig binding to PD-1 expressing CHO cells

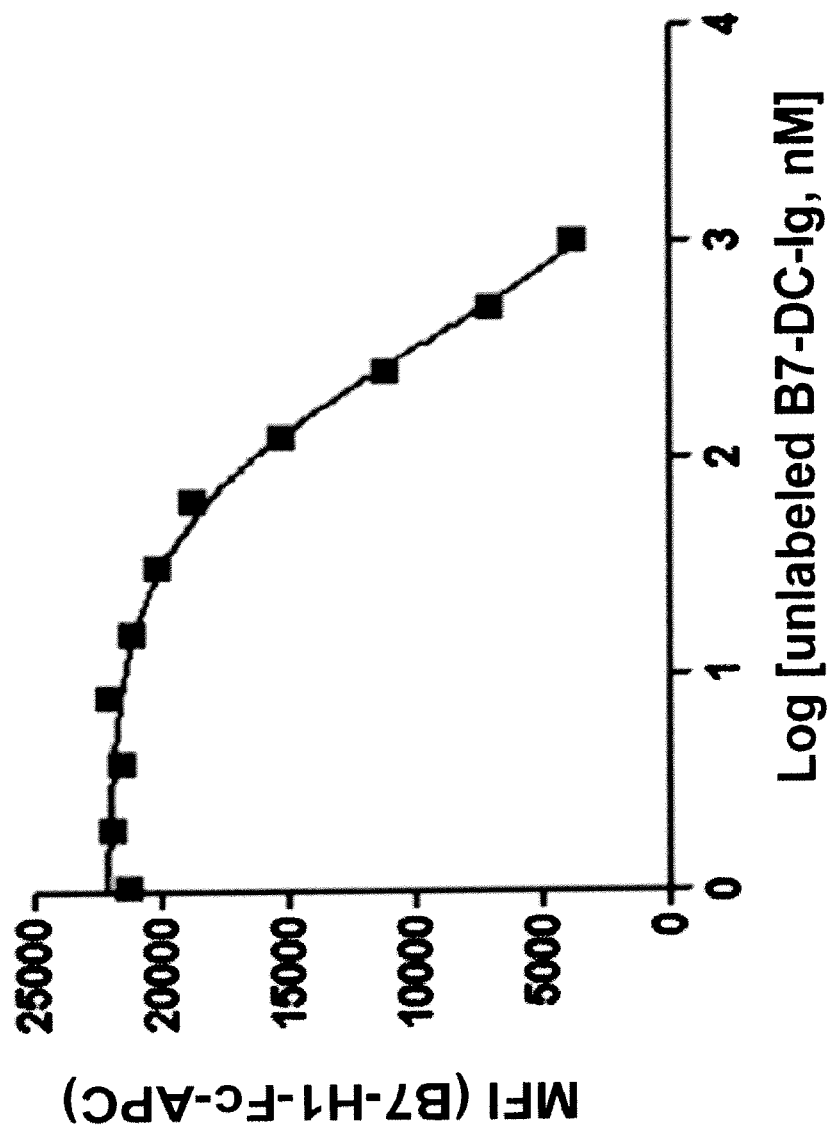
Figure 2. B7-DC-Ig competes with B7-H1 for binding to PD-1

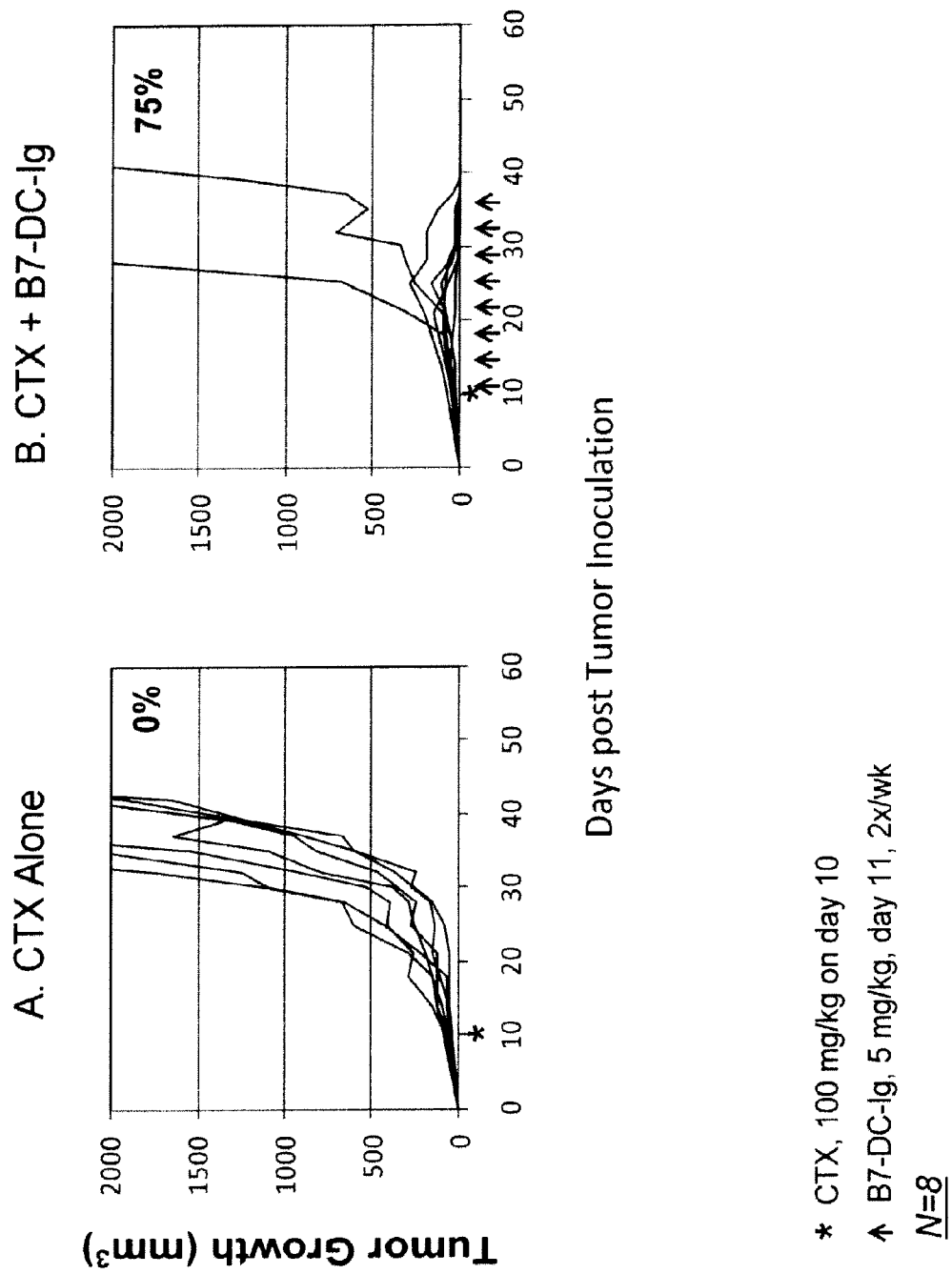

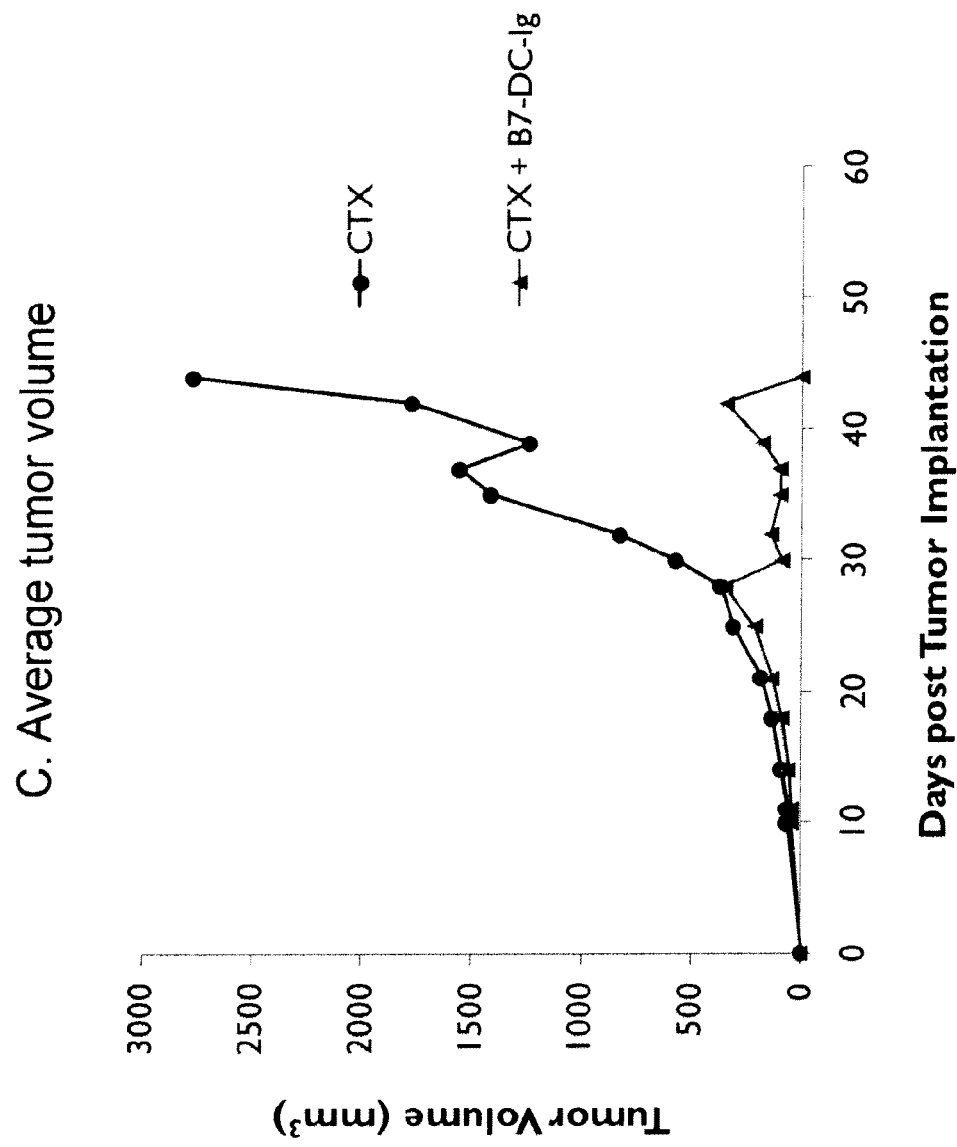
Figure 3-2. CTX combined with B7-DC-Ig
C. Average tumor volume

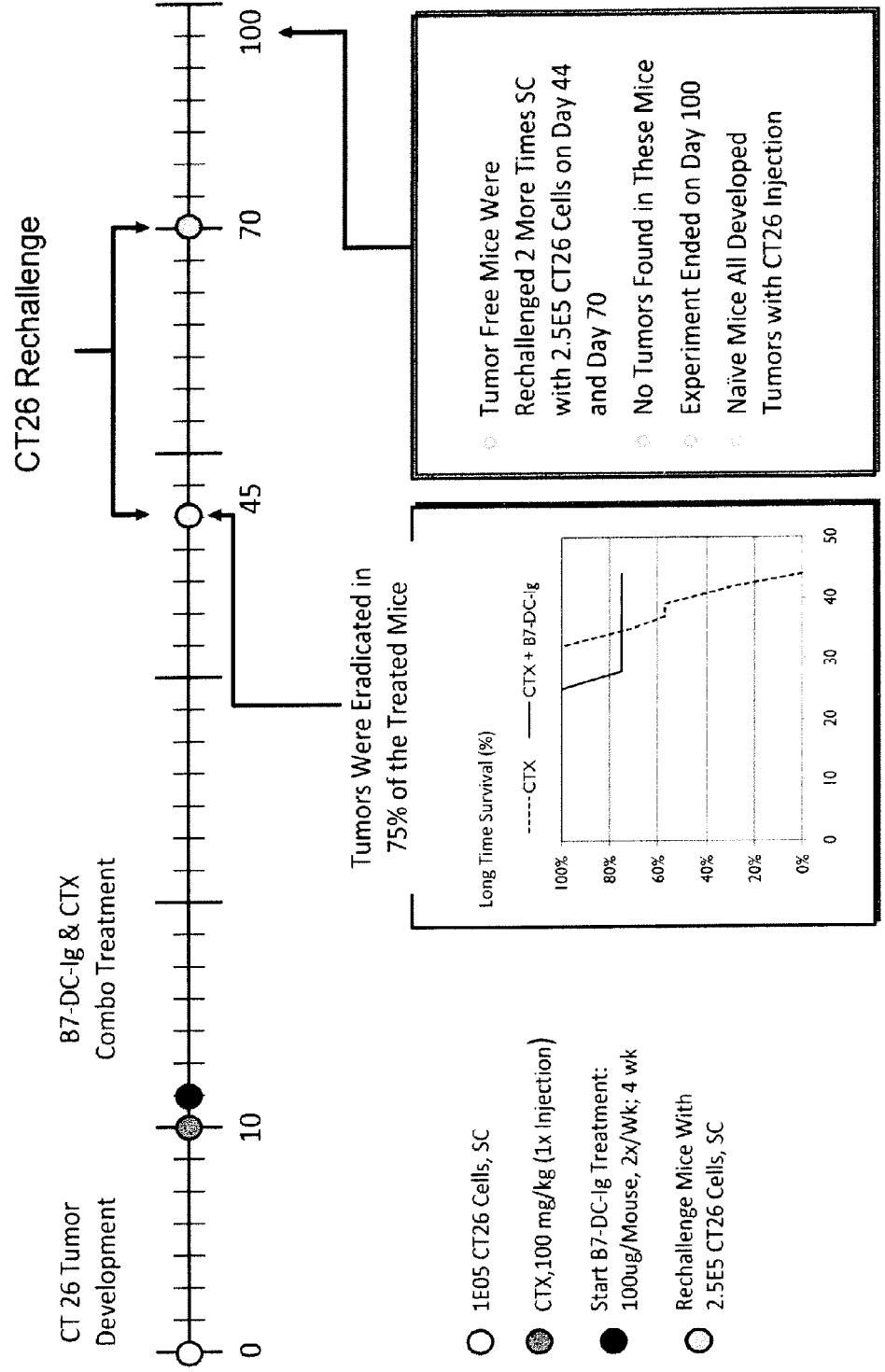

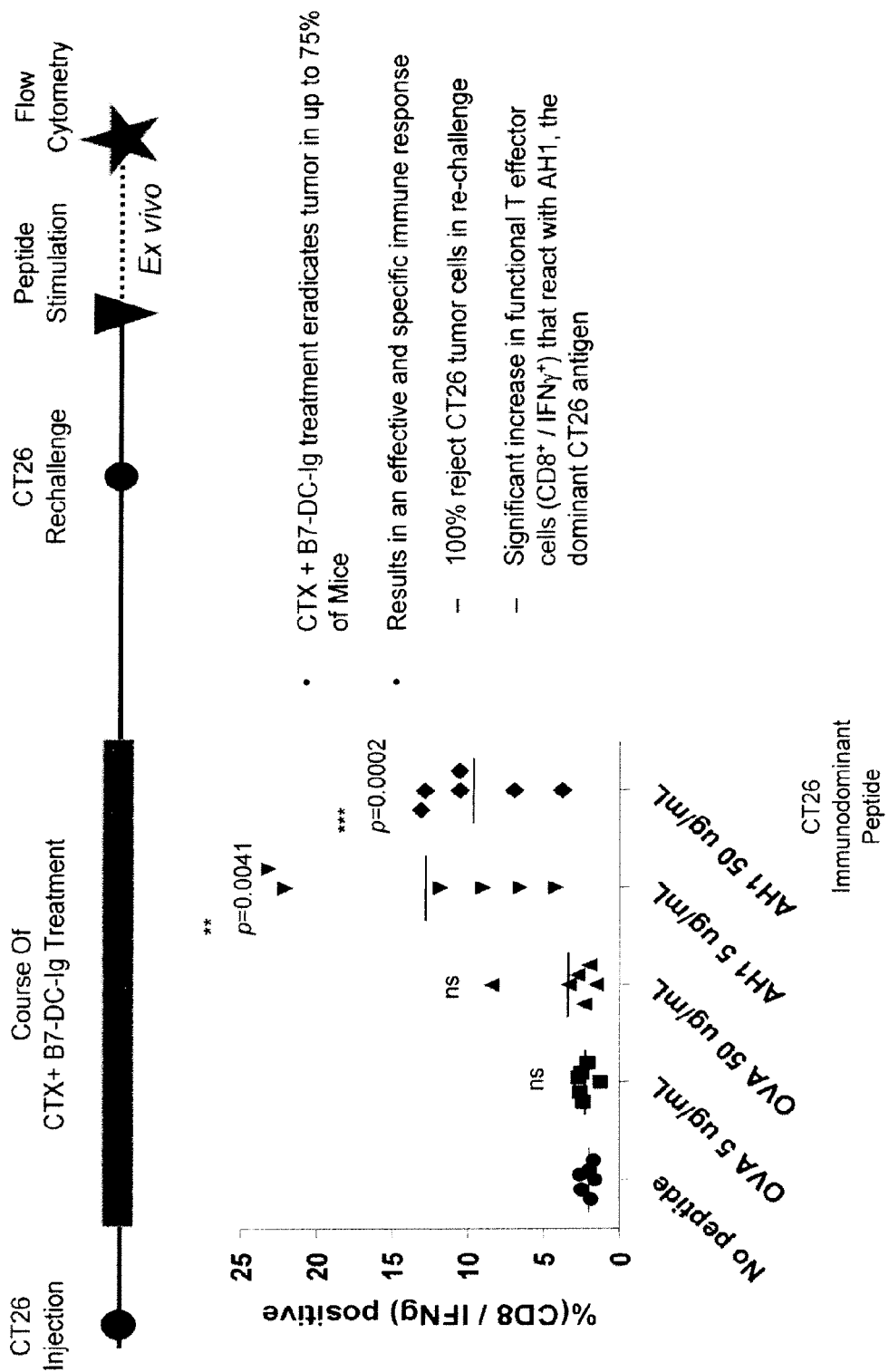

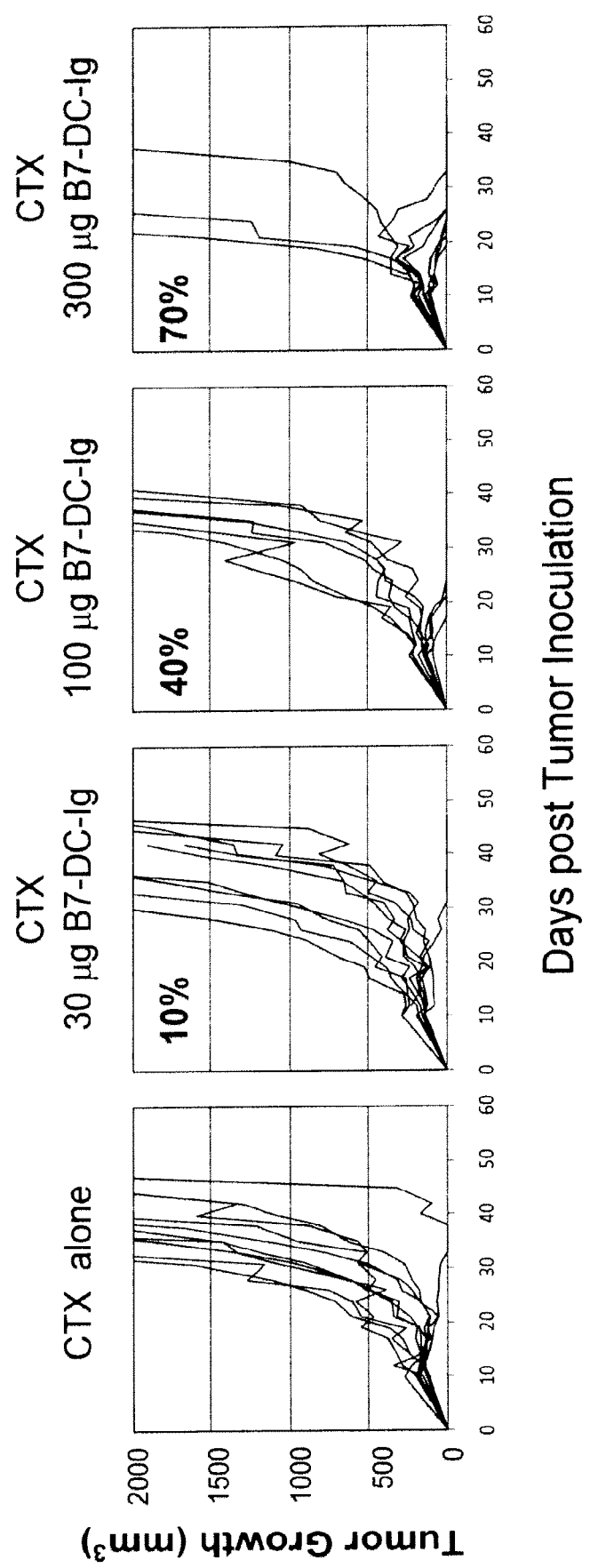
Figure 6. Correlation of B7-DC-Ig Dose with Tumor Eradication: CT26 Model

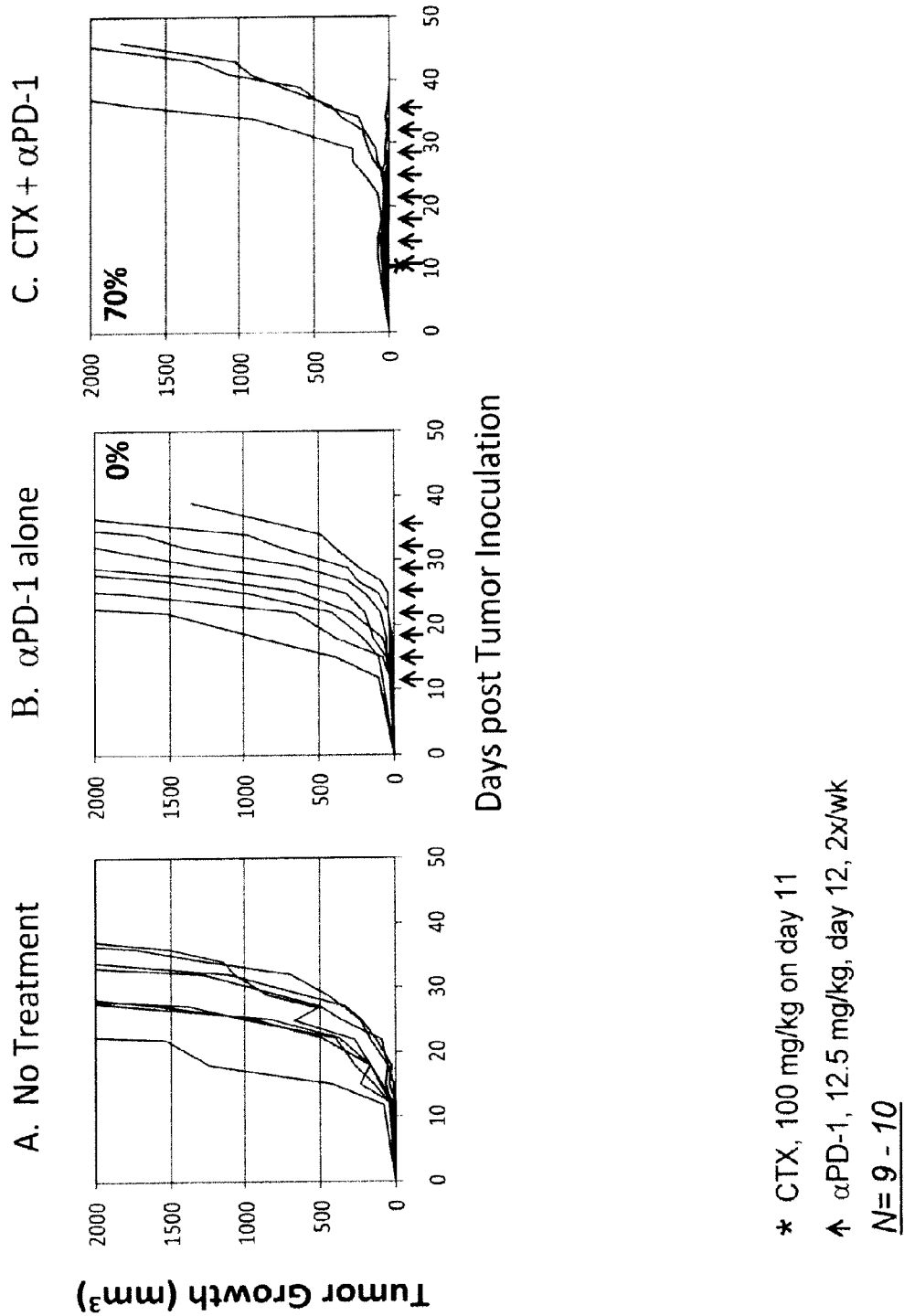

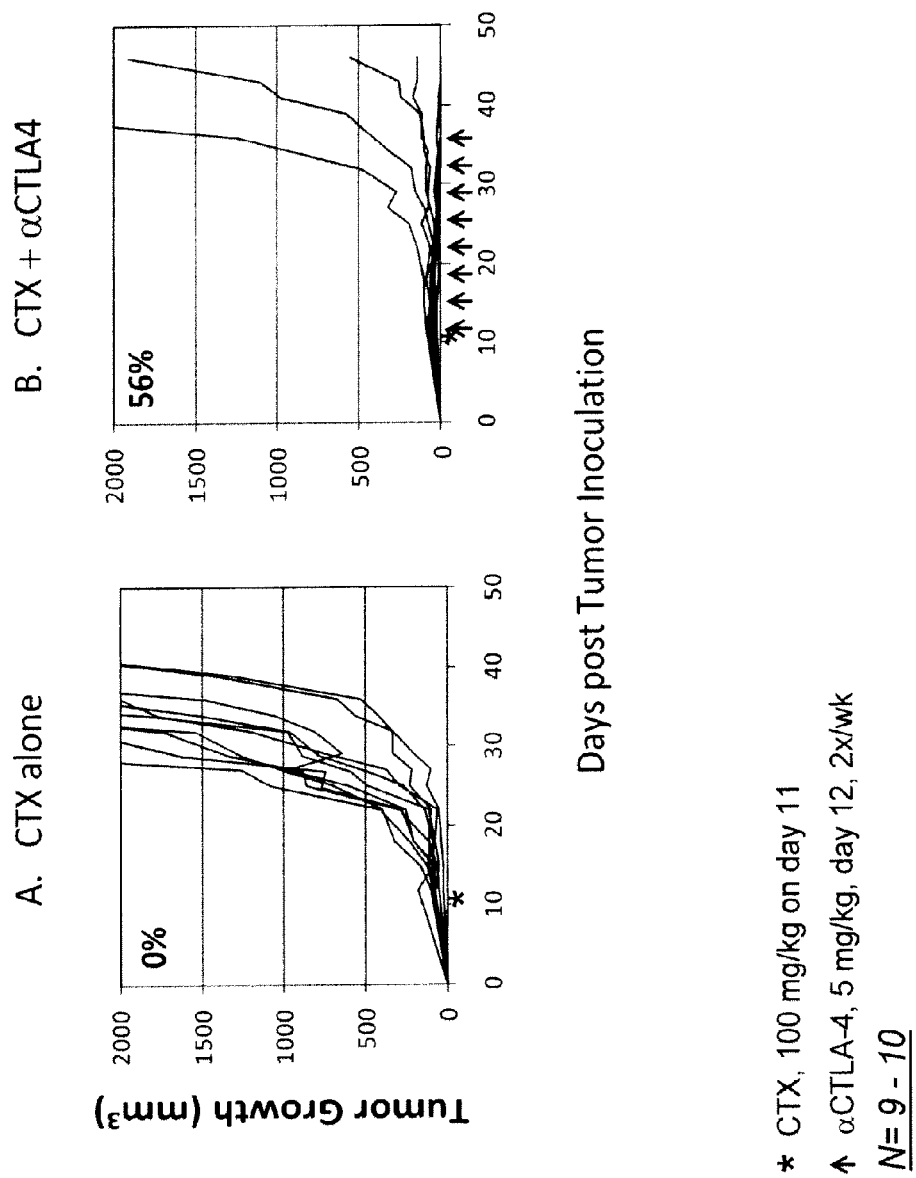

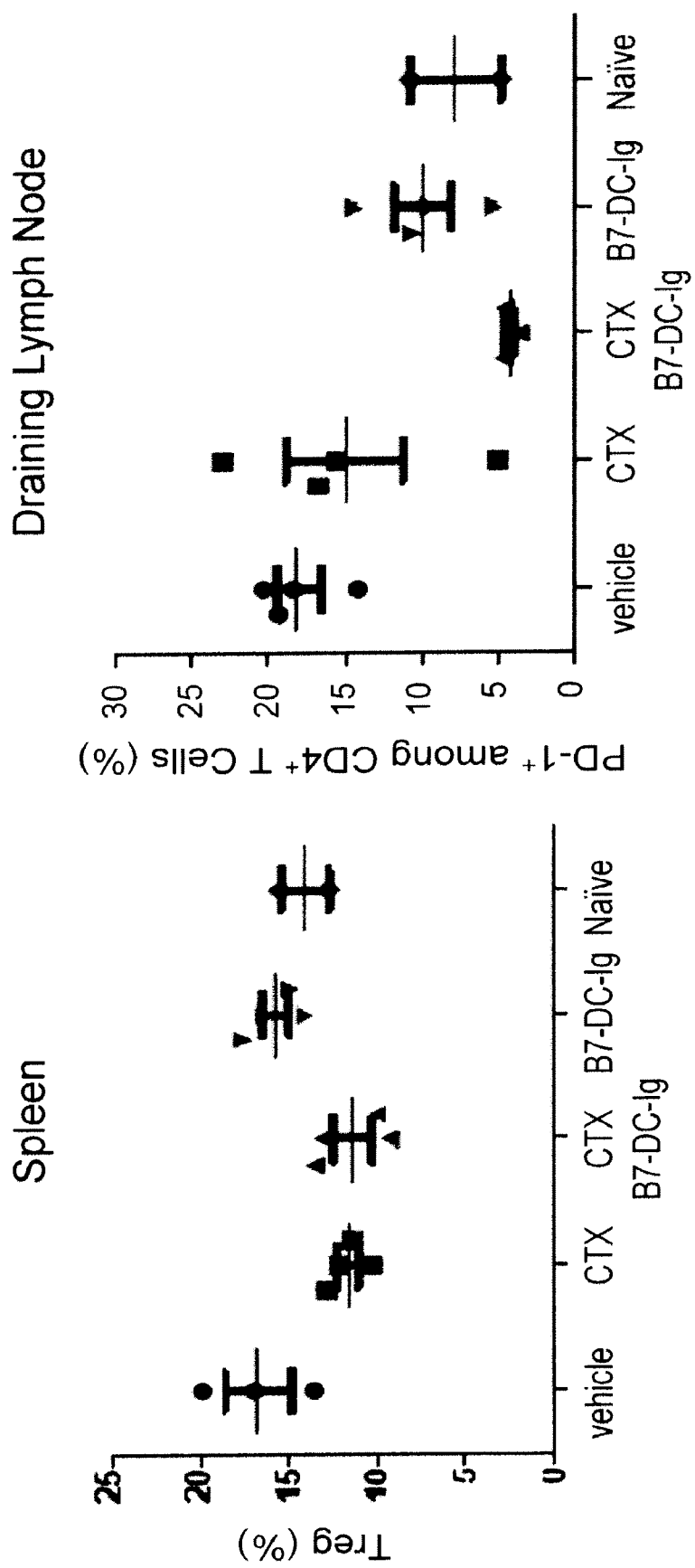
Figure 9. Inclusion of CTX in B7-DC-Ig Regimen Leads to Reduction of Tregs in the Spleen 2 Days Later. B7-DC-Ig Significantly Reduced PD-1$^{high}$ CD4$^+$ T Cells in the Draining Lymph Node.

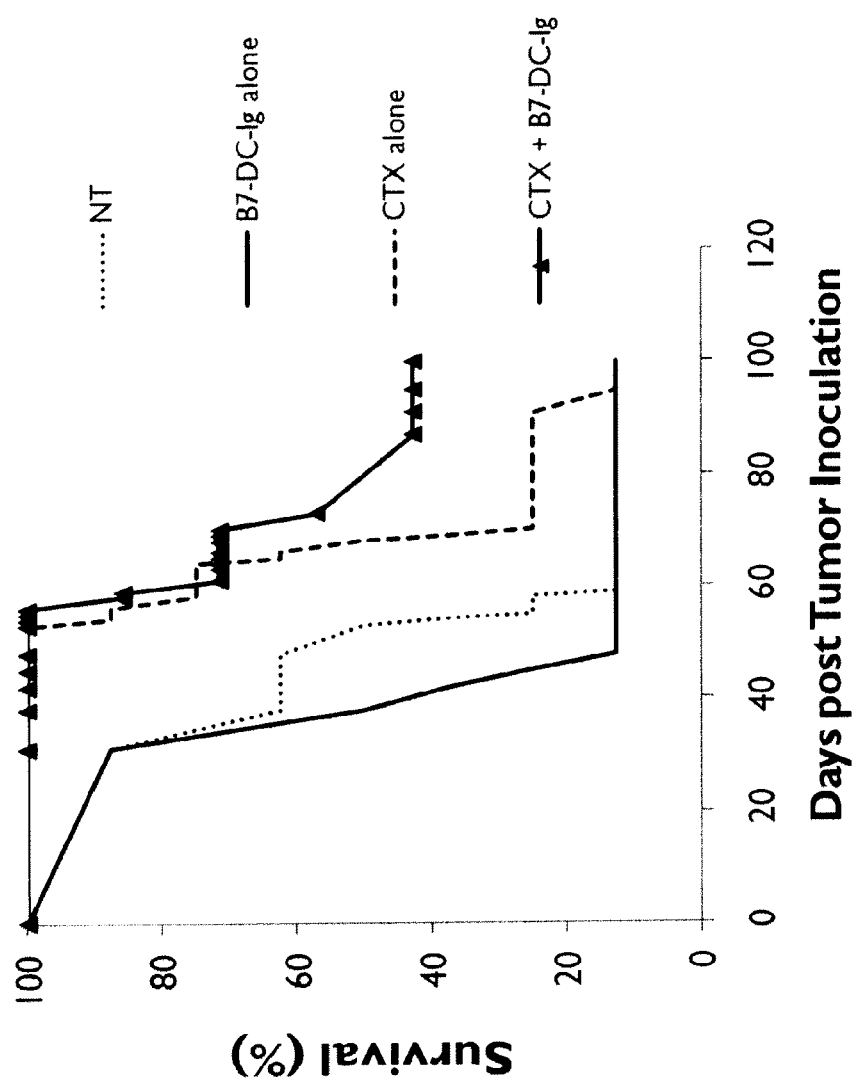
Figure 10. B7-DC-Ig Synergized with CTX in a Lung Met Model

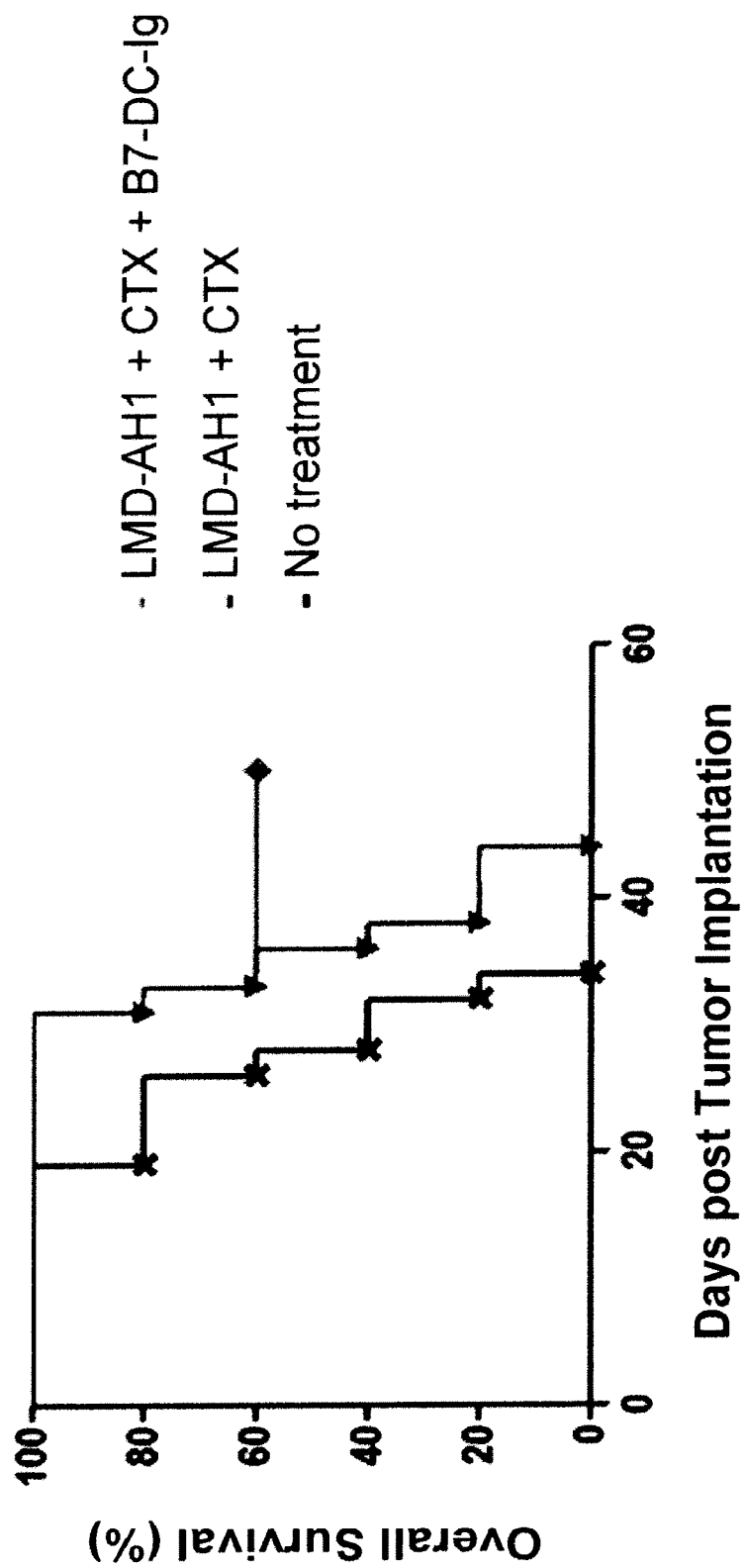
Figure 11. B7-DC-Ig Synergized with CTX and Listeria vaccine in a Liver Met Model

COMPOSITIONS OF PD-1 ANTAGONISTS AND METHODS OF USE

This application is a divisional of pending prior application U.S. Ser. No. 12/547,129 filed Aug. 25, 2009, entitled "Compositions of PD-1 Antagonists and Methods of Use", by Solomon Langermann and Linda Liu, which claims priority to U.S. Ser. No. 61/211,697 filed Apr. 2, 2009, U.S. Ser. No. 61/091,694 filed Aug. 25, 2008, U.S. Ser. No. 61/091,709 filed Aug. 25, 2008, and U.S. Ser. No. 61/091,705 filed Aug. 25, 2008, all of which are herein incorporated by reference in their entirety.

FIELD OF THE INVENTION

The present invention relates to therapeutic compositions containing a compound that prevents inhibitory signal transduction on T cells in combination with potentiating agents and the use of said components together or separately for the induction of T cell responses valuable in disease therapy.

BACKGROUND OF THE INVENTION

The response of T lymphocytes to disease states, such as infection and chronic diseases like cancer, is complicated and involves intercellular interactions and the production of soluble mediators (called cytokines or lymphokines). Activation of T cells normally depends on an antigen-specific signal following contact of the T cell receptor (TCR) with an antigenic peptide presented via the major histocompatibility complex (MHC) while the extent of this reaction is controlled by positive and negative antigen-independent signals eminating from a variety of co-stimulatory molecules. The latter are commonly members of the CD28/B7 family. Conversely, Programmed Death-1 (PD-1) is a member of the CD28 family of receptors that delivers a negative immune response when induced on T cells. Contact between PD-1 and one of its ligands (B7-H1 or B7-DC) induces an inhibitory response that decreases T cell multiplication and/or the strength and/or duration of a T cell response.

Thus, the T lymphocyte response is regulated by various factors, including cell surface molecules that act as receptors, where the latter include both the TCR complex as well as other surface molecules.

In sum, an antigen specific T cell response is mediated by two signals: 1) engagement of the TCR with antigenic peptide presented in the context of HC (signal 1), and 2) a second antigen-independent signal delivered by contact between different receptor/ligand pairs (signal 2). This "second signal" is critical in determining the type of T cell response (activation vs tolerance) as well as the strength and duration of that response, and is regulated by both positive and negative signals from costimulatory molecules, such as the B7 family of proteins.

The most extensively characterized T cell costimulatory pathway is B7-CD28, in which B7-1 (CD80) and B7-2 (CD86) each can engage the stimulatory CD28 receptor and the inhibitory CTLA-4 (CD152) receptor. In conjunction with signaling through the T cell receptor, CD28 ligation increases antigen-specific proliferation of T cells, enhances production of cytokines, stimulates differentiation and effector function, and promotes survival of T cells (Lenshow, et al., *Annu. Rev. Immunol.*, 14:233-258 (1996); Chambers and Allison, *Curr. Opin. Immunol.*, 9:396-404 (1997); and Rathmell and Thompson, *Annu. Rev. Immunol.*, 17:781-828 (1999)). In contrast, signaling through CTLA-4 is thought to deliver a negative signal that inhibits T cell proliferation, IL-2 production, and cell cycle progression (Krummel and Allison, *J. Exp. Med.*, 183:2533-2540 (1996); and Walunas, et al., *J. Exp. Med.*, 183:2541-2550 (1996)). Other members of the B7 family of costimulatory molecules include B7-H1 (Dong, et al, *Nature Med.*, 5:1365-1369 (1999); and Freeman, et al., *J. Exp. Med.*, 192:1-9 (2000)), B7-DC (Tseng, et al., *J. Exp. Med.*, 193:839-846 (2001); and Latchman, et al., *Nature Immunol.*, 2:261-268 (2001)), B7-H2 (Wang, et al., *Blood*, 96:2808-2813 (2000); Swallow, et al., *Immunity*, 11:423-432 (1999); and Yoshinaga, et al., *Nature*, 402:827-832 (1999)), B7-H3 (Chapoval, et al., *Nature Immunol.*, 2:269-274 (2001)) and B7-H4 (Choi, et al., *J. Immunol.*, 171:4650-4654 (2003); Sica, et al., *Immunity*, 18:849-861 (2003); Prasad, et al., *Immunity*, 18:863-873 (2003); and Zang, et al., *Proc. Natl. Acad. Sci. U.S.A.*, 100:10388-10392 (2003)). B7-H5 (described in WO 2006/012232) is a newly discovered member of the B7 family.

B7 family molecules have a membrane proximal IgC (constant) domain and a membrane distal IgV (variable) domain. The CD28-like family of receptors for these ligands share a common extracellular IgV-like domain. Interactions of receptor-ligand pairs are mediated predominantly through residues in the IgV domains of the ligands and receptors (Schwartz, et al., *Nature Immunol.*, 3:427-434 (2002)). In general, IgV domains are described as having two sheets that each contains a layer of β-strands (Williams and Barclay, *Annu. Rev. Immunol.*, 6:381-405 (1988)). The front and back sheets of CTLA-4 contain strands A'GFC'C and ABEDC, respectively (Ostrov, et al., *Science*, 290:816-819 (2000)), whereas the front and back sheets of the B7 IgV domains are composed of strands AGFCC'C" and BED, respectively (Schwartz, et al., *Nature*, 410:604-608 (2001); Stamper, et al., *Nature*, 410:608-611 (2001); and Ikemizu, et al., *Immunity*, 12:51-60 (2000)). Crystallographic analysis revealed that the CTLA-4/B7 binding interface is dominated by the interaction of the CDR3-analogous loop from CTLA-4, composed of a MYPPPY motif, with a surface on B7 formed predominately by the G, F, C, C' and C" strands (Schwartz, et al., *Nature*, 410:604-608 (2001); and Stamper, et al., *Nature*, 410:608-611 (2001)). Data from amino acid homologies, mutation, and computer modeling provide support for the concept that this motif also is a major B7-binding site for CD28 (Bajorath, et al., *J. Mol. Graph. Model.*, 15:135-139 (1997)). Although the MYPPPY motif is not conserved in ICOS, the receptor for B7-H2, studies have indicated that a related motif having the sequence FDPPPF and located at the analogous position is a major determinant for binding of ICOS to B7-H2 (Wand, et al., *J. Exp. Med.*, 195:1033-1041 (2002)).

B7-DC (also called PD-L2 or CD273) is a relatively new member of the B7 family, and has an amino acid sequence that is about 34% identical to B7-H1 (also called PD-L1). Human and mouse B7-DC orthologues share about 70% amino acid identity. While B7-H1 and B7-DC transcripts are found in various tissues (Dong, et al., *Nature Med.*, 5:1365-1369 (1999); Latchman, et al., *Nature Immunol.*, 2:261-268 (2001); and Tamura, *Blood*, 97:1809-1816 (2001)), the expression profiles of the proteins are quite distinct. B7-H1 is broadly expressed on a wide variety of tissue and cell types, while B7-DC expression is predominantly restricted to activated dendritic cells (DC) and macrophages.

It has been shown that both B7-H1 and B7-DC bind to PD-1 (Freeman, et al., *J. Exp. Med.*, 192:1027-1034 (2000)), a distant member of the CD28 family with an immunoreceptor tyrosine-based inhibitory motif (ITIM) in its cytoplasmic domain (Ishida, et al., *EMBO J.*, 11:3887-3895 (1992)). PD-1, a member of the CD28 family of receptors, is inducibly expressed on activated T cells, B cells, natural killer (NK)

cells, monocytes, DC, and macrophages (Keir, et al *Curr. Opin. Immunol.* 19:309-314 (2007)).

The primary result of PD-1 ligation by its ligands is to inhibit signaling downstream of the T cell Receptor (TCR). Therefore, signal transduction via PD-1 usually provides a suppressive or inhibitory signal to the T cell that results in decreased T cell proliferation or other reduction in T cell activation. B7-H1 is the predominant PD-1 ligand causing inhibitory signal transduction in T cells. The present invention solves the problem of undesired T cell inhibition by providing agents that bind to PD-1 and thus prevent inhibitory signal transduction, or else bind to ligands of PD-1 such as B7-H1, thereby preventing the ligand from binding to PD-1 to deliver an inhibitory signal. In either case, T cell responses, such as T cell proliferation or activation, are stimulated.

B7-H1 is the predominant PD-1 ligand, likely due to its broader distribution and higher expression levels. PD-1 inhibition occurs only when PD-1 and TCR are ligated in close proximity to each other, in the context of the immune synapse. PD-1 and its ligands have been the topic of several review articles.

B7-H1 is also over expressed in many cancers (including breast cancer, colon cancer, esophageal cancer, gastric cancer, glioma, leukemia, lung cancer, melanoma, multiple myeloma, ovarian cancer, pancreatic cancer, renal cell carcinoma, and urothelial cancer), and has been linked to poor prognosis. B7-H1 is expressed by many tumor cell lines, especially following stimulation with interferon gamma (IFN-γ), and is also upregulated on tumor infiltrating myeloid derived suppressor cells (MDSC). For example, PD-1 is up-regulated on tumor specific CD8 T cells and is associated with functional impairment, anergy, exhaustion, and apoptosis. PD-1 upregulation has also been associated with dysfunctional and/or suppressive phenotypes on additional cell types, such as regulatory T cells (Treg) and natural killer T (NKT) cells.

The present invention makes use of such molecular functions by providing treatment regimens for treating diseases through increased T cell activity, especially cancer and infectious diseases.

BRIEF SUMMARY OF THE INVENTION

In one aspect, the present invention relates to a method of increasing T cell responses, for example, to an antigen, in a mammal in need of such increase, comprising administering to said mammal a compound that reduces inhibitory signal transduction in immune cells, especially T cells, and a potentiating agent, wherein said treatment regimen is effective to increase the T cell response of said mammal.

Compounds useful in the treatment regimen of the invention include those that bind to and block PD-1 receptors on T cells without triggering inhibitory signal transduction, compounds that bind to PD-1 ligands to prevent their binding to PD-1, compounds that do both and compounds that prevent expression of genes that encode either PD-1 or natural ligands of PD-1. Such compounds are referred to herein as "PD-1 antagonists." Compounds that bind to natural ligands of PD-1 include PD-1 itself, as well as active fragments of PD-1, and in the case of the B7-H1 ligand, B7.1 proteins and fragments. Such antagonists include proteins, antibodies, anti-sense molecules and small organics. In a preferred embodiment, said T cell response is greater than that produced by either of said PD-1 antagonist or said potentiating agent when either is administered without the other.

In another embodiment, compounds useful in the methods of the invention are those that bind to T cell surface molecules such as CTLA4 to prevent the inhibitory signals triggered by binding of natural ligands thereof or that bind to said natural ligands. Such antagonists include proteins, antibodies, anti-sense molecules and small organics.

In a general embodiment, compounds useful in treatment regimens and compositions of the present invention include those that bind to PD-1 without triggering, inducing, increasing, facilitating and/or permitting co-ligation of PD-1 with TCR.

Preferred compounds that prevent inhibitory signal transduction through PD-1 and thus act as PD-1 antagonists include, but are not limited to, B7-DC polypeptides, especially soluble portions of these, including active fragments of these, variants and homologs of these, as well as fusion proteins incorporating any of the foregoing, that bind to PD-1 without triggering inhibitory signal transduction. In preferred embodiments, B7-DC comprises the amino acid sequence of SEQ ID NO: 1, 2, 3 or 4. Preferred such compounds are those incorporating the soluble domain of B7-DC (i.e., without transmembrane sequence). Suitable fragments of B7-DC polypeptides include fragments containing the lgV and/or lgC domains or fragments containing only the IgV domain, with the latter being a preferred embodiment, with amino acids 20-121 of SEQ ID NO: 1 being a preferred example of an IgV domain.

Preferred PD-1 antagonists also include, but are not limited to, active fragments of natural ligands of PD-1, such as 87-H1 polypeptides (disclosed in U.S. Pat. No. 6,803,192, incorporated by reference herein in its entirety), especially soluble portions of these, including variants and homologs of these, as well as fusion proteins incorporating any of the foregoing, that bind to PD-1 without triggering inhibitory signal transduction.

Preferred compounds of the invention also include, but are not limited to, compounds, including active fragments, variants and homologs, that bind to natural ligands of PD-1, such as fragments of B7-1 that bind to B7-H1, as well as fusion proteins incorporating any of the foregoing, that bind to ligands of PD-1 to prevent the latter from binding to PD-1 to trigger inhibitory signal transduction.

In another embodiment, the compositions and methods of use thereof, include a combination of a PD-1 receptor antagonist that binds to and blocks the PD-1 receptor, and a separate PD-1 receptor antagonist that binds to and blocks PD-1 receptor ligands. Another embodiment of the present invention provides PD-1 receptor antagonists that bind to the PD-1 receptor without triggering inhibitory signal transduction through the PD-1 receptor and also have the ability to bind and antagonize PD-1 receptor ligands, such as B7-H1, that would otherwise trigger inhibitory signal transduction through the PD-1 receptor. Other contemplated PD-1 receptor antagonists include bi-specific antibodies that can bind both the PD-1 receptor and PD-1 receptor ligands.

Preferred embodiments of compounds useful in the present invention also include antibodies that bind to PD-1 or CTLA4, thereby reducing, or abolishing, inhibitory signal transduction mediated by these sources.

Preferred compounds for use in the methods of the invention also include, but are not limited to, active fragments of ligands of CTLA4 (such as B7-1 and B7-2) that bind to CTLA4 to reduce subsequent inhibitory signals yet do not bind to CD28 or otherwise inhibit positive signal transduction by CD28.

Preferred compounds that prevent inhibitory signal transduction through PD-1 and thus act as PD-1 antagonists include, but are not limited to, B7-DC antagonists, especially soluble portions of these, including active fragments of these, variants and homologs of these, as well as fusion proteins incorporating any of the foregoing, that bind to B7-DC.

In one embodiment, B7-DC polypeptides, fragments or variants thereof are coupled to other polypeptides to form fusion proteins that antagonize the PD-1 receptor by binding to the PD-1 receptor without causing inhibitory signal transduction through PD-1, thereby reducing, or interfering with, ligand binding to PD-1, particularly B7-H1 binding, and thereby interfering with inhibitory signal transduction through the PD-1 receptor. Examples of such fusion proteins are polypeptides comprising the amino acid sequence of SEQ ID NO: 9, 10, 12 or 13, as well as homologs thereof. In one preferred embodiment, all or a portion of the extracellular domain (ECD) of B7-DC is part of a fusion protein wherein it is linked to a second polypeptide containing an Fc portion of an immunoglobulin. A preferred example of this is B7-DC-Ig, especially where this structure is part of a homodimer wherein two B7-DC-Ig molecules are linked to each other, such as by a disulfide linkage.

In specific embodiments, fragments useful in the compounds of the invention consist of at least 10, 15, 25, 50, 75, 100, 150, 200 or more contiguous amino acids of a polypeptide having the desired antagonist activity. Such fragments are also commonly part of fusion proteins for use in the invention.

In another aspect, the present invention relates to a method of increasing T cell responses in a mammal in need thereof, comprising administering to said mammal an effective treatment regimen comprising an anti-PD-1 antibody and a potentiating agent, wherein said treatment regimen is effective to increase the T cell response of said mammal.

In another aspect, the present invention relates to a method of increasing T cell responses in a mammal in need thereof, comprising administering to said mammal an effective treatment regimen comprising an immunomodulator, and a potentiating agent, wherein said treatment regimen is effective to increase the T cell response of said mammal. Such immunomodulators include molecules that antagonize other CD28 family receptors (such as CTLA4) that inhibit T cell responses. A preferred embodiment uses an anti-CTLA4 antibody and a potentiating agent. Additional immunomodulators include: molecules that agonize CD28 family receptors (such as CD28 and ICOS) that activate T cell responses; molecules that antagonize B7 family ligands (such as B7-H1, B7-DC, B7-H4) that inhibit T cell responses; and molecules that agonize B7 family ligands (such as B7.1 and B7.2) that activate T cell responses.

In additional embodiments of any of the methods of the invention, the treatment regimen of a PD-1 antagonist compound and a potentiating agent further comprises at least one additional therapeutic agent. Additional therapeutic agents contemplated include immunomodulatory agents. Exemplary immunomodulating agents for such methods include anti-PD-1 and anti-CTLA4 antibodies.

In one embodiment, the potentiating agent is selected from cyclophosphamide and analogs of cyclophosphamide, Sunitinib (Sutent), anti-TGFβ and Imatinib (Gleevac), a mitosis inhibitor, such as paclitaxel, an aromatase inhibitor, such as letrozole, an A2a adenosine receptor (A2AR) antagonist, an angiogenesis inhibitor, anthracyclines, oxaliplatin, doxorubicin, TLR4 antagonists, and IL-18 antagonists. Some of these agents reduce the number of Tregs (i.e., regulatory T lymphocytes or T-regs) within the tumor microenvironment.

In another embodiment, the methods and/or compositions of the invention specifically contemplate use of any suitable adjuvant as part of said method and/or composition.

In accordance with the invention, T cells can be contacted with PD-1 receptor antagonist and/or compositions thereof containing a potentiating agent in vitro, ex vivo or in viva. Contacting T cells using PD-1 receptor antagonists and/or compositions thereof containing a potentiating agent can occur before, during or after activation of the T cell.

In a specific embodiment, a molecule that prevents or reduces inhibitory signal transduction through PD-1 and the potentiating agent are administered at different times, such as where the potentiating agent is administered prior to administering the PD-1 antagonist. Such administration may be in conjunction with an additional therapeutic agent.

In specific embodiments of any of the methods of the invention, the treatment regimen includes administration of the potentiating agent at least 1 hour, or at least 2 hours, or at least 3 hours, or at least 5 hours, or at least 10 hours, or at least 15 hours, or at least 20 hours, or at least 24 hours, or at least 30 hours or even longer before administering any or all of the PD-1 antagonist, the anti-PD-1 antibody, the anti-CTLA4 antibody, and/or additional therapeutic agents. Administration of the potentiating agent may also occur after administering any or all of the PD-1 antagonist, the anti-PD-1 antibody, the anti-CTLA4 antibody and/or additional therapeutic agents, such as no more than 1 hour, 2 hours, 3 hours, 5 hours, 10 hours, 15 hours, 20 hours, 24 hours, or even up to 30 hours after administering a PD-1 antagonist, or may occur in conjunction with administering the PD-1 antagonist.

The increased T cell response achieved as a result of the methods of the invention is sufficient to treat a disease, including one or more of cancer, viral infection, bacterial infection and parasitic infection. Where the disease is cancer, such cancer is any one or more of bladder, brain, breast, cervical, colo-rectal, esophageal, kidney, liver, lung, nasopharangeal, pancreatic, prostate, skin, stomach, uterine, ovarian, testicular, or hematologic cancer.

In another aspect, the present invention includes compositions of the antagonists used in the methods of the invention, in a pharmaceutically acceptable carrier and wherein said PD-1 binding molecule and said potentiating agent are each present in an amount effective to produce increased T cell stimulation.

In one preferred embodiment, the invention includes medical kits comprising containers holding one or more of the agents for use in the invention together with pharmaceutical carriers for dilution thereof and instructions for administration. In addition, both of said PD-1 receptor antagonist and potentiating agent may be present as components in a single container, in a pharmaceutically acceptable carrier, when said components are to be administered at the same time.

BRIEF DESCRIPTION OF THE DRAWINGS

FIG. 1 shows that B7-DC-Ig binds to PD-1. Labeled B7-DC-Ig was incubated at various concentrations with a CHO cell line constitutively expressing PD-1 or parent CHO cells that do not express PD-1. Binding was analyzed by flow cytometry. The median fluorescence intensity (MFI) of B7-DC-Ig (y-axis) is shown as a function of the concentration of probe (x-axis). B7-DC-Ig binds to CHO.PD-1 cells (solid circle) but not untransfected CHO cells (gray triangle).

FIG. 2 shows that B7-DC-Ig competes with B7-H1 for binding to PD-1. Unlabeled B7-DC-Ig at various concentrations was first incubated with a CHO cell line constitutively expressing PD-1 before adding labeled B7-H1-Ig to the cell mixture. The median fluorescence intensity (MFI) of B7-H1-Ig (y-axis) is shown as a function of the concentration of unlabeled B7-DC-Ig competitor (x-axis) added. As the concentration of unlabeled B7-DC-Ig is increased the amount of labeled B7-H1-Ig bound to CHO cells decreases, demonstrating that B7-DC-Ig competes with B7-H1 for binding to PD-1.

FIG. 3 shows the results of experiments wherein the combination of cyclophosphamide (CTX or Cytoxane) and dimeric murine B7-DC-Ig resulted in eradication of established CT26 tumors (colon carcinoma) in mice. Graph A shows tumor volume ($mm^3$) versus days post tumor challenge in mice treated with 100 mg/kg of CTX on Day 10 while Graph B shows tumor volume ($mm^3$) versus days post tumor challenge in mice treated with CTX on Day 10 followed a day later by the first B7-DC-Ig administration. Each line in each graph represents one mouse. Black arrow stands for B7-DC-Ig administration. Graph C shows average tumor volume.

FIG. 4 shows the results of experiments wherein the combination of CTX and dimeric murine B7-DC-Ig eradicated established CT26 tumors (colon carcinoma) in mice and protected against re-challenge with CT26. Mice that were treated with CTX and B7-DC-Ig and found to be free of tumor growth on day 44 following tumor inoculation were rechallenged with tumors. The mice were later rechallenged again on on Day 70. None of the mice displayed tumor growth by day 100.

FIG. 5 shows CTX and B7-DC-Ig treatment resulted in generation of tumor specific memory CTL. Mice eradicated established CT26 subcutenous tumors post CTX and B7-DC-Ig treatment were re-challenged with CT26 cells. Seven days later, splenocytes were isolated and pulsed with either ovalbumin, an irrelevant peptide, or AH1, a CT26 specific peptide. Cells were stained with anti-CD8 antibody first followed by intracellular staining with anti-IFNγ antibody prior to FACS analysis.

FIG. 6 shows the effects of different doses of B7-DC-Ig in combination with CTX on the eradication of established CT26 tumors in mice. Balb/C mice at age of 9 to 11 weeks were implanted subcutaneously with 1E05 CT26 cells. On Day 9, mice were injected IP with 100 mg/kg of CTX. Twenty four hours later, on Day 10, mice were treated with 30, 100, or 300 ug of B7-DC-Ig followed by 2 injections every week up to total 8 treatments. Tumor growth was measured two times per week.

FIG. 7 shows the results of experiments wherein the combination of CTX and anti-PD-1 antibody resulted in eradication of established CT26 tumors (colon carcinoma) in mice. Graph A shows tumor volume ($mm^3$) versus days post tumor challenge in untreated mice (i.e., mice treated with vehicle alone), Graph B shows tumor volume ($mm^3$) versus days post tumor challenge in mice treated with anti-PD-1 alone starting on Day 11 at 300 µg per injection, 3 times per week, up to 12 injections and Graph C shows tumor volume ($mm^3$) versus days post tumor challenge in mice treated with CTX on Day 11 and the first anti-PD-1 administration on Day 12 at 300 µg per injection, 3 times per week, up to 12 injections. Each line in each graph represents one mouse. Black arrow stands for anti-PD-1 administration.

FIG. 8 shows the results of experiments wherein the combination of CTX and anti-CTLA4 antibody resulted in eradication of established CT26 tumors (colon carcinoma) in mice. Here, Graph A shows tumor volume ($mm^3$) versus days post tumor challenge in mice treated with 100 mg/kg of CTX on Day 11 while Graph B shows tumor volume ($mm^3$) versus days post tumor challenge in mice treated with CTX on Day 11 and anti-CTLA4 on Day 12 at 100 µg per injection, 2 times per week, up to 8 injections. Each line in each graph represents one mouse. Black arrow stands for anti-CTLA-4 administration.

FIG. 9 shows the results of experiments wherein Balb/C mice at age of 9 to 11 weeks of age were implanted with 1×10⁵ CT26 cells subcutaneously. On Day 9, mice were injected with 100 mg/kg of CTX, IP. Twenty four hours later, on Day 10, mice were treated with 100 ug of B7-DC-Ig. There were 5 groups: naïve mice that did not receive any tumor cells, vehicle injected, CTX alone, CTX+B7-DC-Ig or B7-DC-Ig alone. Two naïve mice and 4 mice from other groups were removed from the study on Day 11 (2 days post CTX) and Day 16 (7 days post CTX) for T cell analysis. Left panel shows on Day 11, 2 days post CTX injection, Treg in the spleen of the mice with CTX treatment was significantly lower than the one in the mice with tumor implantation and injected with vehicle. Right panel shows that on Day 16, 7 days post CTX and 6 days post B7-DC-Ig treatment, B7-DC-Ig significantly lowered the CD4+ T cells expressing high PD-1. This was observed in both the B7-DC-Ig treated and CTX+B7-DC-Ig treated mice. Mice implanted with tumor cells intended to have more PD-1+/CD4+ T cells in the draining LN compared with naïve mice.

FIG. 10 shows the results of experiments wherein the combination of CTX and B7-DC-Ig resulted in increased survival in mice with tail vein injection of a mouse prostate tumor cell line. SP-1 cells were isolated from mouse lungs that were metastasized from TRAMP prostate tumor cell injection. B10.D2 mice were first injected with $3\times10^5$ SP-1 cells via tail vein injection. On Day 5, 12 and 19, mice were injected with 50 mg/kg of CTX where was indicated. On Day 6, 13 and 20, mice were administered with 5 mg/kg of B7-DC-Ig were it was indicated. Here, "NT" refers to "not treated".

FIG. 11. Balb/C mice at age of 11-13 weeks were given isolated hepatic metastases using a hemispleen injection technique. The spleens of anesthetized mice were divided into two halves and the halves were clipped. CT26 cells (1E05) were injected into one hemispleen, and after 30 seconds, that hemispleen was resected and the splenic draining vein was clipped. On Day 10, mice received 1 injection of CTX at 50 mg/kg, IP. Twenty four hours later, on Day 11, mice were treated with recombinant *Listeria* carrying AH1 peptide, an immunodominant epitope of CT26, at $0.1\times LD_{50}$ ($1\times10^7$ CFU), then on Day 14 and 17. Mice were also treated with B7-DC-Ig on Day 11 and then on Day 18. Mouse overall survival was monitored.

DEFINITIONS

Unless defined otherwise, all technical and scientific terms used herein have the same meanings as commonly understood by one of skill in the art to which the disclosed invention belongs. In particular, the following terms and phrases have the following meaning.

The term "inhibitory signal transduction" is intended to mean any signal transduction having the effect of abolishing, or otherwise reducing, T cell responses against an antigen, whether by reducing T cell proliferation or by any other inhibitory mechanism, whereby the extent or duration of an immunogenic T cell response is decreased. Such inhibitory signal transduction may be due to PD-1 binding to a natural ligand, such as binding of PD-1 by B7-H1 or some other member of this class of ligands, B7-DC, or may be due to binding of CTLA4 to ligands, such as B7-1 or B7-2. In general, compounds of the invention reduce such inhibitory signal transduction and include, but are not limited to, PD-1 antagonists and CTLA4 antagonists.

The term "PD-1 antagonist" means any molecule that attenuates inhibitory signal transduction mediated by PD-1, found on the surface of T cells, B cells, natural killer (NK) cells, monocytes, DC, and macrophages. Such an antagonist includes a molecule that disrupts any inhibitory signal generated by a PD-1 molecule on a T cell. In specific examples of the invention, a PD-1 antagonist is a molecule that inhibits, reduces, abolishes or otherwise reduces inhibitory signal transduction through the PD-1 receptor signaling pathway. Such decrease may result where: (i) the PD-1 antagonist of the invention binds to a PD-1 receptor without triggering signal transduction, to reduce or block inhibitory signal transduction; (ii) the PD-1 antagonist binds to a ligand (e.g. an agonist) of the PD-1 receptor, preventing its binding thereto (for example, where said agonist is B7-H1); (iii) the PD-1 antagonist binds to, or otherwise inhibits the activity of, a molecule that is part of a regulatory chain that, when not inhibited, has the result of stimulating or otherwise facilitating PD-1 inhibitory signal transduction; or (iv) the PD-1 antagonist inhibits expression of a PD-1 receptor or expression ligand thereof, especially by reducing or abolishing expression of one or more genes encoding PD-1 or one or more of its natural ligands. Thus, a PD-1 antagonist of the invention is a molecule that effects a decrease in PD-1 inhibitory signal transduction, thereby increasing T cell response to one or more antigens.

As used herein, the term "CTLA4 antagonist" means a compound that reduces CTLA4-mediated inhibition of T cell reactions. For example, in an T cell, CTLA4 delivers an inhibitory impulse upon binding of B7 ligands, such B7-1 and B7-2. A CTLA4 antagonist is one that disrupts binding of said ligands to CTLA4 on activated T cells. In one embodiment, the antagonist is an anti-CTLA4 antibody that binds CTLA4 to prevent ligand binding.

As used herein, the term "active fragment" refers to a portion of a natural polypeptide, or a polypeptide with high sequence homology (for example, at least 80%, 85%, 90%, 95%, 98%, or 99% amino acid sequence identity) to a natural polypeptide and that exhibits PD-1 antagonist activity, for example, by binding PD-1 or by binding to a ligand of PD-1. In preferred embodiments, such a fragment would consist of the extracellular domain (ECD) of a B7-DC protein that binds to PD-1, such as SEQ ID NO: 3, preferably amino acids 20 to 221 thereof. In the case of PD-1 polypeptide, an active fragment would be a portion of said polypeptide comprising a binding domain that binds to a natural ligand of PD-1 to prevent stimulation of PD-1 mediated inhibitory signal transduction by said ligand. Active fragments may be identified by their ability to compete with the molecule they are derived from for binding to a natural binding site. For example, active fragments will compete with wild-type B7-DC for binding to PD-1.

With respect to an antibody, the term "active fragment" means an antigen binding portion of an antibody that is less than an entire immunoglobulin. Such fragments include Fab and F(ab$_2$)' fragments, capable of reacting with and binding to any of the polypeptides disclosed herein as being receptors or ligands. These Fab and F(ab)$_2$ fragments lack the Fc portion of an intact antibody, clear more rapidly from the circulation, and may have less non-specific tissue binding than an intact antibody (Wahl et al., *J. Nuc. Med.* 24:316-325 (1983)). Also included are Fv fragments (Hochman, J. et al. (1973) *Biochemistry* 12:1130-1135; Sharon, J. et al. (1976) *Biochemistry* 15:1591-1594). These various fragments are produced using conventional techniques such as protease cleavage or chemical cleavage (see, e.g., Rousseaux et al., *Meth. Enzymol.,* 121:663-69 (1986)).

As used herein, the term "soluble portion" of a PD-1 antagonist means that portion of the full length polypeptide that does not include any part of the transmembrane portion or segment. For example, with respect to B7-DC, a soluble portion would include the extracellular portion (with or without the N-terminal signal sequence) but would not include any part of the transmembrane portion (or, at least, not enough to reduce solubility). Thus, the ECD of human B7-DC is shown as SEQ ID NO: 3 and consists of both the IgV-like and IgC-like domains of the full length molecule (i.e., amino acids 20-221 of the full length sequence (SEQ ID NO: 1).

As used herein, a "co-stimulatory polypeptide" is a polypeptide that, upon interaction with a cell-surface molecule on T cells, modulates the activity of the T cell. Thus, the response of the T cell can be an effector (e.g., CTL or antibody-producing B cell) response, a helper response providing help for one or more effector (e.g., CTL or antibody-producing B cell) responses, or a suppressive response.

As used herein, the term "treatment regimen" refers to a treatment of a disease or a method for achieving a desired physiological change, such as increased or decreased response of the immune system to an antigen or immunogen, such as an increase or decrease in the number or activity of one or more cells, or cell types, that are involved in such response, wherein said treatment or method comprises administering to an animal, such as a mammal, especially a human being, a sufficient amount of two or more chemical agents or components of said regimen to effectively treat a disease or to produce said physiological change, wherein said chemical agents or components are administered together, such as part of the same composition, or administered separately and independently at the same time or at different times (i.e., administration of each agent or component is separated by a finite period of time from one or more of the agents or components) and where administration of said one or more agents or components achieves a result greater than that of any of said agents or components when administered alone or in isolation.

As used herein the term "isolated" is meant to describe a compound of interest (e.g., either a polynucleotide or a polypeptide) that is in an environment different from that in which the compound naturally occurs e.g. separated from its natural milieu such as by concentrating a peptide to a concentration at which it is not found in nature. "Isolated" is meant to include compounds that are within samples that are substantially enriched for the compound of interest and/or in which the compound of interest is partially or substantially purified.

As used herein, the term "polypeptide" refers to a chain of amino acids of any length, regardless of modification (e.g., phosphorylation or glycosylation). A polypeptide of the present invention may be a recombinant polypeptide, a natural polypeptide or a synthetic polypeptide, preferably a recombinant polypeptide.

As used herein, a "variant" polypeptide contains at least one amino acid sequence alteration as compared to the amino acid sequence of the corresponding wild-type polypeptide.

As used herein, an "amino acid sequence alteration" can be, for example, a substitution, a deletion, or an insertion of one or more amino acids.

As used herein, the terms "portion," "segment," and "fragment," when used in relation to polypeptides, refer to a continuous sequence of residues, such as amino acid residues, which sequence forms a subset of a larger sequence. For example, if a polypeptide were subjected to treatment with any of the common endopeptidases, such as trypsin or chymotrypsin, the oligopeptides resulting from such treatment would represent portions, segments or fragments of the starting polypeptide. A "fragment" of a polypeptide thus refers to any subset of the polypeptide that is a shorter polypeptide of the full length protein. Generally, fragments will be five or more amino acids in length.

A derivative, analog or homolog, of a polypeptide (or fragment thereof) of the invention may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such derivatives and analogs are deemed to be within the scope of those skilled in the art from the teachings herein.

As used herein, "valency" refers to the number of binding sites available per molecule.

In accordance with the present invention, the term "percent identity" or "percent identical," when referring to a sequence, means that a sequence is compared to a claimed or described sequence after alignment of the sequence to be compared (the "Compared Sequence") with the described or claimed sequence (the "Reference Sequence"). The Percent Identity is then determined according to the following formula;

$$\text{Percent Identity} = 100[1 - (C/R)]$$

wherein C is the number of differences between the Reference Sequence and the Compared Sequence over the length of alignment between the Reference Sequence and the Compared Sequence wherein (I) each base or amino acid in the Reference Sequence that does not have a corresponding aligned base or amino acid in the Compared Sequence and (ii) each gap in the Reference Sequence and (iii) each aligned base or amino acid in the Reference Sequence that is different from an aligned base or amino acid in the Compared Sequence, constitutes a difference; and R is the number of bases or amino acids in the Reference Sequence over the length of the alignment with the Compared Sequence with any gap created in the Reference Sequence also being counted as a base or amino acid. If an alignment exists between the Compared Sequence and the Reference Sequence for which the percent identity as calculated above is about equal to or greater than a specified minimum Percent Identity then the Compared Sequence has the specified minimum percent identity to the Reference Sequence even though alignments may exist in which the hereinabove calculated Percent Identity is less than the specified Percent Identity.

As used herein, the term "conservative amino acid substitution" means a substitution wherein the substituted amino acid has similar structural or chemical properties, and "non-conservative" amino acid substitutions are those in which the charge, hydrophobicity, or bulk of the substituted amino acid is significantly altered. Non-conservative substitutions will differ more significantly in their effect on maintaining (a) the structure of the peptide backbone in the area of the substitution, for example, as a sheet or helical conformation, (b) the charge or hydrophobicity of the molecule at the target site, or (c) the bulk of the side chain. Examples of conservative amino acid substitutions include those in which the substitution is within one of the five following groups: 1) small aliphatic, nonpolar or slightly polar residues (Ala, Ser, Thr, Pro, Gly); 2) polar, negatively charged residues and their amides (Asp, Asn, Glu, Gln); polar, positively charged residues (His, Arg, Lys); large aliphatic, nonpolar residues (Met, Leu, Ile, Val, Cys); and large aromatic resides (Phe, Tyr, Trp). Examples of non-conservative amino acid substitutions are those where 1) a hydrophilic residue, e.g., seryl or threonyl, is substituted for (or by) a hydrophobic residue, e.g., leucyl, isoleucyl, phenylalanyl, valyl, or alanyl; 2) a cysteine or proline is substituted for (or by) any other residue; 3) a residue having an electropositive side chain, e.g., lysyl, arginyl, or histidyl, is substituted for (or by) an electronegative residue, e.g., glutamyl or aspartyl; or 4) a residue having a bulky side chain, e.g., phenylalanine, is substituted for (or by) a residue that does not have a side chain, e.g., glycine.

The terms "individual", "host", "subject", and "patient" are used interchangeably herein, and refer to a mammal, including, but not limited to, primates, for example, human beings, as well as rodents, such as mice and rats, and other laboratory animals.

As used herein the term "effective amount" or "therapeutically effective amount" means a dosage sufficient to treat, inhibit, or alleviate one or more symptoms of a disease state being treated or to otherwise provide a desired pharmacologic and/or physiologic effect, especially enhancing T cell response to a selected antigen. The precise dosage will vary according to a variety of factors such as subject-dependent variables (e.g., age, immune system health, etc.), the disease, and the treatment being administered.

As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

The term "antibody" is meant to include both intact molecules as well as fragments thereof that include the antigen-binding site. Whole antibody structure is often given as $H_2L_2$ and refers to the fact that antibodies commonly comprise 2 light (L) amino acid chains and 2 heavy (H) amino acid chains. Both chains have regions capable of interacting with a structurally complementary antigenic target. The regions interacting with the target are referred to as "variable" or "V" regions and are characterized by differences in amino acid sequence from antibodies of different antigenic specificity. The variable regions of either H or L chains contains the amino acid sequences capable of specifically binding to antigenic targets. Within these sequences are smaller sequences dubbed "hypervariable" because of their extreme variability between antibodies of differing specificity. Such hypervariable regions are also referred to as "complementarity determining regions" or "CDR" regions. These CDR regions account for the basic specificity of the antibody for a particular antigenic determinant structure. The CDRs represent non-contiguous stretches of amino acids within the variable regions but, regardless of species, the positional locations of these critical amino acid sequences within the variable heavy and light chain regions have been found to have similar locations within the amino acid sequences of the variable chains. The variable heavy and light chains of all antibodies each have 3 CDR regions, each non-contiguous with the others (termed L1, L2, L3, H1, H2, H3) for the respective light (L) and heavy (H) chains. The accepted CDR regions have been described by Kabat et al, *J. Biol. Chem.* 252:6609-6616 (1977). The antibodies disclosed according to the invention may also be wholly synthetic, wherein the polypeptide chains of the antibodies are synthesized and, possibly, optimized for binding to the polypeptides disclosed herein as being receptors. Such antibodies may be chimeric or humanized antibodies and may be fully tetrameric in structure, or may be dimeric and comprise only a single heavy and a single light chain.

DETAILED DESCRIPTION OF THE INVENTION

The present invention provides a treatment regimen, or combination therapy, for treating disease in mammals comprising a compound that reduces or abolishes inhibitory signal transduction in T cells, preferably human T cells, administered in conjunction with a potentiating agent to increase an immune response.

The methods of the invention also relate to the use of broad spectrum immunomodulators and compositions of these. In general, the increased T cell response resulting from these methods is greater than any increased T cell response resulting from administering the same dose of either of said PD-1 antagonist or said potentiating agent alone.

The disclosed compositions and regimens are useful to stimulate or enhance immune responses involving T cells. Thus, the methods of the invention are most useful in treating a disease condition that would benefit from an increase in T cell activity and where the increased T cell response is necessary or sufficient to treat said disease, even though the disease is not specifically caused or aggravated by a reduced T cell response. In a preferred embodiment, the type of disease to be treated or prevented is a malignant tumor or a chronic infectious disease caused by a bacterium, virus, protozoan, helminth, or other intracellular microbial pathogen that is attacked, i.e., by cytotoxic T lymphocytes. Activation of T cells using the disclosed compositions is also advantageous to treat or prevent conditions characterized by immunosuppression.

In accordance with the present invention, the T cell response can be regulated by molecules that bind to receptors on the T cell surface and molecules that bind to ligands of such receptors. In the case of PD-1, molecules that bind PD-1 to reduce its inhibitory effect and/or molecules that bind one or more PD-1 ligands to reduce their ability to bind PD-1 have the effect of reducing the ability of PD-1 to inhibit T cell response, thereby increasing this response and the immunological effects thereof.

A. PD-1 Receptor Antagonists

Compositions containing antagonists of PD-1 receptors are provided and include compounds or agents that either bind to and block a ligand of PD-1 to interfere with or inhibit the binding of the ligand to the PD-1 receptor, or bind directly to and block the PD-1 receptor without inducing inhibitory signal transduction through the PD-1 receptor. In another embodiment, the PD-1 receptor antagonist binds directly to the PD-1 receptor without triggering inhibitory signal transduction and also binds to a ligand of the PD-1 receptor to reduce or inhibit the ligand from triggering signal transduction through the PD-1 receptor. By reducing the number and/or amount of ligands that bind to PD-1 receptor and trigger the transduction of an inhibitory signal, fewer cells are attenuated by the negative signal delivered by PD-1 signal transduction and a more robust immune response can be achieved.

In accordance with the present invention, PD-1 signaling requires binding to a PD-1 ligand (such as B7-H1 or B7-DC) in close proximity to a peptide antigen presented by major histocompatibility complex (MHC) (see, for example, Freeman *Proc. Natl. Acad. Sci. U.S.A* 105:10275-10276 (2008)). Therefore, proteins, antibodies or small molecules that prevent co-ligation of PD-1 and TCR on the T cell membrane are useful PD-1 antagonists contemplated by this invention.

Exemplary PD-1 receptor antagonists include, but are not limited to B7-DC polypeptides, including homologs and variants of these, as well as active fragments of any of the foregoing, and fusion proteins that incorporate any of these. In a preferred embodiment, the fusion protein comprises the soluble portion of B7-DC coupled to the Fc portion of an antibody, such as human IgG, and does not incorporate all or part of the transmembrane portion of human B7-DC. The PD-1 receptor antagonists can also be small molecule antagonists or antibodies that reduce or interfere with PD-1 receptor signal transduction by binding to ligands of PD-1 or to PD-1 itself, especially where co-ligation of PD-1 with TCR does not follow such binding, thereby not triggering inhibitory signal transduction through the PD-1 receptor.

The PD-1 receptor antagonists provided herein are generally useful in vivo and ex vivo as immune response-stimulating therapeutics. In general, the disclosed antagonist compositions are useful for treating a subject having or being predisposed to any disease or disorder to which the subject's immune system mounts an immune response.

1. B7-DC Polypeptides

In certain embodiments, B7-DC proteins can be used as PD-1 receptor antagonists. B7-DC is a natural ligand of PD-1 and binds to PD-1 with higher affinity than B7-H1, and can thus inhibit B7-H1:PD-1 interactions. Suitable B7-DC polypeptides, including variants, homologs and fragments thereof, can be obtained from the following full length human B7-DC polypeptides with (SEQ ID NO:1) or without (SEQ ID NO:2) the endogenous signal peptide.

```
                                                              (SEQ ID NO: 1)
        MIFLLLMLSL ELQLHQIAAL FTVTVPKELY IIEHGSNVTL ECNFDTGSHV NLGAITASLQ    60

KVENDTSPHR ERATLLEEQL PLGKASFHIP QVQVRDEGQY QCIIIYGVAW DYKYLTLKVK   120

ASYRKINTHI LKVPETDEVE LTCQATGYPL AEVSWPNVSV PANTSHSRTP EGLYQVTSVL   180

RLKPPPGRNF SCVFWNTHVR ELTLASIDLQ SQMEPRTHPT WLLHIFIPFC IIAFIFIATV   240

IALRKQLCQK LYSSKDTTKR PVTTTKREVN SAI                                273

(SEQ ID NO: 2)
        LFTVTVPKEL YIIEHGSNVT LECNFDTGSH VNLGAITASL QKVENDTSPH RERATLLEEQ    60

LPLGKASFHI PQVQVRDEGQ YQCIIIYGVA WDYKYLTLKV KASYRKINTH ILKVPETDEV   120
```

```
                                                     -continued
ELTCQATGYP LAEVSWPNVS VPANTSHSRT PEGLYQVTSV LRLKPPPGRN FSCVFWNTHV  180

RELTLASIDL QSQMEPRTHP TWLLHIFIPF CITAFIFIAT VIALRKQLCQ KLYSSKDTTK  240

RPVTTTKREV NSAI                                                   254
```

The B7 family of molecules, including B7-DC, are expressed at the cell surface with a membrane proximal constant IgC domain and a membrane distal IgV domain. Receptors for these ligands share a common extracellular IgV-like domain. Interactions of receptor-ligand pairs are mediated predominantly through residues in the IgV domains of the ligands and receptors. In general, IgV domains are described as having two sheets that each contains a layer of 3-strands. These β-strands are referred to as A', B, C, C', C", D, E, F and G. The structure of such polypeptides has been described in the literature (See Molnar et al., Crystal structure of the complex between programmed death-1 (PD-1) and its ligand PD-L2, PNAS, Vol. 105, pp. 10483-10488 (29 Jul. 2008)).

B7-DC, a transmembrane protein, in its monomeric form, comprises IgV and IgC domains that make up the extracellular portion of the molecule (the extracellular domain, or ECD), with the IgV-like domain being responsible, in whole or in part, for PD-1 binding as well as other functions recited in the methods of the invention. For the human protein, the IgV domain is characterized in that it possesses a disulfide bond linking the B and F strands (referred to above), which appears to be characteristic of many IgV domains and possesses a similar three-dimensional structure with the IgV domains of both B7-1 and B7-2 (see Molnar et al. (2008), supra).

In one embodiment the B7-DC variant polypeptides contain amino acid alterations (i.e., substitutions, deletions or insertions) within one or more of these β-strands in any possible combination. In another embodiment, B7-DC variants contain one or more amino acid alterations (i.e., substitutions, deletions or insertions) within the A', C, C', C", D, E, F or G β-strands. In a preferred embodiment B7-DC variants contain one or more amino acid alterations in the G β-strand. In another embodiment, variant B7-DC polypeptide fragments include the IgC and IgV domains of B7-DC. In another embodiment, variant B7-DC polypeptide fragments include the IgV domain of B7-DC.

Human and mouse B7-DC proteins contain a short intracytoplasmic domain, a single transmembrane domain and an extracellular domain. The extracellular domain contains two Ig domains; a membrane proximal IgC domain and a membrane distal IgV domain. Useful fragments of variant B7-DC polypeptides include soluble fragments. Soluble B7-DC fragments are fragments of B7-DC that may be shed, secreted or otherwise extracted from the producing cells. In one embodiment, variant B7-DC polypeptide fragments include the entire extracellular domain of B7-DC. The extracellular domain of B7-DC includes amino acids from about 20 to about amino acid 221 of murine or human B7-DC or active fragments thereof. In another embodiment, variant B7-DC polypeptide fragments include the IgC and IgV domains of B7-DC. In another embodiment, variant B7-DC polypeptide fragments include the IgV domain of B7-DC.

PD-1 signaling is thought to require binding to a PD-1 ligand (typically B7-H1) in close proximity to a peptide antigen presented by major histocompatibility complex (MHC) (Freeman Proc. Natl. Acad. Sci. U.S. A 105:10275-10276 (2008)). Therefore, proteins, antibodies or small molecules that prevent co-ligation of PD-1 and TCR on the T cell membrane are useful PD-1 antagonists contemplated by this invention.

The PD-1 antagonist useful in the methods and compositions of the invention include fragments of the B7-DC protein incorporating the ECD. Alternatively, the fragments of B7-DC include part of the extracellular domain that comprise the an IgV or IgV-like domain, preferably amino acids 20-221, more preferably 20-121, that are sufficient to bind to the PD-1 receptor to interfere with, or prevent, or otherwise reduce inhibitory signal transduction through the PD-1 receptor. In a preferred embodiment the B7-DC fragment competes with B7-H1 for binding to PD-1 receptors.

In one embodiment, variant B7-DC polypeptide fragments may contain a region of the polypeptide that is important for binding to PD-1. These polypeptide fragments may be useful to compete for binding to PD-1 and to prevent native B7-DC from binding to PD-1. By competing for binding to PD-1, these fragments may be useful to enhance an immune response, as inhibiting interactions of B7-H1 and B7-DC with PD-1 inhibits the suppression of immune responses that would otherwise occur. A polypeptide fragment of mouse or human B7-DC that could competitively bind to PD-1 can contain, for example, amino acids 101-108 or 110-114. The binding of wild-type B7-DC to PD-1 typically is inhibited by at least 50 percent, 60 percent, 70 percent, 75 percent, 80 percent, 90 percent, 95 percent, or more than 95 percent as compared to the level of binding of wild-type B7-DC to PD-1 in the absence of a fragment of said wild-type B7-DC. Exemplary B7-DC fragments useful in the methods and/or compositions of the invention include, but are in no way limited to, the following B7-DC extracellular domains:

```
Human B7-DC extracellular domain (ECD):
                                                              (SEQ ID NO: 3)
           LFTVTVPKEL YIIEHGSNVT LECNFDTGSH VNLGAITASL QKVENDTSPH RERATLLEEQ   60

LPLGKASFHI PQVQVRDEGQ YQCIIIYGVA WDYKYLTLKV KASYRKINTH ILKVPETDEV  120

ELTCQATGYP LAEVSWPNVS VPANTSHSRT PEGLYQVTSV LRLKPPPGRN FSCVFWNTHV  180

RELTLASIDL QSQMEPRTHP TW                                           202
           and murine B7-DC ECD:
                                                              (SEQ ID NO: 4)
           LFTVTAPKEV YTVDVGSSVS LECDFDRREC TELEGIRASL QKVENDTSLQ SERATLLEEQ   60

LPLGKALFHI PSVQVRDSGQ YRCLVICGAA WDYKYLTVKV KASYMRIDTR ILEVPGTGEV  120
```

-continued

```
QLTCQARGYP LAEVSWQNVS VPANTSHIRT PEGLYQVTSV LRLKPQPSRN FSCMFWNAHM  180

KELTSAIIDP LSRMEPKVPR TW                                          202

Cynomolgus monkey B7-DC ECD:
                                                        (Seq ID NO: 15)
LFTVTVPKEL YIIEHGSNVT LECNFDTGSH VNLGAITASL QKVENDTSPH RERATLLEEQ   60

LPLGKASFHI PQVQVRDEGQ YQCIIIYGVA WDYKYLTLKV KASYRKINTH ILKVPETDEV  120

ELTCQATGYP LAEVSWPNVS VPANTSHSRT PEGLYQVTSV LRLKPPPGRN FSCVFWNTHV  180

RELTLASIDL QSQMEPRTHP TW                                          202
```

Numerous other primate sequences useful in the methods and compositions of the invention are provided in Onlamoon et al., Immunology, Vol. 124, pp. 277-293 (2008).

A PD-1 antagonist useful in the compositions and methods of the invention also includes a fusion protein (as described below) that comprises first and second polypeptide portions, wherein said fusion protein, or at least the first polypeptide portion thereof, possesses PD-1 antagonist activity, especially where said fusion protein binds to and blocks PD-1 or binds to and blocks a ligand of PD-1. The first polypeptide portion of such fusion protein can comprise, or consist of, any of the PD-1 antagonistic polypeptides, or PD-1 binding fragments thereof, otherwise recited herein for use as PD-1 antagonists in the methods of the invention. In a preferred embodiment of such a fusion protein, the recited first polypeptide portion is N-terminal to the recited second polypeptide portion. In a separate embodiment, the recited first polypeptide portion is linked to the recited second polypeptide portion by an oligopeptide in addition to the amino acids composing the recited first and second polypeptide portions, where said linking amino acids do not substantially decrease the PD-1 antagonist activity of said fusion protein.

In a preferred dimeric fusion protein, the dimer results from the covalent bonding of Cys residues in the CH regions of two of the Ig heavy chains that are the same Cys residues that are disulfide linked in dimerized normal Ig heavy chains.

A large number of polypeptide sequences that are routinely used as fusion protein binding partners are well known in the art. Examples of useful polypeptide binding partners include, but are not limited to, green fluorescent protein (GFP), glutathione S-transferase (GST), polyhistidine, myc, hemagluttinin, Flag™ tag (Kodak, New Haven, Conn.), maltose E binding protein and protein A.

Still another embodiment provides a tetramer construct having a BirA substrate fused to the extracellular domain of a variant B7-DC polypeptide. Methods for making tetramer constructs are known in the art (see Pertovas, et al., *J. Exp. Med.*, 203:2281 (2006)).

Exemplary murine B7-DC fusion proteins contain amino acids 20-221 of murine B7-DC fused to amino acids 237-469 of murine IgG2a (CAA49868). In one non-limiting example, human B7-DC fusion proteins contain amino acids 20-221 of human B7-DC fused to amino acids 245-476 of human IgG1 (AAA02914). The signal peptides for B7-DC fusion proteins include the endogenous signal peptides or any other signal peptide that facilitates secretion of the fusion protein from a host. In another embodiment, the first polypeptide would include only the IgV domain. Other embodiments may comprise the hinge and Fc domain of an IgG antibody, such IgG1, with none of the variable region present. Other embodiments include use of the hinge and Fc region of IgG2 or IgG4, especially having an N297Q or other mutation that reduces effector function.

In accordance with the methods and compositions of the invention, the polypeptide useful as a PD-1 antagonist, or the first polypeptide portion of a fusion protein useful as a PD-1 antagonist, comprises an amino acid sequence that has at least 60%, or at least 65%, or at least 70%, or at least 75%, or at least 80%, or at least 85%, or at least 90%, or at least 95%, or at least 99%, identity to amino acids 1-221 of SEQ ID NO: 1, preferably amino acids 20-221 of SEQ ID NO: 1, or amino acids 26-221 of SEQ ID NO: 1, or amino acids 1-202 of SEQ ID NO: 3 or 4, more preferably amino acids 20-121 of SEQ ID NO: 1 or amino acids 1-102 of SEQ ID NO: 3 or 4.

In one embodiment, a polypeptide useful as a PD-1 antagonist, or the first polypeptide portion of a fusion protein useful as a PD-1 antagonist, consists of amino acids 1-221 of SEQ ID NO: 1, or consists of amino acids 20-221 of SEQ ID NO: 1, or consists of amino acids 26-221 of SEQ ID NO: 1, or consists of amino acids 1-202 of SEQ ID NO: 3 or 4. In one embodiment (SEQ ID NO: 2), it does not comprise amino acids 1-19 of SEQ ID NO: 1.

In other specific examples, a PD-1 antagonist polypeptide, or first polypeptide portion of a PD-1 antagonist fusion protein, comprises the amino acid sequence 20-121 of SEQ ID NO: 1, preferably where it comprises the amino acid sequence WDYKY at residues 110-114 thereof, or where it comprises amino acids 1-102 of SEQ ID NO: 3, preferably where it comprises the amino acid sequence WDYKY at residues 91-95 thereof.

In a preferred embodiment, such percent identities are achieved by reliance on conservative amino acid substitutions as defined elsewhere herein.

In one such embodiment, the PD-1 antagonist polypeptide, or first polypeptide portion of a PD-1 antagonist fusion protein, does not comprise amino acids 1-19 of SEQ ID NO: 1, or does not comprise any portion of a transmembrane domain, especially not the entire such domain, or does not comprise any portion of the intracellular (or soluble) domain, especially not the entire such domain, of a PD-1 ligand or other PD-1 antagonist protein. In a preferred embodiment, such antagonist, or first polypeptide portion, comprises only the extracellular domain (ECD) of SEQ ID NO:1 and is thus comprised only of a soluble portion of the polypeptide of said sequence, or a fragment of said soluble portion.

In other such embodiments, the PD-1 antagonist polypeptide, or first polypeptide portion of a PD-1 antagonist fusion protein, comprises the IgV domain, or IgV-like domain, or PD-1 binding fragment thereof, of a PD-1 ligand, or consists of the IgV domain, or IgV-like domain, or PD-1 binding fragment thereof, of a PD-1 ligand. In specific examples, such PD-1 ligand is a wild-type B7-DC or B7-H1 molecule, preferably mouse or primate, preferably human, wild-type B7-DC or B7-H1 molecule.

In other such embodiments, the PD-1 antagonist polypeptide, or first polypeptide portion of a PD-1 antagonist fusion protein, a PD-1 binding fragment of the IgV domain, or IgV-like domain, of a PD-1 ligand, especially where IgV domain, or IgV-like domain, consists of amino acids 20-121 of SEQ ID NO: 1 or amino acids 1-102 of SEQ ID NO: 3.

A PD-1 antagonist of the invention also includes a PD-1 binding fragment of amino acids 20-121 of SEQ ID NO: 1

(human full length), or amino acids 1-102 of SEQ ID NO: 3 (extracellular domain or ECD).

In specific embodiments thereof, the polypeptide or PD-1 binding fragment also incorporates amino acids WDYKY at residues 110-114 of SEQ ID NO: 1 or WDYKY at residues 91-95 of SEQ ID NO: 3. By way of non-limiting examples, such a PD-1 binding fragment comprises at least 10, or at least 20, or at least 30, or at least 40, or at least 50, or at least 60, or at least 70, or at least 75, or at least 80, or at least 85, or at least 90, or at least 95, or at least 100 contiguous amino acids of the sequence of amino acids 20-121 of SEQ ID NO: 1, wherein a preferred embodiment of each such PD-1 binding fragment would comprise as a sub-fragment the amino acids WDYKY found at residues 110-114 of SEQ ID NO: 1 or WDYKY at residues 91-95 of SEQ ID NO: 3.

Other preferred polypeptides and PD-1 binding fragments specifically contemplated by the invention include the polypeptide sequence of amino acids 20-121 of SEQ ID NO: 1 (human full length) and PD-1 binding fragments thereof, wherein, in such polypeptide or PD-1 binding fragment, a cysteine is present at residues 42 and/or 102, with a cysteine at both positions being preferred, and/or wherein a phenylalanine is present at residue 21, and/or wherein a glutamic acid is present at residue 28, and/or wherein a threonine, and/or wherein a glutamine is present at residue 60, and/or wherein a glutamic acid is present at residue 101, and/or wherein isoleucine is present at residue 103, and/or wherein an isoleucine is present at residue 105, and/or wherein a glycine is present at residue 107, and/or wherein valine is present at residue 108, and/or wherein a tryptophan is present at residue 110, and/or wherein aspartic acid is present at residue 111, and/or wherein a tyrosine is present at residue 112, and/or wherein a lysine is present at residue 113, and/or wherein a tyrosine is present at residue 114, provided that, in the case of PD-1 binding fragments, said fragment is large enough to include such amino acid positions.

Additional preferred polypeptides and PD-1 binding fragments specifically contemplated by the invention include the polypeptide sequence of amino acids 1-102 of SEQ ID NO: 3 (human ECD) or SEQ ID NO: 4 (murine ECD) and PD-1 binding fragments thereof, wherein, in such polypeptide or PD-1 binding fragment, a cysteine is present at residues 23 and/or 83, with a cysteine at both positions being preferred, and/or wherein a phenylalanine is present at residue 2, and/or wherein a glutamic acid is present at residue 9, and/or wherein a threonine or arginine is present at residue 37, with threonine preferred, and/or wherein a glutamine is present at residue 41, and/or wherein arginine is present at residue 82, and/or wherein a leucine is present at residue 84, and/or wherein an isoleucine is present at residue 86, and/or wherein a glycine is present at residue 88, and/or wherein an alanine is present at residue 89, and/or wherein a tryptophan is present at residue 91, and/or wherein a aspartic acid is present at residue 92, and/or wherein a tyrosine is present at residue 93, and/or wherein a lysine is present at residue 94, and/or wherein a tyrosine is present at residue 95, provided that, in the case of PD-1 binding fragments, said fragment is large enough to include such amino acid positions.

In additional embodiments, any of the above polypeptides may also incorporate portions or fragments, for example, from 1 to 10 contiguous amino acids, drawn from the signal, transmembrane or C-terminal domains of the B7-DC or 67-H1 polypeptide, such as that of mouse or primate, preferably human.

Such polypeptides and/or PD-1 binding fragments can also be present in any of the fusion proteins of the invention, for example, where such polypeptide or PD-1 binding fragment represents the "first polypeptide" of such fusion protein.

In specific examples, the molecule, combined with a potentiating agent for use in a treatment regimen of the invention, comprises a PD-1 binding fragment of amino acids 20-221 of SEQ ID NO: 1. In one such embodiment, the fragment is from amino acids 20-121 of SEQ ID NO: 1, preferably where the fragment contains amino acids 110-114 of SEQ ID NO: 1. In some embodiments, more than one such fragment is present (as described elsewhere herein) and the molecule comprises at least 2, 3, 4, 5 or more fragments of a B7-DC protein, especially where the fragment is part of, or contains part of, amino acids 20-221 of SEQ ID NO: 1. In a preferred embodiment thereof, at least one said fragment is from amino acids 20-121 of SEQ ID NO: 1, more preferably wherein at least one said fragment includes amino acids 110-114 of SEQ ID NO: 1 (i.e., the sequence WDYKY (SEQ ID NO: 14)). In preferred embodiments, the PD-1 binding fragment comprises at least 10, or at least 25, or at least 50, or at least 75, or at least 100 contiguous amino acids in length.

The endogenous human signal peptide has the following sequence MIFLLLMLSL ELQLHQIAA (SEQ ID NO:5) and represents the first 19 amino acids of SEQ ID NO: 1. In certain embodiments, the polypeptide fragments of B7-DC can include 1, 2, 3, 4, 5, 6, 7, 8, 9, or 10 contiguous amino acids of the endogenous or heterologous signal peptide (which can be used to produce a recombinant B7-DC polypeptide by expression in and secretion from a transformed cell). It will also be appreciated that a useful B7-DC polypeptide can include 1, 2, 3, 4, 5, 6, 7, 8, 9, or 10 contiguous amino acids of the transmembrane domain of B7-DC, and/or 1, 2, 3, 4, 5, 6, 7, 8, 9, or 10 contiguous amino acids of the cytoplasmic domain, or combinations thereof provided the B7-DC fragment retains the ability to antagonize the PD-1 receptor.

The phenotypes of PD-1-/- mice provide direct evidence for PD-1 being a negative regulator of immune responses in vivo. In the absence of PD-1, mice on the C57BL/6 background slowly develop a lupus-like glomerulonephritis and progressive arthritis (Nishimura, et al., Immunity, 11:141-151 (1999)). PD-1-/- mice on the BALB/c background rapidly develop a fatal autoimmune dilated cardiomyopathy (Nishimura, et al., Science. 291:319-322 (2001)). However, substantial evidence indicates that B7-DC can function to costimulate activate T cell responses. In the presence of suboptimal TCR signals, B7-DC causes increased proliferation and production of cytokines in vitro (Tseng, et al., J. Exp. Med. 193:839-846 (2001)). On the other hand, in vitro studies indicate a negative regulatory role for B7-DC in T cell responses. These seemingly contradictory data are best interpreted by expression of additional receptors for B7-DC on T cells other than PD-1.

Therefore, B7-DC proteins, variants, fragments and fusions thereof, may have the advantage of directly enhancing T cell responses by binding to an unknown receptor that activates the T cell, in addition to enhancing T cell responses by preventing the PD-1 mediated inhibitory signal transduction.

2. B7-H1 Polypeptides

In another embodiment, the compound for use in combination with a potentiating agent in the treatment regimen of the invention, is, or comprises, a fragment of a mammalian B7-H1, preferably from mouse or primate, preferably human, wherein said fragment binds to and blocks PD-1 but does not result in inhibitory signal transduction through PD-1 and said fragment is at least 10, or at least 20, or at least 30, or at least 40, or at least 50, or at least 60, or at least 70, or at least 80, or at least 90, or at least 100 contiguous amino acids in length. In other embodiments, the fragment can be of variable length so long as it has the function of binding to PD-1 but does not produce inhibitory signal transduction that results in reduced T cell proliferation. Such B7-H1 fragments also find use as part of the first polypeptide portion of fusion proteins of the invention.

B7-H1 sequences are as follows:

```
Human B7-H1 Polypeptide (SEQ ID NO. 16):
MRIFAVFIFM TYWHLLNAFT VTVPKDLYVV EYGSNMTIEC KFPVEKQLDL AALIVYWEME  60

DKNIIQFVHG EEDLKVQHSS YRQRAQLLKD QLSLGNAALQ ITDVKLQDAG VYRCMISYGG 120

ADYKRITVKV NAPYNKINQR ILVVDPVTSE HELTCQAEGY PKAEVIWTSS DHQVLSGKTT 180

TTNSKREEKL FNVTSTLRIN TTTNEIFYCT FRRLDPEENH TAELVIPELP LAHPPNERTH 240

LVILGAILLC LGVALTFIFR LRKGRMMDVK KCGIQDTNSK KQSDTHLEET            290

Murine B7-H1 (SEQ ID NO: 17)
MRIFAGIIFT ACCHLLRAFT ITAPKDLYVV EYGSNVTMEC RFPVERELDL LALVVYWEKE  60

DEQVIQFVAG EEDLKPQHSN FRGRASLPKD QLLKGNAALQ ITDVKLQDAG VYCCIISYGG 120

ADYKRITLKV NAPYRKINQR ISVDPATSEH ELICQAEGYP EAEVIWTNSD HQPVSGKRSV 280

TTSRTEGMLL NVTSSLRVNA TANDVFYCTF WRSQPGQNHT AELIIPELPA THPPQNRTHW 240

VLLGSILLFL IVVSTVLLFL RKQVRMLDVE KCGVEDTSSK NRNDTQFEET            290

Macaca mulatta PD-L1 (SEQ ID NO: 18)
MRIFAVFIFT IYWHLLNAFT VTVPKDLYVV EYGSNMTIEC RFPVEKQLGL             60

TSLIVYWEME DKNIIQFVHG EEDLKVQHSN YRQRAQLLKD QLSLGNAALR            120

ITDVKLQDAG VYRCMISYGG ADYKRITVKV NAPYNKINQR ILVVDPVTSE            180

HELTCQAEGY PKAEVIWTSS DHQVLSGKTT TTNSKREEKL LNVTSTLRIN            240

TTANEIFYCI FRRLGPEENH TAELVIPELP LALPPNERTH LVILGAIFLL            300

LGVALTFIFY LRKGRMMDMK KSGIRVTNSK KQRDTQLEET                       340
```

B7-H1-Ig proteins are described in WO/2001/014557 (pub. 1 Mar. 2001) and in WO/2002/079499 (pub. 10 Oct. 2002).

3. PD-1 and Other Polypeptides

Other useful polypeptides of the invention include those that bind to the ligands of the PD-1 receptor. These include the PD-1 receptor protein, or soluble fragments thereof, which can bind to the PD-1 ligands, such as B7-H1 or B7-DC, and prevent binding to the endogenous PD-1 receptor, thereby preventing inhibitory signal transduction. B7-H1 has also been shown to bind the protein B7.1 (Butte et al., Immunity, Vol. 27, pp. 111-122, (2007)). Such fragments also include the soluble ECD portion of the PD-1 protein that includes mutations, such as the A99L mutation, that increases binding to the natural ligands (Molnar et al., Crystal structure of the complex between programmed death-1 (PD-1) and its ligand PD-L2, PNAS, Vol. 105, pp. 10483-10488 (29 Jul. 2008)). B7-1 or soluble fragments thereof, which can bind to the B7-H1 ligand and prevent binding to the endogenous PD-1 receptor, thereby preventing inhibitory signal transduction, are also useful.

PD-1 polypeptides useful in the methods of the invention are as follows:

```
Human PD-1
                                                            (SEQ ID NO: 19)
MQIPQAPWPV VWAVLQLGWR PGWFLDSPDR PWNPPTFFPA LLVVTEGDNA TFTCSFSNTS  60

ESFVLNWYRM SPSNQTDKLA AFPEDRSQPG QDCRFRVTQL PNGRDFHMSV VRARRNDSGT 120

YLCGAISLAP KAQIKESLRA ELRVTERRAE VPTAHPSPSP RPAGQFQTLV VGVVGGLLGS 180

LVLLVWVLAV ICSRAARGTI GARRTGQPLK EDPSAVPVFS VDYGELDFQW REKTPEPPVP 240

CVPEQTEYAT IVFPSGMGTS SPARRGSADG PRSAQPLRPE DGHCSWPL             288

Cynomolgus monkey PD-1
                                                            (SEQ ID NO: 20)
MQIPQAPWPV VWAVLQLGWR PGWFLESPDR PWNAPTFSPA LLLLVTEGDNA TFTCSFSNAS 60

ESPVLNWYRM SPSNQTDKLA AFPEDRSQPG QDCRFRVTRL PNGRDFHMSV VRARRNDSGT 120

YLCGAISLAP KAQIKESLRA ELRVTERRAE VPTAHPSPSP RPAGQFQTLV VGVVGGLLGS 180

LVLLVWVLAV ICSRAARGTI GARRTGQPLK EDPSAVPVFS VDYGELDFQW REKTPEPPVP 240

CVPEQTEYAT IVFPSGMGTS SPARRGSADG PRSAQPLRPE DGHCSWPL             288
```

In accordance with the invention, because B7-1 and fragments thereof can also bind to B7-H1 and send inhibitory transduction to T cells through B7-H1, blocking of this interaction can also reduce inhibitory signal transduction that occurs through B7-H1. Compounds for use in the invention include those molecules that block this type of interaction. Such molecules have been disclosed in Butte et al (2007), supra, and include anti-B7-H1 antibodies with dual-specificity that block either the B7-H1:87-1 and B7-H1:PD-1 interaction as well as antibodies exhibiting mono-specificity that block the PD-L1:B7-1 interaction. Compounds that block this interaction by blocking B7-1 are also useful, and include anti-B7-1 antibodies.

4. Variant Polypeptides

Polypeptides useful in the invention, as described, include those that are mutated to contain one or more amino acid substitutions, deletions, or insertions. Methods for mutagenesis are known in the art. The mutated or variant polypeptides inhibit or reduce inhibitory signal transduction through PD-1 receptors by binding to ligands of PD-1. Alternatively, the variants (e.g. B7-DC polypeptides) can bind to the PD-1 receptor and inhibit, reduce, or block inhibitory signal transduction through the PD-1 receptor. The variant polypeptides may be of any species of origin. In one embodiment, the variant polypeptide is from a mammalian species. In a preferred embodiment, the variant polypeptide is of murine or primate, preferably human, origin.

In one embodiment the variant polypeptide is a B7-DC polypeptide that has the same binding affinity to PD-1 as wildtype or non-variant B7-DC but does not have or has less than 10% ability to trigger inhibitory signal transduction through the PD-1 receptor relative to a non-mutated B7-DC polypeptide. In other embodiments, the variant B7-DC polypeptide has 10%, 20%, 30%, 40%, 50%, or 60% more binding affinity to PD-1 than wildtype B7-DC without triggering PD-1 inhibitory signaling transduction.

A variant polypeptide (e.g. a variant B7-DC polypeptide) includes those having any combination of amino acid substitutions, deletions or insertions so long as the PD-1 antagonizing activity is not substantially reduced versus the wild type. However, where there is such a reduction, this should be by no more than half that of the wild type so that said variant has at least 50% of the PD-1 antagonist activity of the wild type protein, preferably at least 60%, more preferably at least 80%, most preferably at least 90% or 95%, with at least 100% being especially preferred. Increases in such activity resulting from said variant is even more desirable. In one embodiment, isolated B7-DC variant polypeptides have amino acid alterations such that their amino acid sequence shares at least 60, 70, 80, 85, 90, 95, 97, 98, 99, 99.5 or 100% identity with an amino acid sequence of a wild type B7-DC polypeptide, especially that from a mammal, preferably wild type murine or wild type primate, preferably human, B7-DC polypeptide.

Polypeptide sequence identity can be calculated using the definition of % identity provided hereinabove.

Amino acid substitutions in polypeptides may be "conservative" or "non-conservative".

B7 family molecules, including B7-DC, are expressed at the cell surface with a membrane proximal constant IgC domain and a membrane distal IgV domain. Receptors for these ligands share a common extracellular IgV-like domain. Interactions of receptor-ligand pairs are mediated predominantly through residues in the IgV domains of the ligands and receptors. In general, IgV domains are described as having two sheets that each contains a layer of 6-strands. These β-strands are referred to as A', B, C, C', C'', D, E, F and G. In one embodiment the B7-DC variant polypeptides contain amino acid alterations (i.e., substitutions, deletions or insertions) within one or more of these β-strands in any possible combination. In another embodiment, B7-DC variants contain one or more amino acid alterations (i.e., substitutions, deletions or insertions) within the A', C, C', C'', D, E, F or G β-strands. In one embodiment, B7-DC variants contain one or more amino acid alterations in the G β-strand.

With respect to murine or primate, preferably human, B7-DC, a variant B7-DC polypeptide can contain, without limitation, substitutions, deletions or insertions at positions that do not substantially reduce binding to PD-1 relative to non-mutated B7-DC.

It is understood, however, that substitutions at the recited amino acid positions can be made using any amino acid or amino acid analog. For example, the substitutions at the recited positions can be made with any of the naturally-occurring amino acids (e.g., alanine, aspartic acid, asparagine, arginine, cysteine, glycine, glutamic acid, glutamine, histidine, leucine, valine, isoleucine, lysine, methionine, proline, threonine, serine, phenylalanine, tryptophan, or tyrosine).

While the substitutions described herein are with respect to mouse and primate, especially human, B7-DC, it is noted that one of ordinary skill in the art could readily make equivalent alterations in the corresponding polypeptides from other species (e.g., rat, hamster, guinea pig, gerbil, rabbit, dog, cat, horse, pig, sheep, cow or non-human primate).

Preferred fragments include all or part of the extracellular domain of B7-DC effective to bind to PD-1.

In one embodiment, variant B7-DC polypeptide fragments are those that retain the ability to bind to PD-1 without triggering PD-1 inhibitory signal transduction. One embodiment provides a variant B7-DC polypeptide that is a fragment of full-length B7-DC and typically has at least 20 percent, 30 percent, 40 percent, 50 percent, 60 percent, 70 percent, 80 percent, 90 percent, 95 percent, 98 percent, 99 percent, 100 percent, or even more than 100 percent of the PD-1 antagonist activity of the full-length variant B7-DC polypeptide.

Useful fragments of variant B7-DC polypeptides include soluble fragments. Soluble B7-DC fragments are fragments of B7-DC that may be shed, secreted or otherwise extracted from the producing cells. In one embodiment, variant B7-DC polypeptide fragments include the entire extracellular domain of B7-DC. The extracellular domain of B7-DC includes amino acids from about 20 to about amino acid 221 of murine or primate, preferably human, B7-DC. In another embodiment, variant B7-DC polypeptide fragments include the IgC and IgV domains of B7-DC. In another embodiment, variant B7-DC polypeptide fragments include the IgV domain of B7-DC.

In one embodiment, variant B7-DC polypeptide fragments contain a region of the polypeptide that is important for binding affinity for PD-1. These polypeptide fragments are useful to bind to and block the PD-1 receptor to prevent native ligands from binding to PD-1 receptor, thereby enhancing an immune response. Inhibiting interactions of native B7-H1 or B7-DC with PD-1 inhibits the suppression of immune responses that would otherwise occur. A polypeptide fragment of mouse or primate, preferably human, B7-DC that binds to PD-1 contains, by way of non-limiting example, amino acids 101-105, or 111-113. The binding of 87-H1 to PD-1 receptor typically is inhibited by at least 50 percent, or by at least 60 percent, or by at least 70 percent, or by at least 75 percent, or by at least 80 percent, or by at least 90 percent, or by at least 95 percent, or more compared to the level of binding of B7-H1 to PD-1 in the absence of the fragment.

Human PD-1 mutant A99L binds B7-DC and B7-H1 with higher affinity than unmutated human PD-1 (Lazar Molnar et al PNAS105 p. 10483-10488 (2008)). In one embodiment of the invention, the compound acting to reduce inhibitory signal transduction is a soluble protein, such as the ECD of PD-1 incorporating this mutation.

5. Modified Polypeptides

Polypeptides useful in the invention, as described, including variants, homologs and fragments thereof, can be modified by chemical moieties found associated with polypeptides in the normal cellular environment, for example, by phosphorylation, methylation, amidation, sulfation, acylation, glycosylation, sumoylation and ubiquitylation of the polypeptide.

Such polypeptides may also be modified by chemical moieties that are not normally part of polypeptides in a cellular environment. Such modifications can be introduced into the molecule by reacting targeted amino acid residues of the polypeptide with an organic derivatizing agent that is capable of reacting with selected side chains or terminal residues. Another useful modification is cyclization of the protein. Such modifications also include introduction of a label capable of providing a detectable signal, either directly or indirectly, including, but not limited to, radioisotopes and fluorescent compounds.

Examples of chemical derivatives of the polypeptides include lysinyl and amino terminal residues derivatized with succinic or other carboxylic acid anhydrides. Derivatization with a cyclic carboxylic anhydride has the effect of reversing the charge of the lysinyl residues. Other suitable reagents for derivatizing amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate. Carboxyl side groups, aspartyl or glutamyl, may be selectively modified by reaction with carbodiimides (R—N=C=N—R') such as 1-cyclohexyl-3-(2-morpholinyl-(4-ethyl)carbodiimide or 1-ethyl-3-(4-atonia-4,4-dimethylpentyl)carbodiimide. Furthermore, aspartyl and glutamyl residues can be converted to asparaginyl and glutaminyl residues by reaction with ammonia. Polypeptides of the invention can also include one or more D-amino acids that are substituted for one or more L-amino acids.

In other embodiments, the potentiating agent, such as CTX, may be itself part of the compound that reduces inhibitory signal transduction, such as where the potentiating agent is chemically linked to a PD-1 antagonist of the invention.

6. Fusion Proteins

Fusion polypeptides having a first fusion partner, or polypeptide portion, comprising all or a part of a PD-1 antagonist protein, a B7-DC polypeptide for example, (including variants, homologs and fragments thereof) fused (i) directly to a second polypeptide or, (ii) optionally, fused to a linker peptide sequence that is fused to the second polypeptide are also provided. The presence of the fusion partner can alter, for example, the solubility, affinity and/or valency of the PD-1 antagonist polypeptide. The disclosed fusion proteins include any combination of amino acid alteration (i.e., substitution, deletion or insertion), fragment, and/or modification of a PD-1 antagonist polypeptide as described above. In one embodiment, B7-DC fusion proteins include the extracellular domain of a B7-DC protein as the first binding partner. In another embodiment, such B7-DC fusion proteins include the IgV and IgC domain of a B7-DC protein as the first binding partner. In another embodiment, variant B7-DC fusion proteins include the IgV domain of a B7-DC protein as the first binding partner.

Representative first fusion partners include primate, preferably human, or murine B7-DC polypeptide, fragments thereof, and variants thereof disclosed hereinabove. Preferred fragments include the extracellular domain of B7-DC. As recited, the extracellular domain can include 1-10 contiguous amino acids of a signal peptide, B7-DC transmembrane domain, or both.

In one embodiment, the compositions and/or products and/or methods of the invention utilize PD-1 receptor antagonist, especially polypeptides, including variants, homologs and fragments thereof, that are coupled to other polypeptides to form fusion proteins that antagonize the PD-1 receptor by binding a PD-1 ligand, such as B7-H1, thereby inhibiting the ligand from interacting with PD-1. In another embodiment, PD-1 receptor antagonist polypeptides, or variants thereof, are coupled to other polypeptides to form fusion proteins that antagonize the PD-1 receptor by binding to and blocking the PD-1 receptor and inhibit or reduce inhibitory signal transduction through PD-1.

The second polypeptide binding partner, or second polypeptide portion, may be N-terminal or C-terminal relative to the PD-1 antagonist polypeptide. In a preferred embodiment, the second polypeptide is C-terminal to the PD-1 antagonist polypeptide.

In a preferred embodiment, the fusion protein contemplated for use in the methods and compositions and/or products of the invention comprises at least a portion of an antibody. With the advent of methods of molecular biology and recombinant technology, it is now possible to produce antibody molecules by recombinant means and thereby generate gene sequences that code for specific amino acid sequences found in the polypeptide structure of the antibodies. Such antibodies can be produced by either cloning the gene sequences encoding the polypeptide chains of said antibodies or by direct synthesis of said polypeptide chains, with in vitro assembly of the synthesized chains to form active tetrameric ($H_2L_2$) structures with affinity for specific epitopes and antigenic determinants. This has permitted the ready production of antibodies having sequences characteristic of neutralizing antibodies from different species and sources.

Regardless of the source of the antibodies, or how they are recombinantly constructed, or how they are synthesized, in vitro or in vivo, using transgenic animals, such as cows, goats and sheep, using large cell cultures of laboratory or commercial size, in bioreactors or by direct chemical synthesis employing no living organisms at any stage of the process, all antibodies have a similar overall 3 dimensional structure. This structure is often given as $H_2L_2$ and refers to the fact that antibodies commonly comprise 2 light (L) amino acid chains and 2 heavy (H) amino acid chains. Both chains have regions capable of interacting with a structurally complementary antigenic target. The regions interacting with the target are referred to as "variable" or "V" regions and are characterized by differences in amino acid sequence from antibodies of different antigenic specificity.

In preferred embodiments, the PD-1 receptor antagonist polypeptides, including fragments, mutants and other variants, have a first fusion partner having all or a part of a B7-DC protein or variant thereof fused (i) directly to a second polypeptide or, (ii) optionally, fused to a linker peptide sequence that is fused to the second polypeptide. The presence of the fusion partner can alter the solubility, affinity and/or valency of the B7-DC polypeptide. In more preferred embodiments, B7-DC polypeptides are fused to one or more domains of an Ig heavy chain constant region, more preferably an amino acid sequence corresponding to the hinge, $C_H2$ and $C_H3$ regions of a human immunoglobulin Cγ1 chain or to the hinge, $C_H2$ and $C_H3$ regions of a murine immunoglobulin Cγ2a chain. In a preferred embodiment, the constant region preferably includes a mutation (for example N297Q) to eliminate or reduce Fc receptor binding.

The hinge, $C_H2$ and $C_H3$ regions of a human immunoglobulin Cγ1 chain has the following amino acid sequence:

```
                                                         (SEQ ID NO: 6)
EPKSCDKTHT CPPCPAPELL GGPSVFLFPP KPKDTLMISR TPEVTCVVVD VSHEDPEVKF  60

NWYVDGVEVH NAKTKPREEQ YNSTYRVVSV LTVLHQDWLN GKEYKCKVSN KALPAPIEKT 120

ISKAKGQPRE PQVYTLPPSR DELTKNQVSL TCLVKGFYPS DIAVEWESNG QPENNYKTTP 180

PVLDSDGSFF LYSKLTVDKS RWQQGNVFSC SVMHEALHNH YTQKSLSLSP GK         232
```

The hinge, $C_H2$ and $C_H3$ regions of a murine immunoglobulin Cγ2a chain has the following amino acid sequence:

```
                                                         (SEQ ID NO: 7)
EPRGPTIKPC PPCKCPAPNL LGGPSVFIFP PKIKDVLMIS LSPIVTCVVV DVSEDDPDVQ  60

ISWFVNNVEV HTAQTQTHRE DYNSTLRVVS ALPIQHQDWM SGKEFKCKVN NKDLPAPIER 120

TISKPKGSVR APQVYVLPPP EEEMTKKQVT LTCMVTDFMP EDIYVEWTNN GKTELNYKNT 180

EPVLDSDGSY FMYSKLRVEK KNWVERNSYS CSVVHEGLHN HHTTKSFSRT PGK        233
```

Exemplary murine B7-DC fusion proteins contain amino acids 20-221 of murine B7-DC fused to amino acids 237-469 of murine IgG2a (CAA49868). Human B7-DC fusion proteins can contain amino acids 20-221 of human B7-DC fused to amino acids 245-476 of human IgG1 (AAA02914). The signal peptides for B7-DC fusion proteins can be the endogenous signal peptides or any other signal peptide that facilitates secretion of the fusion protein from a host.

A representative murine B7-DC-Ig fusion protein is encoded by the nucleic acid sequence of SEQ ID NO:8.

It will be appreciated that the disclosed nucleic acid sequences can be codon-optimized to increase levels of expression for synthesizing the fusion proteins useful in the methods and compositions of the present invention. Methods for codon optimization are known in the art.

The murine B7-DC-Ig fusion protein encoded by SEQ ID NO:8 has the following amino acid sequence:

```
                                                         (SEQ ID NO: 9)
MLLLLPILNL SLQLHPVAAL FTVTAPKEVY TVDVGSSVSL ECDFDRRECT ELEGIRASLQ  60

KVENDTSLQS ERATLLEEQL PLGKALFHIP SVQVRDSGQY RCLVICGAAW DYKYLTVKVK 120

ASYMRIDTRI LEVPGTGEVQ LTCQARGYPL AEVSWQNVSV PANTSHIRTP EGLYQVTSVL 180

RLKPQPSRNF SCMFWNAHMK ELTSAIIDPL SRMEPKVPRT WEPRGPTIKP CPPCKCPAPN 240

LLGGPSVFIF PPKIKDVLMI SLSPIVTCVV VDVSEDDPDV QISWFVNNVE VHTAQTQTHR 300

EDYNSTLRVV SALPIQHQDW MSGKEFKCKV NNKDLPAPIE RTISKPKGSV RAPQVYVLPP 360

PEEEMTKKQV TLTCMVTDFM PEDIYVEWTN NGKTELNYKN TEPVLDSDGS YFMYSKLRVE 420

KKNWVERNSY SCSVVHEGLH NHHTTKSFSR TPGK                            454
```

SEQ ID NO:10 provides the amino acid sequence for murine B7-DC-Ig fusion protein without the signal sequence.

```
                                                         (SEQ ID NO: 10)
LFTVTAPKEV YTVDVGSSVS LECDFDRREC TELEGIRASL QKVENDTSLQ SERATLLEEQ  60

LPLGKALFHI PSVQVRDSGQ YRCLVICGAA WDYKYLTVKV KASYMRIDTR ILEVPGTGEV 120

QLTCQARGYP LAEVSWQNVS VPANTSHIRT PEGLYQVTSV LRLKPQPSRN FSCMFWNAHM 180

KELTSAIIDP LSRMEPKVPR TWEPRGPTIK PCPPCKCPAP NLLGGPSVFI FPPKIKDVLM 240

ISLSPIVTCV VVDVSEDDPD VQISWFVNNV EVHTAQTQTH REDYNSTLRV VSALPIQHQD 300

WMSGKEFKCK VNNKDLPAPI ERTISKPKGS VRAPQVYVLP PPEEEMTKKQ VTLTCMVTDF 360

MPEDIYVEWT NNGKTELNYK NTEPVLDSDG SYFMYSKLRV EKKNWVERNS YSCSVVHEGL 420

HNHHTTKSFS RTPGK                                                 435
```

In one embodiment human B7-DC-Ig is encoded by the nucleic acid sequence of SEQ ID NO:11, encoding the amino acid sequence for human B7-DC-Ig:

```
                                                        (SEQ ID NO: 12)
MIFLLLMLSL ELQLHQIAAL FTVTVPKELY IIEHGSNVTL ECNFDTGSHV NLGAITASLQ  60

KVENDTSPHR ERATLLEEQL PLGKASFHIP QVQVRDEGQY QCIIIYGVAW DYKYLTLKVK 120

ASYRKINTHI LKVPETDEVE LTCQATGYPL AEVSWPNVSV PANTSHSRTP EGLYQVTSVL 180

RLKPPPGRNF SCVFWNTHVR ELTLASIDLQ SQMEPRTHPT WEPKSCDKTH TCPPCPAPEL 240

LGGPSVFLFP PKPKDTLMIS RTPEVTCVVV DVSHEDPEVK FNWYVDGVEV HNAKTKPREE 300

QYNSTYRVVS VLTVLHQDWL NGKEYKCKVS NKALPAPIEK TISKAKGQPR EPQVYTLPPS 360

RDELTKNQVS LTCLVKGFYP SDIAVEWESN GQPENNYKTT PPVLDSDGSF FLYSKLTVDK 420

SRWQQGNVFS CSVMHEALHN HYTQKSLSLS PGK                             453
```

The present invention specifically contemplates embodiments where the mature fusion protein useful in the methods and compositions of the invention have the signal sequence removed. In a preferred embodiment, the signal sequence is completely removed.

SEQ ID NO:13 provides the amino acid sequence for human B7-DC-Ig without the signal sequence.

```
                                                        (SEQ ID NO: 13)
LFTVTVPKEL YIIEHGSNVT LECNFDTGSH VNLGAITASL QKVENDTSPH RERATLLEEQ  60

LPLGKASFHI PQVQVRDEGQ YQCIIIYGVA WDYKYLTLKV KASYRKINTH ILKVPETDEV 120

ELTCQATGYP LAEVSWPNVS VPANTSHSRT PEGLYQVTSV LRLKPPPGRN FSCVFWNTHV 180

RELTLASIDL QSQMEPRTHP TWEPKSCDKT HTCPPCPAPE LLGGPSVFLF PPKPKDTLMI 240

SRTPEVTCVV VDVSHEDPEV KFNWYVDGVE VHNAKTKPRE EQYNSTYRVV SVLTVLHQDW 300

LNGKEYKCKV SNKALPAPIE KTISKAKGQP REPQVYTLPP SRDELTKNQV SLTCLVKGFY 360

PSDIAVEWES NGQPENNYKT TPPVLDSDGS FFLYSKLTVD KSRWQQGNVF SCSVMHEALH 420

NHYTQKSLSL SPGK.                                                 434
```

The present invention specifically contemplates embodiments where the disclosed B7-DC-Ig fusion proteins used in the methods and compositions disclosed herein have at least about 80%, 85%, 90%, 99% or 100% sequence identity to SEQ ID NO: 9, 10, 12, or 13.

In another embodiment of the invention, the fusion polypeptide may have bi-specific function whereby the first fusion partner binds to a ligand of PD-1, such as B7-H1, and the second fusion partner binds to the PD-1 receptor without triggering inhibitory signal transduction through the PD-1 receptor.

While a polypeptide useful in the invention may be monomeric or dimeric, the fusion proteins themselves may be present in a monomeric or an oligomeric form, preferably as a dimer. In specific embodiments, the fusion proteins useful as PD-1 antagonists in the methods and compositions of the invention may assemble spontaneously into oligomeric, especially dimeric, forms or may be chemically linked to form such oligomers by means well known in the art. For example, a fusion protein useful in practicing the invention may itself comprise a portion of a B7-DC polypeptide fused to a portion of an antibody and these may be further assembled into a dimer. In one such example, a polypeptide for use in the invention is fused as a single amino acid chain to the Fc region of an antibody (such as where this construct is expressed from a single recombinant polynucleotide), after which two such fusion products are linked to each other to form a homodimer, such as by a disulfide linkage between the respective Fc regions.

Such dimeric products may be homodimers (where both monomeric fusion proteins are identical) or may be heterodimers (where two different fusion proteins are linked to each other). The individual monomers of such dimers may be linked by any means known in the art, such as by covalent linkage (e.g., a disulfide bond) or by non-covalent linkage (such as an ionic interaction). The B7-DC-Ig used in the examples of the invention were present in the form of a homodimer having 2 copies of SEQ ID NO: 10 linked together by a disulfide linkage. In addition, the heterodimers of the invention include bispecific proteins and fusion proteins wherein one monomeric portion binds to PD-1 and the other binds to a natural ligand of PD-1. Such heterodimers are formed by coupling of polypeptides and fusion proteins fully described elsewhere herein.

In another useful embodiment of the invention, the PD-1 antagonist is a heterodimer, such as where two fusion proteins are linked together but they are not of identical amino acid sequence. In a specific example, each monomer may comprise an Fc portion of an antibody linked to an active fragment of a B7-DC polypeptide where these active fragments are from different portions of the B7-DC polypeptide or where a fusion protein comprising an Fc portion of an antibody fused to a full length native B7-DC polypeptide is linked (for example, cross-linked) to a fusion protein comprising an Fc portion of an antibody and an active fragment of a full length native B7-DC polypeptide. In each such case, the portion of the antibody used in forming each monomeric fusion protein may be different between the two monomeric units. Any such dimeric combination is specifically contemplated by the methods and compositions of the invention.

In a preferred dimeric fusion protein, the dimer results from the covalent bonding of Cys residue in the CH regions of two of the Ig heavy chains that are the same Cys residues that are disulfide linked in dimerized normal Ig heavy chains.

Still another embodiment provides a tetramer construct having a BirA substrate fused to the extracellular domain of a variant B7-DC polypeptide. Methods for making tetramer constructs are known in the art (see Pertovas, et al., *J. Exp. Med.*, 203:2281 (2006)).

7. Anti-PD-1 and Other Antibodies

Other PD-1 antagonists contemplated by the methods of this invention include antibodies that bind to PD-1 or ligands of PD-1, and other antibodies.

In one aspect, the present invention relates to a method of increasing a T cell response in a mammal in need thereof, comprising administering to said mammal an effective treatment regimen comprising an anti-PD-1 antibody and a potentiating agent, wherein said treatment regimen is effective to increase the T cell response of said mammal to said antigen.

Anti-PD-1 antibodies useful in the treatment regimens(s) of the invention include, but are not limited to, those described in the following publications:
PCT/IL03/00425 (Hardy et al., WO/2003/099196)
PCT/JP2006/309606 (Korman et al., WO/2006/121168)
PCT/US2008/008925 (Li et al., WO/2009/014708)
PCT/JP03/08420 (Honjo et al., WO/2004/004771)
PCT/JP04/00549 (Honjo et al., WO/2004/072286)
PCT/IB2003/006304 (Collins et al., WO/2004/056875)
PCT/US2007/088851 (Ahmed et al., WO/2008/083174)
PCT/US2006/026046 (Korman et al., WO/2007/005874)
PCT/US2008/084923 (Terrett et al., WO/2009/073533)
Berger et al., Clin. Cancer Res., Vol. 14, pp. 30443051 (2008).

A specific example of an anti-PD-1 antibody useful in the methods of the invention is MDX-1106 (see Kosak, US 20070166281 (pub. 19 Jul. 2007) at par. 42), a human anti-PD-1 antibody, preferably administered at a dose of 3 mg/kg.

In another aspect, the present invention relates to a method of increasing a T cell response in a mammal in need thereof, comprising administering to said mammal an effective treatment regimen comprising an anti-PD-1 ligand antibody, an anti-B7-H1 antibody for example, and a potentiating agent, wherein said treatment regimen is effective to increase the T cell response of said mammal to said antigen.

Anti-B7-H1 antibodies useful in the treatment regimens(s) of the invention include, but are not limited to, those described in the following publications:
PCT/US06/022423 (WO/2006/133396, pub. 14 Dec. 2006)
PCT/US07/088,851 (WO/2008/083174, pub. 10 Jul. 2008)
US 2006/0110383 (pub. 25 May 2006)

A specific example of an anti-B7-H1 antibody useful in the methods of the invention is MDX-1105 (WO/2007/005874, published 11 Jan. 2007)), a human anti-B7-H1 antibody. For anti-B7-DC antibodies see U.S. Pat. Nos. 7,411,051, 7,052,694, 7,390,888, 20060099203

Another embodiment of the invention includes a bi-specific antibody that comprises an antibody that binds to the PD-1 receptor bridged to an antibody that binds to a ligand of PD-1, such as B7-H1. In a preferred embodiment, the PD-1 binding portion reduces or inhibits signal transduction through the PD-1 receptor.

The antibody for use in the invention need not be an anti-PD-1 or anti-PD-1 ligand antibody but may be another antibody useful in mediating the effects of T cells in an immune response. In this aspect, the present invention relates to a method of increasing a T cell response to an antigen in a mammal in need thereof, comprising administering to said mammal an effective treatment regimen comprising an anti-CTLA4 antibody and a potentiating agent, wherein said treatment regimen is effective to increase the T cell response of said mammal to said antigen. An example of an anti-CTLA4 antibody contemplated for use in the methods of the invention includes an antibody as described in PCT/US2006/043690 (Fischkoff et al., WO/2007/056539).

Specific examples of an anti-CTLA4 antibody useful in the methods of the invention are Ipilimumab, also known as MDX-010 or MDX-101, a human anti-CTLA4 antibody, preferably administered at a dose of 10 mg/kg, and Tremelimumab a human anti-CTLA4 antibody, preferably administered at a dose of 15 mg/kg.

8. Small Molecule PD-1 Antagonists

The PD-1 receptor antagonists can also be small molecule antagonists. The term "small molecule" refers to small organic compounds having a molecular weight of more than 100 and less than about 2,500 daltons, preferably between 100 and 2000, more preferably between about 100 and about 1250, more preferably between about 100 and about 1000, more preferably between about 100 and about 750, more preferably between about 200 and about 500 daltons. The small molecules often include cyclical carbon or heterocyclic structures and/or aromatic or polyaromatic structures substituted with one or more functional groups. The small molecule antagonists reduce or interfere with PD-1 receptor signal transduction by binding to ligands of PD-1 such as B7-H1 and B7-DC and preventing the ligand from interacting with PD-1 or by binding directly to and blocking the PD-1 receptor without triggering signal transduction through the PD-1 receptor.

In one embodiment, such a small molecule may be administered in combination with another PD-1 antagonist or CTLA4 antagonist, such as an antibody specific for PD-1 or one of its ligands or an antibody specific for CTLA4 or one of its ligands. Thus, such small molecules may be administered as compounds in one or more of the methods of the invention or may be administered in combination with other compounds useful in the methods of the invention. For example, a series of small organic compounds have been shown to bind to the B7-1 ligand to prevent binding to CTLA4 (see Erbe et al., J. Biol. Chem., Vol. 277, pp. 7363-7368 (2002). Such small organics could be administered alone or together with an anti-CTLA4 antibody, in combination with CTX administration, to reduce inhibitory signal transduction of T cells.

In one embodiment, PD-1 antagonists or CTLA4 antagonists contemplated for use in the methods of the invention include anti-sense nucleic acids, both DNA and RNA, as well as siRNA molecules. Such anti-sense molecules prevent expression of PD-1 on T cells as well as production of T cell ligands, such as B7-H1, PD-L1 and PD-L2. For example, siRNA (for example, of about 21 nucleotides in length, which is specific for the gene encoding PD-1, or encoding a PD-1 ligand, and which oligonucleotides can be readily purchased commercially) complexed with carriers, such as polyethyleneimine (see Cubillos-Ruiz et al., *J. Clin. Invest.* 119(8): 2231-2244 (2009), are readily taken up by cells that express PD-1 as well as ligands of PD-1 and reduce expression of these receptors and ligands to achieve a decrease in inhibitory signal transduction in T cells, thereby activating T cells.

B. Potentiating Agents

In accordance with the invention, the activity of the PD-1 antagonist is increased, preferably synergistically, by the presence of a potentiating agent. The potentiating agent acts to increase the efficacy of the PD-1 receptor antagonist, possibly by more than one mechanism, although the precise mechanism of action is not essential to the broad practice of the present invention.

In the preferred embodiment, the potentiating agent is cyclophosphamide. Cyclophosphamide (CTX, Cytoxan®, or Neosar®) is an oxazahosphorine drug and analogs include ifosfamide (IFO, Ifex), perfosfamide, trophosfamide (trofosfamide; Ixoten), and pharmaceutically acceptable salts, solvates, prodrugs and metabolites thereof (U.S. patent application 20070202077 which is incorporated in its entirety). Ifosfamide (MITOXANA®) is a structural analog of cyclophosphamide and its mechanism of action is considered to be identical or substantially similar to that of cyclophosphamide. Perfosfamide (4-hydroperoxycyclophosphamide) and trophosphamide are also alkylating agents, which are structurally related to cyclophosphamide. For example, perfosfamide alkylates DNA, thereby inhibiting DNA replication and RNA and protein synthesis. New oxazaphosphorines derivatives have been designed and evaluated with an attempt to improve the selectivity and response with reduced host toxicity (Liang J, Huang M, Duan W, Yu X Q, Zhou S. Design of new oxazaphosphorine anticancer drugs. Curr Pharm Des. 2007; 13(9):963-78. Review). These include mafosfamide (NSC 345842), glufosfamide (D19575, beta-D-glucosylisophosphoramide mustard), S-(−)-bromofosfamide (CBM-11), NSC 612567 (aldophosphamide perhydrothiazine) and NSC 613060 (aldophosphamide thiazolidine). Mafosfamide is an oxazaphosphorine analog that is a chemically stable 4-thioethane sulfonic acid salt of 4-hydroxy-CPA. Glufosfamide is IFO derivative in which the isophosphoramide mustard, the alkylating metabolite of IFO, is glycosidically linked to a beta-D-glucose molecule. Additional cyclophosphamide analogs are described in U.S. Pat. No. 5,190,929 entitled "Cyclophosphamide analogs useful as anti-tumor agents" which is incorporated herein by reference in its entirety.

In other embodiments, the potentiating agent is an agent that reduces activity and/or number of regulatory T lymphocytes (T-regs), preferably Sunitinib (SUTENT®), anti-TGFβ or Imatinib (GLEEVAC®). The recited treatment regimen may also include administering an adjuvant.

Useful potentiating agents also include mitosis inhibitors, such as paclitaxol, aromatase inhibitors (e.g. Letrozole) and angiogenesis inhibitors (VEGF inhibitors e.g. Avastin, VEGF-Trap) (see, for example, Li et al., Vascular endothelial growth factor blockade reduces intratumoral regulatory T cells and enhances the efficacy of a GM-CSF-secreting cancer immunotherapy. Clin Cancer Res. 2006 Nov. 15; 12(22): 6808-16), anthracyclines, oxaliplatin, doxorubicin, TLR4 antagonists, and IL-18 antagonists.

C. Pharmaceutical Compositions

In one aspect, the invention relates to a therapeutic composition, comprising a molecule that prevents inhibitory signal transduction through PD-1, or a CTLA4 antagonist, and a potentiating agent in a pharmaceutically acceptable carrier. The components of said composition are present in an amount effective to increase a T cell response in a mammal. In specific embodiments, the potentiating agent is cyclophosphamide or an analog of cyclophosphamide, examples of such analogs having been recited above.

In other specific examples, the potentiating agent is an agent that reduces activity of regulatory T lymphocytes (T-regs), preferably where the activity is reduced due to a decrease in the number of said T-regs. In preferred non-limiting embodiments, the agent is Sunitinib (SUTENT®), anti-TGFβ or Imatinib (GLEEVAC®).

The potentiating agent useful in formulating compositions of the invention also include mitosis inhibitors, such as paclitaxol, aromatase inhibitors (e.g. Letrozole), agniogenesis inhibitors (VEGF inhibitors e.g. Avastin, VEGF-Trap), anthracyclines, oxaliplatin, doxorubicin, TLR4 antagonists, and IL-18 antagonists.

A therapeutic composition of the invention also optionally comprises at least one additional agent that may be one or more of an anti-PD-1 antibody, an anti-CTLA4 antibody, a mitosis inhibitor, an aromatase inhibitor, an Ata adenosine receptor (A2AR) antagonist, or an angiogenesis inhibitor.

Any of the therapeutic compositions of the invention may also contain one or more adjuvants as described herein.

A PD-1 antagonist useful as a component of a therapeutic composition of the invention includes any of the PD-1 antagonists recited herein for use in any of the methods of the invention. For example, such PD-1 antagonist includes any of the fusion proteins recited herein. Such antagonist can also be any of the polypeptides or PD-1 binding fragments recited herein for use as the first polypeptide portion of any of the fusion proteins described for use in any of the methods of the invention. Such antagonist can further be an antibody, such as any of the known anti-PD-1, -B7-DC or -B7-H1 antibodies mentioned herein.

A therapeutic composition of the invention also includes, in addition to or in place of the aforementioned PD-1 antagonist, an anti-CTLA4 antibody. Such a composition would therefore contain such an anti-CTLA4 antibody and a potentiating agent of the kind already described herein.

A therapeutic composition of the invention finds use in any of the methods of the invention disclosed herein. Such composition, while intended for use as an active treatment of a disease condition, may also find use as prophylactic compositions to prevent any of the diseases recited herein.

In one aspect, the present invention contemplates a therapeutic composition comprising a PD-1 antagonist and a potentiating agent in a pharmaceutically acceptable carrier, wherein the PD-1 antagonist and the potentiating agent are together present in an amount effective to increase a T cell response in a mammal.

Therapeutic compositions within the scope of the invention include compositions comprising any and all combinations of the PD-1 antagonists and/or antibodies disclosed herein with any of the recited potentiating agents. By way of non-limiting examples, a therapeutic composition of the invention includes a composition comprising an effective amount of one or more PD-1 antagonists, such as a combination of any or all of the full length polypeptides enumerated herein as specific SEQ ID NOs. or homologs thereof together with one or more fragments of any of said polypeptides, including where any or all of these are fused to other proteins, such as being fused to one or more immunoglobulins recited herein, or not so fused, and comprising one or more potentiating agents, such as cyclophosphamide alone, or cyclophosphamide plus one or more analogs thereof, of just one or more analogs of cyclophosphamide, or the potentiating agent may consist of cyclophosphamide and an agent that reduces T reg number in a mammal receiving the composition, or may consist of a cyclophosphamide analog plus an agent that reduces T reg number or the potentiating agent may consist only of one or more agents that reduce T reg number or other Treg activity. All such combinations are contemplated by the invention so long as the composition comprises at least one PD-1 antagonist and/or antibody mediating T cell activity and at least one potentiating agent.

The compositions of the invention may also include additional active agents. In preferred embodiments of any of the compositions of the invention, the pharmaceutical or therapeutic composition further comprises at least one additional agent selected from the group consisting of an anti-PD-1 antibody, an anti-CTLA4 antibody, a mitosis inhibitor, such as paclitaxel, an aromatase inhibitor, such as letrozole, an A2AR antagonist, an angiogenesis inhibitor, anthracyclines, oxaliplatin, doxorubicin, TLR4 antagonists, and IL-18 antagonists.

The PD-1 antagonist and/or potentiating agent may be administered by any suitable means. In a preferred embodiment, the PD-1 antagonist and/or potentiating agent is administered in an aqueous solution, by parenteral injection. The formulation may also be in the form of a suspension or emulsion. In general, pharmaceutical compositions are provided including effective amounts of a peptide or polypeptide, and optionally include pharmaceutically acceptable diluents, preservatives, solubilizers, emulsifiers, adjuvants and/or carriers. Such compositions include diluents sterile water, buffered saline of various buffer content (e.g., Tris-HCl, acetate, phosphate), pH and ionic strength; and optionally, additives such as detergents and solubilizing agents (e.g., TWEEN 20, TWEEN 80, Polysorbate 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

Pharmaceutical compositions of the invention may be administered by parenteral (intramuscular, intraperitoneal, intravenous (IV) or subcutaneous injection), transdermal (either passively or using iontophoresis or electroporation), or transmucosal (nasal, vaginal, rectal, or sublingual) routes of administration. The methods of the invention do not preclude administering the PD-1 antagonist and the potentiating agent by separate and different routes (e.g. topically).

The PD-1 antagonist and the potentiating agent may be administered at the same time, or at different times, with the potentiating agent being administered before or after the PD-1 antagonist. In one embodiment, a potentiating agent is administered both before and after the PD-1 antagonist. In one such embodiment, the same potentiating agent is administered before and after the PD-1 antagonist. In another embodiment, the potentiating agent administered before the PD-1 antagonist.

As used herein the term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease, and the treatment being effected. Therapeutically effective amounts of PD-1 receptor antagonists and/or antibodies together with a potentiating agents cause an immune response to be activated or sustained.

The selected dosage depends upon the desired therapeutic effect, on the route of administration, and on the duration of the treatment desired. Generally dosage levels of 0.001 to 50 mg/kg of body weight daily are administered to mammals. Preferably, said dose is 1 to 50 mg/kg, more preferably 1 to 40 mg/kg, or even 1 to 30 mg/kg, with a dose of 2 to 20 mg/kg being also a preferred dose. Examples of other dosages include 2 to 15 mg/kg, or 2 to 10 mg/kg or even 3 to 5 mg/kg, with a dose of about 4 mg/kg being a specific example.

For treatment regimens using a potentiating agent and an antibody, such as an anti-PD-1 antibody or an anti-CTLA4 antibody, dosages are commonly in the range of 0.1 to 100 mg/kg, with shorter ranges of 1 to 50 mg/kg preferred and ranges of 10 to 20 mg/kg being more preferred. An appropriate dose for a human subject is between 5 and 15 mg/kg, with 10 mg/kg of antibody (for example, human anti-PD-1 antibody, like MDX-1106) most preferred (plus a suitable dose of cyclophosphamide or other potentiating agent given up to about 24 hours before the antibody).

In general, by way of example only, dosage forms based on body weight for any of the signal transduction antagonists useful in the methods of the invention include doses in the range of 5-300 mg/kg, or 5-290 mg/kg, or 5-280 mg/kg, or 5-270 mg/kg, or 5-260 mg/kg, or 5-250 mg/kg, or 5-240 mg/kg, or 5-230 mg/kg, or 5-220 mg/kg, or 5-210 mg/kg, or 20 to 180 mg/kg, or 30 to 170 mg/kg, or 40 to 160 mg/kg, or 50 to 150 mg/kg, or 60 to 140 mg/kg, or 70 to 130 mg/kg, or 80 to 120 mg/kg, or 90 to 110 mg/kg, or 95 to 105 mg/kg, with doses of 3 mg/kg, 5 mg/kg, 7 mg/kg, 10 mg/kg, 15 mg/kg, 20 mg/kg, 25 mg/kg, 30 mg/kg, 50 mg/kg and 100 mg/kg being specific examples of preferred doses. Such doses may, of course, be repeated. The dose will, of course, be correlated with the identity of the mammal receiving said dose. Doses in the above-recited mg/kg ranges are convenient for mammals, including rodents, such as mice and rats, and primates, especially humans, with doses of about 5 mg/kg, about 10 mg/kg and about 15 mg/kg being especially preferred for treating humans.

In accordance with the treatment regimen of the invention, the potentiating agent, for example cyclophosphamide, is administered in non-toxic doses that vary depending on the animal. In specific embodiments, the potentiating agent is administered by any suitable means of administration, including parenteral or oral, the former including system administration, such as intravenous. For example, a potentiating agent like cyclophosphamide is normally administered orally. Such administration may be at any convenient dosage, depending on the potentiating agent. The dosage in each case may be based on body weight or may be administered as a unit dosage.

While CTX itself is nontoxic, some of its metabolites are cytotoxic alkylating agents that induce DNA crosslinking and, at higher doses, strand breaks. Many cells are resistant to CTX because they express high levels of the detoxifying enzyme aldehyde dehydrogenase (ALDH). CTX targets proliferating lymphocytes, as lymphocytes (but not hematopoietic stem cells) express only low levels of ALDH, and cycling cells are most sensitive to DNA alkylation agents.

Low doses of CTX (<200 mg/kg) can have immune stimulatory effects, including stimulation of anti-tumor immune responses in humans and mouse models of cancer (Brode & Cooke *Crit. Rev. Immunol.* 28:109-126 (2008)). These low doses are sub-therapeutic and do not have a direct anti-tumor activity. In contrast, high doses of CTX inhibit the anti-tumor response. Several mechanisms may explain the role of CTX in potentiation of anti-tumor immune response: (a) depletion of CD4+CD25+FoxP3+ Treg (and specifically proliferating Treg, which may be especially suppressive), (b) depletion of B lymphocytes; (c) induction of nitric oxide (NO), resulting in suppression of tumor cell growth; (d) mobilization and expansion of CD11b+Gr-1+ MDSC. These primary effects have numerous secondary effects; for example following Treg depletion macrophages produce more IFN-γ and less IL-10. CTX has also been shown to induce type I IFN expression and promote homeostatic proliferation of lymphocytes.

Treg depletion is most often cited as the mechanism by which CTX potentiates the anti-tumor immune response. This conclusion is based in part by the results of adoptive transfer experiments. In the AB1-HA tumor model, CTX treatment at Day 9 gives a 75% cure rate. Transfer of purified Treg at Day 12 almost completely inhibited the CTX response (van der Most et al. *Cancer Immunol. Immunother.* 58:1219-1228 (2009). A similar result was observed in the HHD2 tumor model: adoptive transfer of CD4+CD25+ Treg after CTX pretreatment eliminated therapeutic response to vaccine (Taieb, J. *J. Immunol.* 176:2722-2729 (2006)).

Numerous human clinical trials have demonstrated that low dose CTX is a safe, well-tolerated, and effective agent for promoting anti-tumor immune responses (Bas, & Mastrangelo *Cancer Immunol. Immunother.* 47:1-12 (1998)).

The optimal dose for CTX to potentiate an anti-tumor immune response, is one that lowers overall T cell counts by lowering Treg levels below the normal range but is subtherapeutic (see Machiels et al. Cancer Res. 61:3689-3697 (2001)).

In human clinical trials where CTX has been used as an immunopotentiating agent, a dose of 300 mg/m$^2$ has usually been used. For an average male (6 ft, 170 pound (78 kg) with a body surface area of 1.98 m$^2$), 300 mg/m$^2$ is 8 mg/kg, or 624 mg of total protein. In mouse models of cancer, efficacy has been seen at doses ranging from 15-150 mg/kg, which relates to 0.45-4.5 mg of total protein in a 30 g mouse (Machiels et al. *Cancer Res.* 61:3689-3697 (2001), Hengst et al *Cancer Res.* 41:2163-2167 (1981), Hengst *Cancer Res.* 40:2135-2141 (1980)).

For larger mammals, such as a primate, preferably human, patient, such mg/m$^2$ doses may be used but unit doses administered over a finite time interval may be preferred. Such unit doses may be administered on a daily basis for a finite time period, such as up to 3 days, or up to 5 days, or up to 7 days, or up to 10 days, or up to 15 days or up to 20 days or up to 25 days, are all specifically contemplated by the invention. The same regimen may be applied for the other potentiating agents recited herein.

All such administrations may occur before or after administration of a PD-1 binding molecule of the invention. Alternatively, administration of one or more doses of a PD-1 binding molecule of the invention may be temporally staggered with the administration of potentiating agent to form a uniform or non-uniform course of treatment whereby one or more doses of potentiating agent are administered, followed by one or more doses of a PD-1 binding compound, followed by one or more doses of potentiating agent, all according to whatever schedule is selected or desired by the researcher or clinician administering said agents.

In other specific embodiments, the treatment regimen includes multiple administrations of one or more PD-1 antagonists. In some embodiments, such multiple administrations of PD-1 antagonists are in conjunction with multiple administrations of the same or different potentiating agents.

As in other embodiments of the invention, here the potentiating agent is administered at least 1, 2, 3, 5, 10, 15, 20, 24 or 30 hours prior to or after administering of the PD-1-antagonist.

The pharmaceutical compositions useful herein also contain a pharmaceutically acceptable carrier, including any suitable diluent or excipient, which includes any pharmaceutical agent that does not itself induce the production of antibodies harmful to the individual receiving the composition, and which may be administered without undue toxicity. Pharmaceutically acceptable carriers include, but are not limited to, liquids such as water, saline, glycerol and ethanol, and the like, including carriers useful in forming sprays for nasal and other respiratory tract delivery or for delivery to the ophthalmic system. A thorough discussion of pharmaceutically acceptable carriers, diluents, and other excipients is presented in REMINGTON'S PHARMACEUTICAL SCIENCES (Mack Pub. Co., N.J. current edition).

Vaccine compositions (as discussed below) may further incorporate additional substances to stabilize pH, or to function as adjuvants, wetting agents, or emulsifying agents, which can serve to improve the effectiveness of the vaccine.

Vaccines are generally formulated for parenteral administration and are injected either subcutaneously or intramuscularly. Such vaccines can also be formulated as suppositories or for oral administration, using methods known in the art, or for administration through nasal or respiratory routes.

D. Methods of Manufacture

Isolated PD-1 antagonist polypeptides, including variants, homologs and fragments thereof, either wild-type or mutated, and fusion proteins comprising any of these, all contemplated for use in the invention, can be obtained by, for example, chemical synthesis or by recombinant production in a host cell. To recombinantly produce a costimulatory polypeptide, a nucleic acid containing a nucleotide sequence encoding the polypeptide can be used to transform, transduce, or transfect a bacterial or eukaryotic host cell (e.g., an insect, yeast, or mammalian cell). It will be appreciated that the nucleotide sequences can be codon-optimized to increase levels of protein expression in a particular kind of host cell. Methods for codon optimization are well known in the art. In general, nucleic acid constructs include a regulatory sequence operably linked to a nucleotide sequence encoding a costimulatory polypeptide. Regulatory sequences (also referred to herein as expression control sequences) typically do not encode a gene product, but instead affect the expression of the nucleic acid sequences to which they are operably linked. The signal peptides used to secrete proteins from a cell can be the endogenous signal peptides or any other signal peptide that facilitates secretion of the fusion protein from a host.

For general molecular biology procedures useful in practicing the present invention, a number of standard references are available that contain procedures well known in the art of molecular biology and genetic engineering and which procedures need not be further described herein. Useful references include Sambrook, et al., Molecular Cloning: A Laboratory Manual, Second Edition, Cold Spring Harbor, N.Y., (1989), Wu et al, *Methods in Gene Biotechnology* (CRC Press, New York, N.Y., 1997), and *Recombinant Gene Expression Protocols*, in *Methods in Molecular Biology*, Vol. 62, (Tuan, ed., Humana Press, Totowa, N.J., 1997), the disclosures of which are hereby incorporated by reference.

E. Disease Treatment

Diseases to be treated or prevented by administering a therapeutic combination provided by the present invention include a malignant tumor or a chronic infectious disease caused by a bacterium, virus, protozoan, helminth, or other microbial pathogen that enters intracellularly. Such diseases are often combatted through attack by cytotoxic T lymphocytes. Because the present invention provides combination therapes useful in enhancing T cell responses, through increased T cell activity, increased T cell proliferation and reduced T cell inhibitory signals, the combination therapies of the invention have unique advantage in treating (or even preventing) such diseases.

In one embodiment, because viral infections are cleared primarily by T-cells, an increase in T-cell activity is therapeutically useful in enhancing clearance of an infective viral agent from an animal or primate, preferably human, subject. Thus, the disclosed compounds of the invention, with PD-1 receptor antagonist activity, together with a potentiating agent work in combination for the treatment of local or systemic viral infections. Infections that are to be treated by the compounds of the invention include, but are not limited to, immunodeficiency (e.g., HIV), papilloma (e.g., HPV), herpes (e.g., HSV), encephalitis, influenza (e.g., human influenza virus A), hepatitis (e.g. HCV, HBV), and common cold (e.g., human rhinovirus) viral infections. Pharmaceutical formulations of PD-1 receptor antagonists compositions can also be administered to treat systemic viral diseases, including, but not limited to, AIDS, influenza, the common cold, or encephalitis.

Non-viral infections treatable by the compounds of the invention include, but are not limited to, infections cause by microorganisms including, but not limited to, *Actinomyces, Anabaena, Bacillus, Bacteroides, Bdellovibrio, Bordetella, Borrelia, Campylobacter, Caulobacter, Chlamydia, Chlorobium, Chromatium, Clostridium, Corynebacterium, Cytophaga, Deinococcus, Escherichia, Francisella, Halobacterium, Heliobacter, Haemophilus, Hemophilus influenza* type B (HIB), *Hyphomicrobium, Legionella, Leptspirosis, Listeria, Meningococcus* A, B and C, *Methanobacterium, Micrococcus, Myobacterium, Mycoplasma, Myxococcus, Neisseria, Nitrobacter, Oscillatoria, Prochloron, Proteus, Pseudomonas, Phodospirillum, Rickettsia, Salmonella, Shigella, Spirillum, Spirochaeta, Staphylococcus, Streptococcus, Streptomyces, Sulfolobus, Thermoplasma, Thiobacillus, Treponema, Vibrio, Yersinia, Cryptococcus neoformans, Histoplasma* sp. (such as *Histoplasma capsulatum*), *Candida albicans, Candida tropicalis, Nocardia asteroides, Rickettsia rickettsii, Rickettsia typhi, Leishmania, Mycoplasma pneumoniae, Chlamydial psittaci, Chlamydial trachomatis, Plasmodium* sp. (such as *Plasmodium falciparum*), *Trypanosoma brucei, Entamoeba histolytica, Toxoplasma gondii, Trichomonas vaginalis* and *Schistosoma mansoni*.

In one embodiment, the present invention provides methods and compositions for inducing or enhancing an immune response in host for treating cancer. The types of cancer that may be treated with the provided compositions and methods include, but are not limited to, the following: bladder, brain, breast, cervical, colo-rectal, esophageal, kidney, liver, lung, nasopharangeal, pancreatic, prostate, skin, stomach, uterine, ovarian testicular, and hematologic cancer.

Malignant tumors which may be treated are classified herein according to the embryonic origin of the tissue from which the tumor is derived. Carcinomas are tumors arising from endodermal or ectodermal tissues such as skin or the epithelial lining of internal organs and glands. Sarcomas, which arise less frequently, are derived from mesodermal connective tissues such as bone, fat, and cartilage. The leukemias and lymphomas are malignant tumors of hematopoietic cells of the bone marrow. Leukemias proliferate as single cells, whereas lymphomas tend to grow as tumor masses. Malignant tumors may show up at numerous organs or tissues of the body to establish a cancer.

As a demonstration of the value of the treatment regimens of the invention, the murine analog of B7-DC-Ig (in which the mouse B7-DC ECD, which shares 72% sequence identity with the human protein, is fused to the Fc domain of mouse $IgG_{2a}$) tested in syngeneic mouse tumor models for colon cancer, mastocytoma, and other tumor types incorporating a cyclophosphamide (CTX) pre-treatment as described herein. The results showed that treatment with a single subtherapeutic dose of CTX, which acts as an immunopotentiating agent, followed by murine B7-DC-IG eradicates established CT26 colon carcinoma tumors in up to 80% of the animals. Further, in CT26 colon carcinoma tumor re-challenge studies, no tumor re-growth was detected in mice that had previously eradicated tumor following CTX+murine B7-DC-Ig treatment. These mice were also shown to have an increased tumor-specific CTL population relative to naïve mice.

In one embodiment, the present invention contemplates use of a compound that reduces inhibitory signal transduction in a T cell, as described elsewhere herein, in the manufacture of a medicament for increasing a T cell response by combination therapy wherein said compound is administered in conjunction with a potentiating agent. Further, the compound that reduces inhibitory signal transduction in a T cell and said potentiating agent are provided as separate medicaments for administration at different times, preferably where the potentiating agent is administered prior to the compound that reduces inhibitory signal transduction, for example, up to 24 hours prior to the inhibitory compound (or other time intervals recited herein). Preferably, the compound and potentiating agent are for use in the treatment of an infectious disease or cancer, including diseases caused by any of the infectious agents or cancers recited elsewhere herein.

In a preferred embodiment, a compound useful in these methods is a recombinant protein composed of the ECD of human B7-DC fused to the Fc domain of human $IgG_1$, referred to herein as B7-DC-Ig.

In one embodiment, the present invention relates to a medical kit for administering a compound that reduces inhibitory signal transduction in a T cell, as disclosed herein, in combination with a potentiating agent, said kit comprising:

(a) a dosage supply of a compound that reduces inhibitory signal transduction in a T cell, (b) a supply of a potentiating agent;

(c) a supply of pharmaceutically acceptable carrier; and (d) printed instructions for administering the compound in a use as described above.

F. Combination Therapies

Vaccines require strong T cell response to eliminate cancer cells and infected cells or infectious agents. PD-1 receptor antagonists described herein can be administered as a component of a vaccine, along with a potentiating agent, to provide a costimulatory signal to T cells. Vaccines disclosed herein include antigens, a PD-1 receptor antagonist and optionally adjuvants and targeting molecules.

The antigens against which the T cell response is enhanced by the methods and composition of the invention includes peptides, proteins, polysaccharides, saccharides, lipids, nucleic acids, or combinations thereof. The antigens, in the case of disease, are present due to the disease process.

The disclosed PD-1 receptor antagonists compositions may be administered in conjunction with prophylactic vaccines, which confer resistance in a subject to subsequent exposure to infectious agents, or in conjunction with therapeutic vaccines, which can be used to initiate or enhance a subject's immune response to a pre-existing antigen, such as a tumor antigen in a subject with cancer, or a viral antigen in a subject infected with a virus.

The desired outcome of a prophylactic, therapeutic or desensitized immune response may vary according to the disease, based on principles well known in the art. For example, an immune response against an infectious agent may completely prevent colonization and replication of an infectious agent, affecting "sterile immunity" and the absence of any disease symptoms. However, a vaccine against infectious agents may be considered effective if it reduces the number, severity or duration of symptoms; if it reduces the number of individuals in a population with symptoms; or reduces the transmission of an infectious agent. Similarly, immune responses against cancer, allergens or infectious agents may completely treat a disease, may alleviate symptoms, or may be one facet in an overall therapeutic intervention against a disease. For example, the stimulation of an immune response against a cancer may be coupled with surgical, chemotherapeutic, radiologic, hormonal and other immunologic approaches in order to affect treatment.

The methods and products of the invention do not preclude use of an adjuvant in addition to the potentiating agent. Such adjuvant may be administered, for example, along with the PD-1 antagonist. The adjuvants useful in the compositions and methods of the invention include, but are not limited to, one or more of the following: oil emulsions (e.g., Freund's adjuvant); saponin formulations; virosomes and viral-like particles; bacterial and microbial derivatives; immunostimulatory oligonucleotides; ADP-ribosylating toxins and detoxified derivatives; alum; BCG; mineral-containing compositions (e.g., mineral salts, such as aluminium salts and calcium salts, hydroxides, phosphates, sulfates, etc.); bioadhesives and/or mucoadhesives; microparticles; liposomes; polyoxyethylene ether and polyoxyethylene ester formulations; muramyl peptides; polyphosphazene; imidazoquinolone compounds; and surface active substances (e.g. lysolecithin, pluronic polyols, polyanions, peptides, oil emulsions, keyhole limpet hemocyanin, and dinitrophenol). Useful adjuvants also include immunomodulators such as cytokines, interleukins (e.g., IL-1, IL-2, IL-4, IL-5, IL-6, IL-7, IL-12, etc.), interferons (e.g., interferon-γ), macrophage colony stimulating factor, and tumor necrosis factor.

Nothing herein precludes the disclosed PD-1 receptor antagonist, including any of the polypeptides, fragments, variants, homologs and fusion proteins disclosed herein, from being administered to a subject in need thereof in combination with one or more additional therapeutic agents (in addition to the potentiating agent). The additional therapeutic agents are selected based on the condition, disorder or disease to be treated. For example, PD-1 receptor antagonists can be co-administered with one or more additional agents that function to enhance or promote an immune response, and which are considered herein as active agents.

Such agents include, but are not limited to, amsacrine, bleomycin, busulfan, capecitabine, carboplatin, carmustine, chlorambucil, cisplatin, cladribine, clofarabine, crisantaspase, cytarabine, dacarbazine, dactinomycin, daunorubicin, docetaxel, doxorubicin, epirubicin, etoposide, fludarabine, fluorouracil, gemcitabine, hydroxycarbamide, idarubicin, ifosfamide, irinotecan, leucovorin, liposomal doxorubicin, liposomal daunorubicin, lomustine, melphalan, mercaptopurine, mesna, methotrexate, mitomycin, mitoxantrone, oxaliplatin, paclitaxel, pemetrexed, pentostatin, procarbazine, raltitrexed, satraplatin, streptozocin, tegafururacil, temozolomide, teniposide, thiotepa, tioguanine, topotecan, treosulfan, vinblastine, vincristine, vindesine, vinorelbine, or a combination thereof. Representative pro-apoptotic agents include, but are not limited to fludarabin-etaurosporine, cycloheximide, actinomycin D, lactosylceramide, 15d-PGJ(2) and combinations thereof.

The therapies provided by the methods and compositions of the present invention may also be used in conjunction with other types of therapies, such as radiation treatments, surgery, and the like.

G. Assays for Antagonist Activity

The present invention recites a number specific structures useful in practicing the methods of the invention. Other compounds possessing antagonist activity and being useful in the methods of the invention may also be identified by reference to well known assay procedures for identifying chemical structures that bind to PD-1, CTLA4, and ligands of any of these and that also possess the ability to reduce inhibitory signal transduction in T cells. Some such assays are binding assays useful in determining if a selected chemical structure binds to receptors; these are well known in the art and need not be discussed in detail herein (see, for example, U.S. 2008/0274490, (pub. 6 Nov. 2008) and U.S. Pat. No. 7,105, 328 (issued 12 Sep. 2006), each showing assays for PD-1 signaling modulators using T cells) the disclosures of which are hereby incorporated by reference in its entirety. Other assays are used to determine the effects of agents of the invention, such as active fragments, to activate T cells by increasing proliferation and/or production of cytokines. Such assays are also well known in the art. For example, increased proliferation of cells can be demonstrated by increased $^3$H-thymidine incorporation (due to increased DNA synthesis needed for cellular multiplication) or ELISA and/or RIA for detecting increased production of cytokines by T cells in culture.

In one such experiment, PD-1 binding activity of human B7-DC-Ig was assessed by ELISA. 96-well ELISA plates were coated with 100 uL 0.75 ug/mL recombinant human PD-1/Fc (R&D Systems) diluted in BupH Carbonate/Bicarbonate pH 9.4 buffer (Pierce) for 2 hours and then blocked with BSA solution (Jackson ImmunoResearch) for 90-120 minutes. Serially diluted human B7-DC-Ig (wild type, as well as D111S mutein, and K113S mutants that were selected for reduced binding to PD-1) as well as human IgG1 isotype control were allowed to bind for 90 minutes. Bound B7-DC-Ig was detected using 100 uL of 0.5 ug/mL biotin conjugated anti-human B7-DC clone MIH18 (eBioscience) followed by 1:1000 diluted HRP-Streptavidin (BD Bioscience) and TMB substrate (BioFX). Absorbance at 450 nm was read using a plate reader (Molecular Devices) and data were analyzed in SoftMax using a 4-parameter logistic fit. The data showed that human B7-DC-Ig (wildtype) bound to PD-1 but the K113S and D111S mutants do not bind to PD-1.

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

The invention is described in more detail in the following non-limiting examples. It is to be understood that these methods and examples in no way limit the invention to the embodiments described herein and that other embodiments and uses will no doubt suggest themselves to those skilled in the art.

EXAMPLES

Example 1

B7-DC-Ig Binds to PD01 Expressing CHO Cells

B7-DC-Ig was first conjugated with allophycocyanin (APC) and then incubated at various concentrations with a CHO cell line constitutively expressing PD-1 or parent CHO cells that do not express PD-1. Binding was analyzed by flow cytometry. FIG. 1 shows the median fluorescence intensity (MFI) of B7-DC-Ig-APC as a function of the concentration of probe (x-axis). B7-DC-Ig-APC binds to CHO.PD-1 cells (solid circle) but not untransfected CHO cells (gray triangle).

Example 2

B7-DC-Ig Competes with B7-H1 for Binding to PD-1

B7-H1-Ig was first conjugated with allophycocyanin (APC). Unlabeled B7-DC-Ig at various concentrations was first incubated with a CHO cell line constitutively expressing PD-1 before adding B7-H1-Ig-APC to the probe and cell mixture. FIG. 2 shows the median fluorescence intensity (MFI) of B7-H1-Fc-APC is shown as a function of the concentration of unlabeled B7-DC-Ig competitor (x-axis) added. As the concentration of unlabeled B7-DC-Ig is increased the amount of B7-H1-Ig-APC bound to CHO cells decreases, demonstrating that B7-DC-Ig competes with B7-H1 for binding to PD-1.

Example 3

CT26 Tumor Model

Mouse colorectal tumor cell line, CT26, was obtained from ATCC. A master cell bank at Passage 4 was generated following ATCC guidelines. Cells were tested and confirmed no mycoplasma and other pathogen contamination. One vial of tumor cells was thawed from the cryopreserved stocks and grown for two passages prior to inoculation.

CT26 cells were split at 1:5 dilution with 30 mL complete medium (RPMI+10% FBS, 2 mM L-Glu, and 1×P/S) for two days culture or at 1:10 dilution with 30 ml complete medium for 3 days culture.

CT26 cells were harvested by aspirating medium, rinsing the flask with 5 mL PBS, adding 5 mL trypsin, incubating at 37° C. for 2 min, and then neutralizing with 10 mL complete medium. After centrifuge at 600×g (~1000 rpm) for 5 min, media was aspirated and the cell pellet was resuspended by pipetting with 10 ml plain RPMI. This wash step was repeated for three times.

Cell number and viability of the inoculated cells were analyzed by trypan blue dye staining with proper dilution (e.g. 1:5 dilution, 10 µL cells+40 µL trypan blue) and confirmed by NOVA cell count during the last wash step. Cell viability generally was greater than 95% for inoculation.

CT26 cells were diluted to $6.7 \times 10^5$ cells/mL for initial inoculation with plain RPMI and stored on ice. Typically each mouse was inoculated with 150 µL ($1 \times 10^5$ cells).

On Day 9, all the tumor-bearing mice were first grouped into a rat cage and randomly divided the mice to experimental groups. CTX solution was reconstituted by 1×PBS to 4 mg/mL. Mice were intraperitoneally (IP) injected with 0.5 mL of CTX solution resulting in 2 mg for a 20 gram mouse, i.e. 100 mg/kg.

On Day 10, mice were IP injected with 0.5 mL of B7-DC-Ig (0.2 mg/mL) resulting in 0.1 mg for a 20 gram mouse, i.e. 5 mg/kg. The same dose was given 2 time a week for 4 weeks, total 8 doses. Tumor growth were monitored by measuring the tumor twice weekly, starting on the day when giving B7-DC-Ig via a digital caliper. Tumor volume was calculated as following:

$$\text{Tumor volume} = \pi (D_{short})^2 \times (D_{long})/6 = \sim 0.52 \times (D_{short})^2 \times (D_{long})$$

Mice were euthanized and taken off the study if the tumor volume reached 2000 mm$^3$ or if there were skin ulcers and infections at the tumor inoculation site.

Example 4

Combination of Cyclophosphamide and B7-DC-Ig can Eradicate Established Tumors

Balb/C mice at age of 9 to 11 weeks were implanted subcutaneously with $1.0 \times 10^5$ CT26 colorectal tumor cells as described above. On day 10 post tumor implantation, mice received 100 mg/kg of cyclophosphamide. B7-DC-Ig treatment started 1 day later, on day 11. Mice were treated with 100 ug of B7-DC-Ig, 2 doses per week, for 4 weeks and total 8 doses. 75% of the mice that received the CTX+B7-DC-Ig treatment regimen eradicated the established tumors by Day 44, whereas all mice in the control CTX alone group died as a result of tumor growth or were euthanized because tumors exceeded the sizes approved by IACUC (results shown in FIG. 3). These results demonstrate the effectiveness of the treatment regimen on established tumors and not mere prophylaxis.

Example 5

Combination of Cyclophosphamide and B7-DC-Ig can Eradicate Established Tumors and Protect Against Tumor Re-Challenge Mice eradicated established CT26 colorectal tumors from the above described experiment were rechallenged with $1 \times 10^5$ CT26 cells on Day 44 and Day 70. No tumors grew out from the rechallenge suggesting they had developed long term anti-tumor immunity from the cyclophosphamide and B7-DC-Ig combination treatment. All mice in the vehicle control group developed tumors (results shown in FIG. 4). These results show the effectiveness of the treatment regimen on established tumors and that the cyclophosphamide and B7-DCIg combination treatment resulted in memory responses to tumor antigens.

Example 6

Combination of Cyclophosphamide and B7-DC-Ig can Generate Tumor Specific, Memory Cytotoxic T Lymphocytes Mice eradicated established CT26 colorectal tumors from the above described experiment were rechallenged with $2.5 \times 10^5$ CT26 cells on Day 44. Seven days later, mouse spleens were isolated. Mouse splenocytes were pulsed with 5 or 50 ug/mL of ovalbumin (OVA) or AH1 peptides for 6 hours in the presence of a Golgi blocker (BD BioScience). Memory T effector cells were analyzed by assessing CD8$^+$/IFNγ$^+$ T cells. Results in FIG. 5 show that there were significant amount of CT26 specific T effector cells in the CT26 tumor-eradicated mice.

Example 7

Effect of B7-DC-Ig Dose Dependent on Tumor Eradication

Balb/C mice at age of 9 to 11 weeks were implanted subcutaneously with $1.0 \times 10^5$ CT26 colorectal tumor cells. On day 9 post tumor implantation, mice received a single dose of cyclophosphamide (100 mg/kg) and started treatment on Day 10 with 30, 100 or 300 µg of B7-DC-Ig, 2 doses per week for 4 weeks, total 8 doses. FIG. 6 shows there were 70% of the mice eradicated the tumors at 300 µg, 40% tumor eradication with 100 µg, and 30 µg dose gave rise to 10% tumor eradication.

Example 8

Combination of Cyclophosphamide and Anti-PD-1 can Eradicate Established Tumors

Balb/C mice at age of 9 to 11 weeks were challenged subcutaneously with $1.0 \times 10^5$ CT26 colorectal tumor cells. On day 11 post tumor challenge, mice received a single dose of cyclophosphamide (100 mg/kg) and started treatment with anti-PD-1 antibody (250 ug, Clone G4, Hirano F. et al., 2005 Cancer Research) which was administered 3 times per week for four weeks. 70% of the mice that received the CTX+anti-PD-1 regimen eradicated established CT26 tumors at day 50 after tumor challenge, whereas all mice in the control and anti-PD-1 alone groups died as a result of tumor growth or were euthanized because tumors exceeded the sizes approved by IACUC. These results show the effectiveness of the treatment regimen on established tumors and not mere prophylaxis. Results are shown in FIG. 7.

Example 9

Combination of Cyclophosphamide and Anti-CTLA4 can Eradicate Established Tumors

Balb/C mice at age of 9 to 11 weeks were challenged subcutaneously with $1.0 \times 10^5$ CT26 colorectal tumor cells. On day 11 post tumor challenge, mice received 100 mg/kg of cyclophosphamide. Anti-CTLA4 (an anti-mouse CTLA4 from hamster hybridoma—ATCC deposit UC10-4F10-11) treatment was started 1 day later, on day 12. Mice were treated with 100 ug of anti-CTLA4, 2 doses per week, for 4 weeks. 56% of the mice that received the CTX+anti-CTLA4 regimen were tumor free at day 50 after tumor challenge, whereas all mice in the control group died as a result of tumor growth or were euthanized because tumors exceeded the sizes approved by IACUC. Results are shown in FIG. 8. These results show the effectiveness of the treatment regimen on established tumors and not mere prophylaxis.

Example 10

Combination of Cyclophosphamide and B7-DC-Ig Regimen Leads to Reduction of Tregs in the Tumor Microenvironment FIG. 9 shows the results of experiments wherein Balb/C mice at age of 9 to 11 weeks of age were implanted with $1 \times 10^5$ CT26 cells subcutaneously. On Day 9, mice were injected with 100 mg/kg of CTX, IP. Twenty four hours later, on Day 10, mice were treated with 100 ug of B7-DC-Ig. There were 5 groups: naïve mice that did not receive any tumor cells, vehicle injected, CTX alone, CTX+B7-DC-Ig or B7-DC-Ig alone. Two naïve mice and 4 mice from other groups were removed from the study on Day 11 (2 days post CTX) and Day 16 (7 days post CTX) for T cell analysis. Left panel shows on Day 11, 2 days post CTX injection, Treg in the spleen of the mice with CTX treatment was significantly lower than the one in the mice with tumor implantation and injected with vehicle. Right panel shows that on Day 16, 7 days post CTX and 6 days post B7-DC-Ig treatment, B7-DC-Ig significantly lowered the CD4+ T cells expressing high PD-1. This was observed in both the B7-DC-Ig treated and CTX+B7-DC-Ig treated mice. Mice implanted with tumor cells intended to have more PD-1+/CD4+ T cells in the draining LN compared with naïve mice.

Example 11

Combination of Cyclophosphamide and B7-DC-Ig can Promote Mouse Survival in a Metastatic Prostate Tumor Model B10.D2 mice at age of 9 to 11 weeks were injected intravenously with $3.0 \times 10^5$ SP-1 cells, which were isolated from lung metastasis post parent TRAMP cell injection. The CTX mice received 3 doses of CTX, 50 mg/kg, on Day 5, 12 and 19. The B7-DC-Ig treated mice received 3 doses of B7-DC-Ig, 5 mg/kg, on Day 6, 13 and 20. On Day 100, 17% of mice in the control groups, no-treated, CTX alone, B7-DC-Ig alone survived while 43% of the mice received combination of CTX and B7-DC-Ig survived. Results are shown in FIG. 10.

Example 12

Combination of *Listeria* Cancer Vaccine and B7-DC-Ig can Enhance Mouse Survival Post CT26 Liver Implantation Balb/C mice at age of 11-13 weeks were implanted with CT26 cells using a hemispleen injection technique (Yoshimura K et al., 2007, Cancer Research). On Day 10, mice received 1 injection of CTX at 50 mg/kg, IP. Twenty four hours later, on Day 11, mice were treated with recombinant *Listeria* carrying AH1 peptide, an immunodominant epitope of CT26, at $0.1$ $LD_{50}$ ($1 \times 10^7$ CFU), then on Day 14 and 17. Mice were also treated with B7-DC-Ig on Day 11 and then on Day 18. FIG. 11 shows mice without any treatment or treated with CTX and *Listeria* cancer vaccine all died before Day 45. There were 60% of the mice received triple combination, CTX+*Listeria* cancer vaccine and B7-DC-Ig survived.

1. REFERENCE LIST

1. Brode S, Cooke A. Immune-potentiating effects of the chemotherapeutic drug cyclophosphamide. Crit. Rev. Immunol. 2008; 28(2):109-26
2. van der Most R G, Currie A J, Mahendran S, Prosser A, Darabi A, Robinson B W, Nowak A K, Lake R A. Tumor eradication after cyclophosphamide depends on concurrent depletion of regulatory T cells: a role for cycling TNFR2-expressing effector-suppressor T cells in limiting effective chemotherapy. Cancer Immunol. Immunother. 2009 August; 58(8):1219-28
3. Taieb J, Chaput N, Schartz N, Roux S, Novault S, Menard C, Ghiringhelli F, Terme M, Carpentier A F, Darrasse-Jeze G, et al. Chemoimmunotherapy of tumors: cyclophosphamide synergizes with exosome based vaccines. J. Immunol. 2006 Mar. 1; 176(5):2722-9
4. Machiels J P, Reilly R T, Emens L A, Ercolini A M, Lei R Y, Weintraub D, Okoye F I, Jaffee E M. Cyclophosphamide, doxorubicin, and paclitaxel enhance the antitumor immune response of granulocyte/macrophage-colony stimulating factor-secreting whole-cell vaccines in HER-2/neu tolerized mice. Cancer Res. 2001 May 1; 61(9): 3689-97

5. Bass K K, Mastrangelo M J. Immunopotentiation with low-dose cyclophosphamide in the active specific immunotherapy of cancer. Cancer Immunol. Immunother. 1998 September; 47(1):1-12
6. Hengst J C, Mokyr M B, Dray S. Cooperation between cyclophosphamide tumoricidal activity and host antitumor immunity in the cure of mice bearing large MOPC-315 tumors. Cancer Res. 1981 June; 41(6):2163-7
7. Hengst J C, Mokyr M B, Dray S. Importance of timing in cyclophosphamide therapy of MOPC-315 tumor-bearing mice. Cancer Res. 1980 July; 40(7):2135-41
8. Tsung K, Meko J B, Tsung Y L, Peplinski G R, Norton J A. Immune response against large tumors eradicated by treatment with cyclophosphamide and IL-12. J. Immunol. 1998 Feb. 1; 160(3):1369-77
9. Honeychurch J, Glennie M J, Illidge T M. Cyclophosphamide inhibition of anti-CD40 monoclonal antibody-based therapy of B cell lymphoma is dependent on CD11b+ cells. Cancer Res. 2005 Aug. 15; 65(16):7493-501
10. Wada S, Yoshimura K, Hipkiss E L, Harris T J, Yen H R, Goldberg M V, Grosso J F, Getnet D, Demarzo A M, Netto G J, Anders R, Pardoll D M, Drake C G. Cyclophosphamide augments antitumor immunity: studies in an autochthonous prostate cancer model. Cancer Res. 2009 May 15; 69(10):4309-18.
11. Freeman, G. J. Structures of PD-1 with its ligands: sideways and dancing cheek to cheek. Proc. Natl. Acad. Sci. U.S.A 105, 10275-10276 (2008).
12. Brode, S. & Cooke, A. Immune-potentiating effects of the chemotherapeutic drug cyclophosphamide. Crit. Rev. Immunol. 28, 109-126 (2008).
13. van der Most, R. G. et al. Tumor eradication after cyclophosphamide depends on concurrent depletion of regulatory T cells: a role for cycling TNFR2-expressing effector-suppressor T cells in limiting effective chemotherapy. Cancer Immunol. Immunother. 58, 1219-1228 (2009).
14. Taieb, J. et al. Chemoimmunotherapy of tumors: cyclophosphamide synergizes with exosome based vaccines. J. Immunol. 176, 2722-2729 (2006).
15. Bass, K. K. & Mastrangelo, M. J. Immunopotentiation with low-dose cyclophosphamide in the active specific immunotherapy of cancer. Cancer Immunol. Immunother. 47, 1-12 (1998).
16. Machiels, J. P. et al. Cyclophosphamide, doxorubicin, and paclitaxel enhance the antitumor immune response of granulocyte/macrophage-colony stimulating factor-secreting whole-cell vaccines in HER-2/neu tolerized mice. Cancer Res. 61, 3689-3697 (2001).
17. Hengst, J. C., Mokyr, M. B., & Dray, S. Cooperation between cyclophosphamide tumoricidal activity and host antitumor immunity in the cure of mice bearing large MOPC-315 tumors. Cancer Res. 41, 2163-2167 (1981).
18. Hengst, J. C., Mokyr, M. B., & Dray, S. Importance of timing in cyclophosphamide therapy of MOPC-315 tumor-bearing mice. Cancer Res. 40, 2135-2141 (1980).
19. Tsung, K., Meko, J. B., Tsung, Y. L., Peplinski, G. R., & Norton, J. A. Immune response against large tumors eradicated by treatment with cyclophosphamide and IL-12. J. Immunol. 160, 1369-1377 (1998).
20. Honeychurch, J., Glennie, M. J., & Illidge, T. M. Cyclophosphamide inhibition of anti-CD40 monoclonal antibody-based therapy of B cell lymphoma is dependent on CD11b+ cells. Cancer Res. 65, 7493-7501 (2005).
21. Wada S, Yoshimura K, Hipkiss E L, Harris T J, Yen H R, Goldberg M V, Grosso J F, Getnet D, Demarzo A M, Netto G J, Anders R, Pardoll D M, Drake C G. Cyclophosphamide augments antitumor immunity: studies in an autochthonous prostate cancer model. Cancer Res. 2009 May 15; 69(10):4309-18.

What is claimed is:

1. A method of increasing a T cell response in a human subject comprising administering to the subject an anti-B7-H1 antibody or an antigen binding fragment thereof in combination with a potentiating agent selected from the group consisting of cyclophosphamide and an analog of cyclophosphamide,
   wherein the administration of the anti-B7-H1 antibody or antigen binding fragment thereof in combination with the potentiating agent increases a T cell response,
   wherein the dose of the potentiating agent is less than 200 mg/kg,
   wherein the dose of the potentiating agent is not effective to have direct anti-tumor activity,
   and wherein the T cell response achieved by the combination of the anti-B7-H1 antibody and the potentiating agent is greater than the T cell response achieved by administering either the anti-B7-H1 antibody alone or the potentiating agent alone.

2. The method of claim 1 wherein the anti-B7-H1 antibody or antigen binding fragment thereof inhibits, reduces, modulates or abolishes signal transduction mediated by PD-1.

3. The method of claim 1 wherein the anti-B7-H1 antibody is a human anti-B7-H1 antibody or antigen binding fragment thereof.

4. The method of claim 1 wherein the antigen binding fragment is a Fab, F(ab')₂, or Fv fragment.

5. The method of claim 1 wherein the anti-B7-H1 antibody or antigen binding fragment thereof is a humanized, chimeric, or single-chain antibody or fragment thereof.

6. The method of claim 1 wherein the potentiating agent reduces the activity of regulatory T lymphocytes (Tregs).

7. The method of claim 1 wherein the amount of potentiating agent is sub-therapeutic in the absence of the anti-B7-H1 antibody or an antigen binding fragment thereof.

8. The method of claim 1 wherein the dose of the potentiating agent is 8 mg/kg of cyclophosphamide or an analog of cyclophosphamide.

9. The method of claim 1 further comprising administering an additional immunomodulatory agent.

10. The method of claim 1 further comprising administering an additional agent selected from the group consisting of an anti-CTLA4 antibody, a mitosis inhibitor, an aromatase inhibitor, an A2a adenosine receptor (A2AR) antagonist, anti-PD-1 antibody, and an angiogenesis inhibitor.

11. The method of claim 10 wherein the angiogenesis inhibitor is a VEGF inhibitor.

12. The method of claim 11 wherein the VEGF inhibitor is bevacizumab or VEGF-Trap.

13. The method of claim 1 wherein the potentiating agent is administered before the anti-B7-H1 antibody or antigen binding fragment thereof.

14. The method of claim 13 wherein the potentiating agent is administered at least 1, 2, 3, 5, 10, 15, 20, 24, or 30 hours before the anti-B7-H1 antibody or antigen binding fragment thereof.

15. The method of claim 1 wherein the anti-B7-H1 antibody or antigen binding fragment thereof and the potentiating agent are administered in an amount effective to treat, inhibit, or alleviate one or more symptoms of cancer by an increased T cell-mediated immune response.

16. The method of claim 15 wherein the cancer is selected from the group consisting of a bladder, brain, breast, cervical, colo-rectal, esophageal, kidney, liver, lung, nasopharangeal, pancreatic, prostate, skin, stomach, uterine, ovarian, testicular, and hematologic cancer.

17. The method of claim 15 wherein the cancer is selected from the group consisting of gastric cancer, glioma, leukemia, melanoma, multiple myeloma, renal cell carcinoma, and urothelial cancer.

18. The method of claim 17 wherein the cancer is melanoma.

19. A pharmaceutical dosage unit comprising an anti-B7-H1 antibody or an antigen binding fragment thereof and a potentiating agent selected from the group consisting of cyclophosphamide and an analog of cyclophosphamide,
   wherein administration of the dosage unit to a subject increases a T cell response in the subject,
   wherein the dose of the potentiating agent is less than 200 mg/kg,
   wherein the dose of potentiating agent is not effective to have direct anti-tumor activity,
   and wherein the T cell response achieved by the dosage unit is greater than the T cell response achieved by administering either the anti-B7-H1 antibody alone or the potentiating agent alone.

20. A method of increasing T cell response in a human comprising administering to a human the pharmaceutical dosage unit of claim 19.

21. The pharmaceutical dosage unit of claim 19 further comprising an antigen.

22. The method of claim 15 wherein the T cell response against the cancer achieved by the combination of the anti-B7-H1 antibody and the potentiating agent is greater than the T cell response against the cancer achieved by administering either the anti-B7-H1 antibody alone or the potentiating agent alone.

23. The method of claim 1 wherein the dosage of potentiating agent is 5 mg/kg.

* * * * *

UNITED STATES PATENT AND TRADEMARK OFFICE
CERTIFICATE OF CORRECTION

| | | |
|---|---|---|
| PATENT NO. | : 8,609,089 B2 | Page 1 of 1 |
| APPLICATION NO. | : 13/332154 | |
| DATED | : December 17, 2013 | |
| INVENTOR(S) | : Solomon Langermann and Linda Liu | |

It is certified that error appears in the above-identified patent and that said Letters Patent is hereby corrected as shown below:

In the Claims

Column 80, claim 20, line 13, replace "increasing T cell" with --increasing a T cell--.

Signed and Sealed this
Twenty-first Day of October, 2014

Michelle K. Lee
*Deputy Director of the United States Patent and Trademark Office*

SEQUENCE LISTING

```
<160> NUMBER OF SEQ ID NOS: 20

<210> SEQ ID NO 1
<211> LENGTH: 273
<212> TYPE: PRT
<213> ORGANISM: Homo sapiens

<400> SEQUENCE: 1

Met Ile Phe Leu Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
            20                  25                  30

Glu His Gly Ser Asn Val Thr Leu Glu Cys Asn Phe Asp Thr Gly Ser
        35                  40                  45

His Val Asn Leu Gly Ala Ile Thr Ala Ser Leu Gln Lys Val Glu Asn
    50                  55                  60

Asp Thr Ser Pro His Arg Glu Arg Ala Thr Leu Leu Glu Glu Gln Leu
65                  70                  75                  80

Pro Leu Gly Lys Ala Ser Phe His Ile Pro Gln Val Gln Val Arg Asp
                85                  90                  95

Glu Gly Gln Tyr Gln Cys Ile Ile Ile Tyr Gly Val Ala Trp Asp Tyr
            100                 105                 110

Lys Tyr Leu Thr Leu Lys Val Lys Ala Ser Tyr Arg Lys Ile Asn Thr
        115                 120                 125
```

```
His Ile Leu Lys Val Pro Glu Thr Asp Glu Val Glu Leu Thr Cys Gln
            130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Gly Arg Asn Phe Ser Cys
            180                 185                 190

Val Phe Trp Asn Thr His Val Arg Glu Leu Thr Leu Ala Ser Ile Asp
        195                 200                 205

Leu Gln Ser Gln Met Glu Pro Arg Thr His Pro Thr Trp Leu Leu His
    210                 215                 220

Ile Phe Ile Pro Phe Cys Ile Ile Ala Phe Ile Phe Ile Ala Thr Val
225                 230                 235                 240

Ile Ala Leu Arg Lys Gln Leu Cys Gln Lys Leu Tyr Ser Ser Lys Asp
                245                 250                 255

Thr Thr Lys Arg Pro Val Thr Thr Lys Arg Glu Val Asn Ser Ala
            260                 265                 270

Ile

<210> SEQ ID NO 2
<211> LENGTH: 254
<212> TYPE: PRT
<213> ORGANISM: Homo sapiens

<400> SEQUENCE: 2

Leu Phe Thr Val Thr Val Pro Lys Glu Leu Tyr Ile Ile Glu His Gly
1               5                   10                  15

Ser Asn Val Thr Leu Glu Cys Asn Phe Asp Thr Gly Ser His Val Asn
            20                  25                  30

Leu Gly Ala Ile Thr Ala Ser Leu Gln Lys Val Glu Asn Asp Thr Ser
        35                  40                  45

Pro His Arg Glu Arg Ala Thr Leu Leu Glu Glu Gln Leu Pro Leu Gly
    50                  55                  60

Lys Ala Ser Phe His Ile Pro Gln Val Gln Val Arg Asp Glu Gly Gln
65                  70                  75                  80

Tyr Gln Cys Ile Ile Ile Tyr Gly Val Ala Trp Asp Tyr Lys Tyr Leu
                85                  90                  95

Thr Leu Lys Val Lys Ala Ser Tyr Arg Lys Ile Asn Thr His Ile Leu
            100                 105                 110

Lys Val Pro Glu Thr Asp Glu Val Glu Leu Thr Cys Gln Ala Thr Gly
        115                 120                 125

Tyr Pro Leu Ala Glu Val Ser Trp Pro Asn Val Ser Val Pro Ala Asn
    130                 135                 140

Thr Ser His Ser Arg Thr Pro Glu Gly Leu Tyr Gln Val Thr Ser Val
145                 150                 155                 160

Leu Arg Leu Lys Pro Pro Gly Arg Asn Phe Ser Cys Val Phe Trp
                165                 170                 175

Asn Thr His Val Arg Glu Leu Thr Leu Ala Ser Ile Asp Leu Gln Ser
            180                 185                 190

Gln Met Glu Pro Arg Thr His Pro Thr Trp Leu Leu His Ile Phe Ile
        195                 200                 205

Pro Phe Cys Ile Ile Ala Phe Ile Phe Ile Ala Thr Val Ile Ala Leu
    210                 215                 220

Arg Lys Gln Leu Cys Gln Lys Leu Tyr Ser Ser Lys Asp Thr Thr Lys
```

```
                225                 230                 235                 240
Arg Pro Val Thr Thr Lys Arg Glu Val Asn Ser Ala Ile
                245                 250

<210> SEQ ID NO 3
<211> LENGTH: 202
<212> TYPE: PRT
<213> ORGANISM: Homo sapiens

<400> SEQUENCE: 3

Leu Phe Thr Val Thr Val Pro Lys Glu Leu Tyr Ile Ile Glu His Gly
1               5                   10                  15

Ser Asn Val Thr Leu Glu Cys Asn Phe Asp Thr Gly Ser His Val Asn
            20                  25                  30

Leu Gly Ala Ile Thr Ala Ser Leu Gln Lys Val Glu Asn Asp Thr Ser
        35                  40                  45

Pro His Arg Glu Arg Ala Thr Leu Leu Glu Glu Gln Leu Pro Leu Gly
    50                  55                  60

Lys Ala Ser Phe His Ile Pro Gln Val Gln Val Arg Asp Glu Gly Gln
65                  70                  75                  80

Tyr Gln Cys Ile Ile Ile Tyr Gly Val Ala Trp Asp Tyr Lys Tyr Leu
                85                  90                  95

Thr Leu Lys Val Lys Ala Ser Tyr Arg Lys Ile Asn Thr His Ile Leu
            100                 105                 110

Lys Val Pro Glu Thr Asp Glu Val Glu Leu Thr Cys Gln Ala Thr Gly
        115                 120                 125

Tyr Pro Leu Ala Glu Val Ser Trp Pro Asn Val Ser Val Pro Ala Asn
    130                 135                 140

Thr Ser His Ser Arg Thr Pro Glu Gly Leu Tyr Gln Val Thr Ser Val
145                 150                 155                 160

Leu Arg Leu Lys Pro Pro Pro Gly Arg Asn Phe Ser Cys Val Phe Trp
                165                 170                 175

Asn Thr His Val Arg Glu Leu Thr Leu Ala Ser Ile Asp Leu Gln Ser
            180                 185                 190

Gln Met Glu Pro Arg Thr His Pro Thr Trp
        195                 200

<210> SEQ ID NO 4
<211> LENGTH: 202
<212> TYPE: PRT
<213> ORGANISM: murine

<400> SEQUENCE: 4

Leu Phe Thr Val Thr Ala Pro Lys Glu Val Tyr Thr Val Asp Val Gly
1               5                   10                  15

Ser Ser Val Ser Leu Glu Cys Asp Phe Asp Arg Arg Glu Cys Thr Glu
            20                  25                  30

Leu Glu Gly Ile Arg Ala Ser Leu Gln Lys Val Glu Asn Asp Thr Ser
        35                  40                  45

Leu Gln Ser Glu Arg Ala Thr Leu Leu Glu Glu Gln Leu Pro Leu Gly
    50                  55                  60

Lys Ala Leu Phe His Ile Pro Ser Val Gln Val Arg Asp Ser Gly Gln
65                  70                  75                  80

Tyr Arg Cys Leu Val Ile Cys Gly Ala Ala Trp Asp Tyr Lys Tyr Leu
                85                  90                  95

Thr Val Lys Val Lys Ala Ser Tyr Met Arg Ile Asp Thr Arg Ile Leu
            100                 105                 110
```

```
Glu Val Pro Gly Thr Gly Glu Val Gln Leu Thr Cys Gln Ala Arg Gly
            115                 120                 125

Tyr Pro Leu Ala Glu Val Ser Trp Gln Asn Val Ser Val Pro Ala Asn
        130                 135                 140

Thr Ser His Ile Arg Thr Pro Glu Gly Leu Tyr Gln Val Thr Ser Val
145                 150                 155                 160

Leu Arg Leu Lys Pro Gln Pro Ser Arg Asn Phe Ser Cys Met Phe Trp
                165                 170                 175

Asn Ala His Met Lys Glu Leu Thr Ser Ala Ile Ile Asp Pro Leu Ser
            180                 185                 190

Arg Met Glu Pro Lys Val Pro Arg Thr Trp
        195                 200

<210> SEQ ID NO 5
<211> LENGTH: 19
<212> TYPE: PRT
<213> ORGANISM: Homo sapiens

<400> SEQUENCE: 5

Met Ile Phe Leu Leu Leu Met Leu Ser Leu Glu Leu Gln Leu His Gln
1               5                   10                  15

Ile Ala Ala

<210> SEQ ID NO 6
<211> LENGTH: 232
<212> TYPE: PRT
<213> ORGANISM: Homo sapiens

<400> SEQUENCE: 6

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
```

```
                    210                 215                 220
Ser Leu Ser Leu Ser Pro Gly Lys
225                 230

<210> SEQ ID NO 7
<211> LENGTH: 233
<212> TYPE: PRT
<213> ORGANISM: murine

<400> SEQUENCE: 7

Glu Pro Arg Gly Pro Thr Ile Lys Pro Cys Pro Pro Cys Lys Cys Pro
1               5                   10                  15

Ala Pro Asn Leu Leu Gly Gly Pro Ser Val Phe Ile Phe Pro Pro Lys
                20                  25                  30

Ile Lys Asp Val Leu Met Ile Ser Leu Ser Pro Ile Val Thr Cys Val
            35                  40                  45

Val Val Asp Val Ser Glu Asp Asp Pro Asp Val Gln Ile Ser Trp Phe
50                  55                  60

Val Asn Asn Val Glu Val His Thr Ala Gln Thr Gln Thr His Arg Glu
65                  70                  75                  80

Asp Tyr Asn Ser Thr Leu Arg Val Val Ser Ala Leu Pro Ile Gln His
                85                  90                  95

Gln Asp Trp Met Ser Gly Lys Glu Phe Lys Cys Lys Val Asn Asn Lys
            100                 105                 110

Asp Leu Pro Ala Pro Ile Glu Arg Thr Ile Ser Lys Pro Lys Gly Ser
        115                 120                 125

Val Arg Ala Pro Gln Val Tyr Val Leu Pro Pro Pro Glu Glu Glu Met
130                 135                 140

Thr Lys Lys Gln Val Thr Leu Thr Cys Met Val Thr Asp Phe Met Pro
145                 150                 155                 160

Glu Asp Ile Tyr Val Glu Trp Thr Asn Asn Gly Lys Thr Glu Leu Asn
                165                 170                 175

Tyr Lys Asn Thr Glu Pro Val Leu Asp Ser Asp Gly Ser Tyr Phe Met
            180                 185                 190

Tyr Ser Lys Leu Arg Val Glu Lys Lys Asn Trp Val Glu Arg Asn Ser
        195                 200                 205

Tyr Ser Cys Ser Val Val His Glu Gly Leu His Asn His His Thr Thr
210                 215                 220

Lys Ser Phe Ser Arg Thr Pro Gly Lys
225                 230

<210> SEQ ID NO 8
<211> LENGTH: 1365
<212> TYPE: DNA
<213> ORGANISM: artificial
<220> FEATURE:
<223> OTHER INFORMATION: Murine B7-DC-Ig

<400> SEQUENCE: 8
atgctgctcc tgctgccgat actgaacctg agcttacaac ttcatcctgt agcagcttta      60
ttcaccgtga cagcccctaa agaagtgtac accgtagacg tcggcagcag tgtgagcctg     120
gagtgcgatt ttgaccgcag agaatgcact gaactggaag ggataagagc cagtttgcag     180
aaggtagaaa atgatacgtc tctgcaaagt gaaagagcca ccctgctgga ggagcagctg     240
cccctgggaa aggctttgtt ccacatccct agtgtccaag tgagagattc cgggcagtac     300
cgttgcctgg tcatctgcgg ggccgcctgg gactacaagt acctgacggt gaaagtcaaa     360
```

```
gcttcttaca tgaggataga cactaggatc ctggaggttc caggtacagg ggaggtgcag    420
cttacctgcc aggctagagg ttatcccta gcagaagtgt cctggcaaaa tgtcagtgtt    480
cctgccaaca ccagccacat caggacccc gaaggcctct accaggtcac cagtgttctg    540
cgcctcaagc ctcagcctag cagaaacttc agctgcatgt tctggaatgc tcacatgaag    600
gagctgactt cagccatcat tgaccctctg agtcggatgg aacccaaagt ccccagaacg    660
tgggagccaa gaggtcctac gatcaagccc tgcccgcctt gtaaatgccc agctccaaat    720
ttgctgggtg accgtcagt ctttatcttc ccgccaaaga taaggacgt cttgatgatt    780 agtctgagcc ccatcgtgac atgcgttgtg gtggatgttt cagaggatga ccccgacgtg    840
caaatcagtt ggttcgttaa caacgtggag gtgcataccg ctcaaaccca gacccacaga    900
gaggattata acagcaccct gcgggtagtg tccgccctgc cgatccagca tcaggattgg    960
atgagcggga aagagttcaa gtgtaaggta acaacaaag atctgccagc gccgattgaa   1020
cgaaccatta gcaagccgaa agggagcgtg cgcgcacctc aggtttacgt ccttcctcca   1080
ccagaagagg agatgacgaa aaagcaggtg accctgacat gcatggtaac tgactttatg   1140
ccagaagata tttacgtgga atggactaat aacggaaaga cagagctcaa ttacaagaac   1200
actgagcctg ttctggattc tgatggcagc tactttatgt actccaaatt gagggtcgag   1260
aagaagaatt gggtcgagag aaacagttat agttgctcag tggtgcatga gggcctccat   1320
aatcatcaca ccacaaagtc cttcagccga acgcccggga atga                    1365
```

<210> SEQ ID NO 9
<211> LENGTH: 454
<212> TYPE: PRT
<213> ORGANISM: artificial
<220> FEATURE:
<223> OTHER INFORMATION: Murine B7-DC-Ig

<400> SEQUENCE: 9

```
Met Leu Leu Leu Leu Pro Ile Leu Asn Leu Ser Leu Gln Leu His Pro
1               5                   10                  15

Val Ala Ala Leu Phe Thr Val Thr Ala Pro Lys Glu Val Tyr Thr Val
            20                  25                  30

Asp Val Gly Ser Ser Val Ser Leu Glu Cys Asp Phe Asp Arg Arg Glu
        35                  40                  45

Cys Thr Glu Leu Glu Gly Ile Arg Ala Ser Leu Gln Lys Val Glu Asn
    50                  55                  60

Asp Thr Ser Leu Gln Ser Glu Arg Ala Thr Leu Leu Glu Glu Gln Leu
65                  70                  75                  80

Pro Leu Gly Lys Ala Leu Phe His Ile Pro Ser Val Gln Val Arg Asp
                85                  90                  95

Ser Gly Gln Tyr Arg Cys Leu Val Ile Cys Gly Ala Ala Trp Asp Tyr
            100                 105                 110

Lys Tyr Leu Thr Val Lys Val Lys Ala Ser Tyr Met Arg Ile Asp Thr
        115                 120                 125

Arg Ile Leu Glu Val Pro Gly Thr Gly Glu Val Gln Leu Thr Cys Gln
    130                 135                 140

Ala Arg Gly Tyr Pro Leu Ala Glu Val Ser Trp Gln Asn Val Ser Val
145                 150                 155                 160

Pro Ala Asn Thr Ser His Ile Arg Thr Pro Glu Gly Leu Tyr Gln Val
                165                 170                 175

Thr Ser Val Leu Arg Leu Lys Pro Gln Pro Ser Arg Asn Phe Ser Cys
            180                 185                 190
```

```
Met Phe Trp Asn Ala His Met Lys Glu Leu Thr Ser Ala Ile Ile Asp
            195                 200                 205

Pro Leu Ser Arg Met Glu Pro Lys Val Pro Arg Thr Trp Glu Pro Arg
        210                 215                 220

Gly Pro Thr Ile Lys Pro Cys Pro Pro Cys Lys Cys Pro Ala Pro Asn
225                 230                 235                 240

Leu Leu Gly Gly Pro Ser Val Phe Ile Phe Pro Pro Lys Ile Lys Asp
                245                 250                 255

Val Leu Met Ile Ser Leu Ser Pro Ile Val Thr Cys Val Val Val Asp
                260                 265                 270

Val Ser Glu Asp Asp Pro Asp Val Gln Ile Ser Trp Phe Val Asn Asn
            275                 280                 285

Val Glu Val His Thr Ala Gln Thr Gln Thr His Arg Glu Asp Tyr Asn
        290                 295                 300

Ser Thr Leu Arg Val Val Ser Ala Leu Pro Ile Gln His Gln Asp Trp
305                 310                 315                 320

Met Ser Gly Lys Glu Phe Lys Cys Lys Val Asn Asn Lys Asp Leu Pro
                325                 330                 335

Ala Pro Ile Glu Arg Thr Ile Ser Lys Pro Lys Gly Ser Val Arg Ala
            340                 345                 350

Pro Gln Val Tyr Val Leu Pro Pro Glu Glu Glu Met Thr Lys Lys
        355                 360                 365

Gln Val Thr Leu Thr Cys Met Val Thr Asp Phe Met Pro Glu Asp Ile
    370                 375                 380

Tyr Val Glu Trp Thr Asn Asn Gly Lys Thr Glu Leu Asn Tyr Lys Asn
385                 390                 395                 400

Thr Glu Pro Val Leu Asp Ser Asp Gly Ser Tyr Phe Met Tyr Ser Lys
                405                 410                 415

Leu Arg Val Glu Lys Lys Asn Trp Val Glu Arg Asn Ser Tyr Ser Cys
            420                 425                 430

Ser Val Val His Glu Gly Leu His Asn His Thr Thr Lys Ser Phe
        435                 440                 445

Ser Arg Thr Pro Gly Lys
    450

<210> SEQ ID NO 10
<211> LENGTH: 435
<212> TYPE: PRT
<213> ORGANISM: artificial
<220> FEATURE:
<223> OTHER INFORMATION: Murine B7-DC-Ig fusion protein without signal
      sequence

<400> SEQUENCE: 10

Leu Phe Thr Val Thr Ala Pro Lys Glu Val Tyr Thr Val Asp Val Gly
1               5                   10                  15

Ser Ser Val Ser Leu Glu Cys Asp Phe Asp Arg Arg Glu Cys Thr Glu
                20                  25                  30

Leu Glu Gly Ile Arg Ala Ser Leu Gln Lys Val Glu Asn Asp Thr Ser
            35                  40                  45

Leu Gln Ser Glu Arg Ala Thr Leu Leu Glu Glu Gln Leu Pro Leu Gly
        50                  55                  60

Lys Ala Leu Phe His Ile Pro Ser Val Gln Val Arg Asp Ser Gly Gln
65                  70                  75                  80

Tyr Arg Cys Leu Val Ile Cys Gly Ala Ala Trp Asp Tyr Lys Tyr Leu
                85                  90                  95
```

Thr Val Lys Val Lys Ala Ser Tyr Met Arg Ile Asp Thr Arg Ile Leu
            100                 105                 110
Glu Val Pro Gly Thr Gly Glu Val Gln Leu Thr Cys Gln Ala Arg Gly
        115                 120                 125
Tyr Pro Leu Ala Glu Val Ser Trp Gln Asn Val Ser Val Pro Ala Asn
    130                 135                 140
Thr Ser His Ile Arg Thr Pro Glu Gly Leu Tyr Gln Val Thr Ser Val
145                 150                 155                 160
Leu Arg Leu Lys Pro Gln Pro Ser Arg Asn Phe Ser Cys Met Phe Trp
                165                 170                 175
Asn Ala His Met Lys Glu Leu Thr Ser Ala Ile Ile Asp Pro Leu Ser
            180                 185                 190
Arg Met Glu Pro Lys Val Pro Arg Thr Trp Glu Pro Arg Gly Pro Thr
        195                 200                 205
Ile Lys Pro Cys Pro Pro Cys Lys Cys Pro Ala Pro Asn Leu Leu Gly
    210                 215                 220
Gly Pro Ser Val Phe Ile Phe Pro Pro Lys Ile Lys Asp Val Leu Met
225                 230                 235                 240
Ile Ser Leu Ser Pro Ile Val Thr Cys Val Val Val Asp Val Ser Glu
                245                 250                 255
Asp Asp Pro Asp Val Gln Ile Ser Trp Phe Val Asn Asn Val Glu Val
            260                 265                 270
His Thr Ala Gln Thr Gln Thr His Arg Glu Asp Tyr Asn Ser Thr Leu
        275                 280                 285
Arg Val Val Ser Ala Leu Pro Ile Gln His Gln Asp Trp Met Ser Gly
    290                 295                 300
Lys Glu Phe Lys Cys Lys Val Asn Asn Lys Asp Leu Pro Ala Pro Ile
305                 310                 315                 320
Glu Arg Thr Ile Ser Lys Pro Lys Gly Ser Val Arg Ala Pro Gln Val
                325                 330                 335
Tyr Val Leu Pro Pro Pro Glu Glu Glu Met Thr Lys Lys Gln Val Thr
            340                 345                 350
Leu Thr Cys Met Val Thr Asp Phe Met Pro Glu Asp Ile Tyr Val Glu
        355                 360                 365
Trp Thr Asn Asn Gly Lys Thr Glu Leu Asn Tyr Lys Asn Thr Glu Pro
    370                 375                 380
Val Leu Asp Ser Asp Gly Ser Tyr Phe Met Tyr Ser Lys Leu Arg Val
385                 390                 395                 400
Glu Lys Lys Asn Trp Val Glu Arg Asn Ser Tyr Ser Cys Ser Val Val
                405                 410                 415
His Glu Gly Leu His Asn His His Thr Thr Lys Ser Phe Ser Arg Thr
            420                 425                 430
Pro Gly Lys
        435

<210> SEQ ID NO 11
<211> LENGTH: 1362
<212> TYPE: DNA
<213> ORGANISM: artificial
<220> FEATURE:
<223> OTHER INFORMATION: Human B7-DC-Ig

<400> SEQUENCE: 11
atgatctttc ttctcttgat gctgtctttg gaattgcaac ttcaccaaat cgcggccctc      60
tttactgtga ccgtgccaaa agaactgtat atcattgagc acgggtccaa tgtgacccte     120

```
gaatgtaact tgacaccgg cagccacgtt aacctggggg ccatcactgc cagcttgcaa      180
aaagttgaaa acgacacttc acctcaccgg gagagggcaa ccctcttgga ggagcaactg      240
ccattgggga aggcctcctt tcatatccct caggtgcagg ttcgggatga gggacagtac      300
cagtgcatta ttatctacgg cgtggcttgg gattacaagt atctgaccct gaaggtgaaa      360
gcgtcctatc ggaaaattaa cactcacatt cttaaggtgc cagagacgga cgaggtggaa      420
ctgacatgcc aagccaccgg ctacccgttg gcagaggtca gctggcccaa cgtgagcgta      480
cctgctaaca cttctcattc taggacaccc gagggcctct accaggttac atccgtgctc      540
cgcctcaaac cgccccccagg ccggaatttt agttgcgtgt tttggaatac ccacgtgcga      600
gagctgactc ttgcatctat tgatctgcag tcccagatgg agccacggac tcatccaact      660
tgggaaccta atcttgcga taaaactcat acctgtcccc cttgcccagc ccccgagctt      720
ctgggaggtc ccagtgtgtt tctgtttccc ccaaaaccta aggacacact tatgatatcc      780
cgaacgccgg aagtgacatg cgtggttgtg gacgtctcac acgaagaccc ggaggtgaaa      840
ttcaactggt acgttgacgg agttgaggtt cataacgcta agaccaagcc cagagaggag      900
caatacaatt ccacctatcg agtggttagt gtactgaccg ttttgcacca agactggctg      960
aatggaaaag aatacaagtg caaagtatca acaaggcttt gcctgcacc catcgagaag     1020 acaatttcta aagccaaagg gcagcccagg gaaccgcagg tgtacacact cccaccatcc     1080
cgcgacgagc tgacaaagaa tcaagtatcc ctgacctgcc tggtgaaagg cttttaccca     1140
tctgacattg ccgtggaatg ggaatcaaat ggacaacctg agaacaacta caaaaccact     1200
ccacctgtgc ttgacagcga cgggtccttt ttcctgtaca gtaagctcac tgtcgataag     1260
tctcgctggc agcagggcaa cgtcttttca tgtagtgtga tgcacgaagc tctgcacaac     1320
cattcacccc agaagtctct gtcactgagc ccaggtaaat ga                       1362
```

<210> SEQ ID NO 12
<211> LENGTH: 453
<212> TYPE: PRT
<213> ORGANISM: Artificial
<220> FEATURE:
<223> OTHER INFORMATION: Human B7-DC-Ig

<400> SEQUENCE: 12

```
Met Ile Phe Leu Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
            20                  25                  30

Glu His Gly Ser Asn Val Thr Leu Glu Cys Asn Phe Asp Thr Gly Ser
        35                  40                  45

His Val Asn Leu Gly Ala Ile Thr Ala Ser Leu Gln Lys Val Glu Asn
    50                  55                  60

Asp Thr Ser Pro His Arg Glu Arg Ala Thr Leu Leu Glu Glu Gln Leu
65                  70                  75                  80

Pro Leu Gly Lys Ala Ser Phe His Ile Pro Gln Val Gln Val Arg Asp
                85                  90                  95

Glu Gly Gln Tyr Gln Cys Ile Ile Ile Tyr Gly Val Ala Trp Asp Tyr
            100                 105                 110

Lys Tyr Leu Thr Leu Lys Val Lys Ala Ser Tyr Arg Lys Ile Asn Thr
        115                 120                 125

His Ile Leu Lys Val Pro Glu Thr Asp Glu Val Glu Leu Thr Cys Gln
    130                 135                 140

Ala Thr Gly Tyr Pro Leu Ala Glu Val Ser Trp Pro Asn Val Ser Val
```

```
                145                 150                 155                 160
Pro Ala Asn Thr Ser His Ser Arg Thr Pro Glu Gly Leu Tyr Gln Val
                    165                 170                 175

Thr Ser Val Leu Arg Leu Lys Pro Pro Gly Arg Asn Phe Ser Cys
            180                 185                 190

Val Phe Trp Asn Thr His Val Arg Glu Leu Thr Leu Ala Ser Ile Asp
            195                 200                 205

Leu Gln Ser Gln Met Glu Pro Arg Thr His Pro Thr Trp Glu Pro Lys
        210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 13
<211> LENGTH: 434
<212> TYPE: PRT
<213> ORGANISM: Artificial
<220> FEATURE:
<223> OTHER INFORMATION: Human B7-DC-Ig without signal sequence

<400> SEQUENCE: 13

Leu Phe Thr Val Thr Val Pro Lys Glu Leu Tyr Ile Ile Glu His Gly
1               5                   10                  15

Ser Asn Val Thr Leu Glu Cys Asn Phe Asp Thr Gly Ser His Val Asn
            20                  25                  30

Leu Gly Ala Ile Thr Ala Ser Leu Gln Lys Val Glu Asn Asp Thr Ser
        35                  40                  45

Pro His Arg Glu Arg Ala Thr Leu Leu Glu Glu Gln Leu Pro Leu Gly
    50                  55                  60
```

```
Lys Ala Ser Phe His Ile Pro Gln Val Gln Val Arg Asp Glu Gly Gln
 65                  70                  75                  80

Tyr Gln Cys Ile Ile Ile Tyr Gly Val Ala Trp Asp Tyr Lys Tyr Leu
                 85                  90                  95

Thr Leu Lys Val Lys Ala Ser Tyr Arg Lys Ile Asn Thr His Ile Leu
            100                 105                 110

Lys Val Pro Glu Thr Asp Glu Val Glu Leu Thr Cys Gln Ala Thr Gly
        115                 120                 125

Tyr Pro Leu Ala Glu Val Ser Trp Pro Asn Val Ser Val Pro Ala Asn
130                 135                 140

Thr Ser His Ser Arg Thr Pro Glu Gly Leu Tyr Gln Val Thr Ser Val
145                 150                 155                 160

Leu Arg Leu Lys Pro Pro Gly Arg Asn Phe Ser Cys Val Phe Trp
                165                 170                 175

Asn Thr His Val Arg Glu Leu Thr Leu Ala Ser Ile Asp Leu Gln Ser
            180                 185                 190

Gln Met Glu Pro Arg Thr His Pro Thr Trp Glu Pro Lys Ser Cys Asp
        195                 200                 205

Lys Thr His Thr Cys Pro Pro Cys Pro Ala Pro Glu Leu Leu Gly Gly
210                 215                 220

Pro Ser Val Phe Leu Phe Pro Pro Lys Pro Lys Asp Thr Leu Met Ile
225                 230                 235                 240

Ser Arg Thr Pro Glu Val Thr Cys Val Val Val Asp Val Ser His Glu
                245                 250                 255

Asp Pro Glu Val Lys Phe Asn Trp Tyr Val Asp Gly Val Glu Val His
            260                 265                 270

Asn Ala Lys Thr Lys Pro Arg Glu Glu Gln Tyr Asn Ser Thr Tyr Arg
        275                 280                 285

Val Val Ser Val Leu Thr Val Leu His Gln Asp Trp Leu Asn Gly Lys
290                 295                 300

Glu Tyr Lys Cys Lys Val Ser Asn Lys Ala Leu Pro Ala Pro Ile Glu
305                 310                 315                 320

Lys Thr Ile Ser Lys Ala Lys Gly Gln Pro Arg Glu Pro Gln Val Tyr
                325                 330                 335

Thr Leu Pro Pro Ser Arg Asp Glu Leu Thr Lys Asn Gln Val Ser Leu
            340                 345                 350

Thr Cys Leu Val Lys Gly Phe Tyr Pro Ser Asp Ile Ala Val Glu Trp
        355                 360                 365

Glu Ser Asn Gly Gln Pro Glu Asn Asn Tyr Lys Thr Thr Pro Pro Val
370                 375                 380

Leu Asp Ser Asp Gly Ser Phe Phe Leu Tyr Ser Lys Leu Thr Val Asp
385                 390                 395                 400

Lys Ser Arg Trp Gln Gln Gly Asn Val Phe Ser Cys Ser Val Met His
                405                 410                 415

Glu Ala Leu His Asn His Tyr Thr Gln Lys Ser Leu Ser Leu Ser Pro
            420                 425                 430

Gly Lys

<210> SEQ ID NO 14
<211> LENGTH: 5
<212> TYPE: PRT
<213> ORGANISM: Homo sapiens

<400> SEQUENCE: 14
```

Trp Asp Tyr Lys Tyr
1               5

<210> SEQ ID NO 15
<211> LENGTH: 202
<212> TYPE: PRT
<213> ORGANISM: Macaca fascicularis

<400> SEQUENCE: 15

Leu Phe Thr Val Thr Val Pro Lys Glu Leu Tyr Ile Ile Glu His Gly
1               5                   10                  15

Ser Asn Val Thr Leu Glu Cys Asn Phe Asp Thr Gly Ser His Val Asn
            20                  25                  30

Leu Gly Ala Ile Thr Ala Ser Leu Gln Lys Val Glu Asn Asp Thr Ser
        35                  40                  45

Pro His Arg Glu Arg Ala Thr Leu Leu Glu Glu Gln Leu Pro Leu Gly
    50                  55                  60

Lys Ala Ser Phe His Ile Pro Gln Val Gln Val Arg Asp Glu Gly Gln
65                  70                  75                  80

Tyr Gln Cys Ile Ile Ile Tyr Gly Val Ala Trp Asp Tyr Lys Tyr Leu
                85                  90                  95

Thr Leu Lys Val Lys Ala Ser Tyr Arg Lys Ile Asn Thr His Ile Leu
            100                 105                 110

Lys Val Pro Glu Thr Asp Glu Val Glu Leu Thr Cys Gln Ala Thr Gly
        115                 120                 125

Tyr Pro Leu Ala Glu Val Ser Trp Pro Asn Val Ser Val Pro Ala Asn
    130                 135                 140

Thr Ser His Ser Arg Thr Pro Glu Gly Leu Tyr Gln Val Thr Ser Val
145                 150                 155                 160

Leu Arg Leu Lys Pro Pro Pro Gly Arg Asn Phe Ser Cys Val Phe Trp
                165                 170                 175

Asn Thr His Val Arg Glu Leu Thr Leu Ala Ser Ile Asp Leu Gln Ser
            180                 185                 190

Gln Met Glu Pro Arg Thr His Pro Thr Trp
        195                 200

<210> SEQ ID NO 16
<211> LENGTH: 290
<212> TYPE: PRT
<213> ORGANISM: Homo sapiens

<400> SEQUENCE: 16

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val

```
                    115                 120                 125
Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
            195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
            275                 280                 285

Glu Thr
    290

<210> SEQ ID NO 17
<211> LENGTH: 290
<212> TYPE: PRT
<213> ORGANISM: Mus musculus

<400> SEQUENCE: 17

Met Arg Ile Phe Ala Gly Ile Ile Phe Thr Ala Cys Cys His Leu Leu
1               5                   10                  15

Arg Ala Phe Thr Ile Thr Ala Pro Lys Asp Leu Tyr Val Val Glu Tyr
            20                  25                  30

Gly Ser Asn Val Thr Met Glu Cys Arg Phe Pro Val Glu Arg Glu Leu
        35                  40                  45

Asp Leu Leu Ala Leu Val Val Tyr Trp Glu Lys Glu Asp Glu Gln Val
50                  55                  60

Ile Gln Phe Val Ala Gly Glu Glu Asp Leu Lys Pro Gln His Ser Asn
65                  70                  75                  80

Phe Arg Gly Arg Ala Ser Leu Pro Lys Asp Gln Leu Leu Lys Gly Asn
                85                  90                  95

Ala Ala Leu Gln Ile Thr Asp Val Lys Leu Gln Asp Ala Gly Val Tyr
            100                 105                 110

Cys Cys Ile Ile Ser Tyr Gly Gly Ala Asp Tyr Lys Arg Ile Thr Leu
        115                 120                 125

Lys Val Asn Ala Pro Tyr Arg Lys Ile Asn Gln Arg Ile Ser Val Asp
    130                 135                 140

Pro Ala Thr Ser Glu His Glu Leu Ile Cys Gln Ala Glu Gly Tyr Pro
145                 150                 155                 160

Glu Ala Glu Val Ile Trp Thr Asn Ser Asp His Gln Pro Val Ser Gly
                165                 170                 175

Lys Arg Ser Val Thr Thr Ser Arg Thr Glu Gly Met Leu Leu Asn Val
            180                 185                 190

Thr Ser Ser Leu Arg Val Asn Ala Thr Ala Asn Asp Val Phe Tyr Cys
```

```
             195                 200                 205
Thr Phe Trp Arg Ser Gln Pro Gly Gln Asn His Thr Ala Glu Leu Ile
210                 215                 220

Ile Pro Glu Leu Pro Ala Thr His Pro Pro Gln Asn Arg Thr His Trp
225                 230                 235                 240

Val Leu Leu Gly Ser Ile Leu Leu Phe Leu Ile Val Val Ser Thr Val
                245                 250                 255

Leu Leu Phe Leu Arg Lys Gln Val Arg Met Leu Asp Val Glu Lys Cys
                260                 265                 270

Gly Val Glu Asp Thr Ser Ser Lys Asn Arg Asn Asp Thr Gln Phe Glu
                275                 280                 285

Glu Thr
    290

<210> SEQ ID NO 18
<211> LENGTH: 290
<212> TYPE: PRT
<213> ORGANISM: Macaca mulatta

<400> SEQUENCE: 18

Met Arg Ile Phe Ala Val Phe Ile Phe Thr Ile Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Arg Phe Pro Val Glu Lys Gln Leu
            35                  40                  45

Gly Leu Thr Ser Leu Ile Val Tyr Trp Glu Met Glu Asp Lys Asn Ile
    50                  55                  60

Ile Gln Phe Val His Gly Glu Glu Asp Leu Lys Val Gln His Ser Asn
65                  70                  75                  80

Tyr Arg Gln Arg Ala Gln Leu Leu Lys Asp Gln Leu Ser Leu Gly Asn
                85                  90                  95

Ala Ala Leu Arg Ile Thr Asp Val Lys Leu Gln Asp Ala Gly Val Tyr
                100                 105                 110

Arg Cys Met Ile Ser Tyr Gly Gly Ala Asp Tyr Lys Arg Ile Thr Val
            115                 120                 125

Lys Val Asn Ala Pro Tyr Asn Lys Ile Asn Gln Arg Ile Leu Val Val
130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Leu Asn
            180                 185                 190

Val Thr Ser Thr Leu Arg Ile Asn Thr Thr Ala Asn Glu Ile Phe Tyr
    195                 200                 205

Cys Ile Phe Arg Arg Leu Gly Pro Glu Glu Asn His Thr Ala Glu Leu
210                 215                 220

Val Ile Pro Glu Leu Pro Leu Ala Leu Pro Pro Asn Glu Arg Thr His
225                 230                 235                 240

Leu Val Ile Leu Gly Ala Ile Phe Leu Leu Leu Gly Val Ala Leu Thr
                245                 250                 255

Phe Ile Phe Tyr Leu Arg Lys Gly Arg Met Met Asp Met Lys Lys Ser
            260                 265                 270

Gly Ile Arg Val Thr Asn Ser Lys Lys Gln Arg Asp Thr Gln Leu Glu
```

Glu Thr
    290

<210> SEQ ID NO 19
<211> LENGTH: 288
<212> TYPE: PRT
<213> ORGANISM: Homo sapiens

<400> SEQUENCE: 19

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Phe Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 20
<211> LENGTH: 288
<212> TYPE: PRT
<213> ORGANISM: Macaca fascicularis

<400> SEQUENCE: 20

Met Gln Ile Pro Gln Ala Pro Trp Pro Val Val Trp Ala Val Leu Gln
1               5                   10                  15

Leu Gly Trp Arg Pro Gly Trp Phe Leu Glu Ser Pro Asp Arg Pro Trp
            20                  25                  30

```
Asn Ala Pro Thr Phe Ser Pro Ala Leu Leu Leu Val Thr Glu Gly Asp
         35                  40                  45
Asn Ala Thr Phe Thr Cys Ser Phe Ser Asn Ala Ser Glu Ser Phe Val
     50                  55                  60
Leu Asn Trp Tyr Arg Met Ser Pro Ser Asn Gln Thr Asp Lys Leu Ala
65                   70                  75                  80
Ala Phe Pro Glu Asp Arg Ser Gln Pro Gly Gln Asp Cys Arg Phe Arg
                 85                  90                  95
Val Thr Arg Leu Pro Asn Gly Arg Asp Phe His Met Ser Val Val Arg
                100                 105                 110
Ala Arg Arg Asn Asp Ser Gly Thr Tyr Leu Cys Gly Ala Ile Ser Leu
            115                 120                 125
Ala Pro Lys Ala Gln Ile Lys Glu Ser Leu Arg Ala Glu Leu Arg Val
            130                 135                 140
Thr Glu Arg Arg Ala Glu Val Pro Thr Ala His Pro Ser Pro Ser Pro
145                 150                 155                 160
Arg Pro Ala Gly Gln Phe Gln Thr Leu Val Val Gly Val Val Gly Gly
                165                 170                 175
Leu Leu Gly Ser Leu Val Leu Leu Val Trp Val Leu Ala Val Ile Cys
            180                 185                 190
Ser Arg Ala Ala Arg Gly Thr Ile Gly Ala Arg Arg Thr Gly Gln Pro
            195                 200                 205
Leu Lys Glu Asp Pro Ser Ala Val Pro Val Phe Ser Val Asp Tyr Gly
            210                 215                 220
Glu Leu Asp Phe Gln Trp Arg Glu Lys Thr Pro Glu Pro Pro Val Pro
225                 230                 235                 240
Cys Val Pro Glu Gln Thr Glu Tyr Ala Thr Ile Val Phe Pro Ser Gly
                245                 250                 255
Met Gly Thr Ser Ser Pro Ala Arg Arg Gly Ser Ala Asp Gly Pro Arg
            260                 265                 270
Ser Ala Gln Pro Leu Arg Pro Glu Asp Gly His Cys Ser Trp Pro Leu
            275                 280                 285
```